(12) United States Patent
Sommer

(10) Patent No.: US 6,361,949 B1
(45) Date of Patent: Mar. 26, 2002

(54) NUCLEIC ACID AMPLIFICATION WITH DIRECT SEQUENCING

(75) Inventor: Steven Seev Sommer, Rochester, MN (US)

(73) Assignee: Steve S. Sommer, Duarte, CA (US)

( * ) Notice: Subject to any disclaimer, the term of this patent is extended or adjusted under 35 U.S.C. 154(b) by 0 days.

(21) Appl. No.: 09/510,177

(22) Filed: Feb. 22, 2000

Related U.S. Application Data

(63) Continuation of application No. 08/399,855, filed on Dec. 27, 1994, now Pat. No. 6,027,913, which is a continuation of application No. 08/151,461, filed on Nov. 12, 1993, now abandoned, which is a continuation of application No. 07/385,013, filed on Jul. 24, 1989, now abandoned, which is a continuation-in-part of application No. 07/149,312, filed on Jan. 28, 1988, now abandoned.

(51) Int. Cl.$^7$ .............................. C12Q 1/68; C12Q 1/70
(52) U.S. Cl. ................................................ 435/6; 435/6
(58) Field of Search ............................. 435/5, 6, 91.2, 435/91.1, 69.1

(56) References Cited

U.S. PATENT DOCUMENTS

| | | | |
|---|---|---|---|
| 4,617,261 A | 10/1986 | Sheldon, III et al. | |
| 4,683,202 A | 7/1987 | Mullis | |
| 4,908,307 A | 3/1990 | Rodland et al. | |
| 6,027,913 A | 2/2000 | Sommer | |

OTHER PUBLICATIONS

Stoflet et al Science 239:491–494 Jan. 1988.*
Asubel, et al., (1987) "Current Protocols in Molecular Biology", *Green Publ. Assoc.*: 7.0.1–7.1.8.
Chapman, et al., (1988) "Bacteriophage T7 Late Promoters with Point Mutations: Quantitative Footprinting and In Vivo Expression", *Nucleic Acids Research*: 4511–4514.
Galili, et al., (1986) "Synthetic Oligonucleotide Tails Inhibit In Vitro an In Vivo Translation of SP6 Transcripts of Maize Zein cDNA Clones", *Nucleic Acids Research*, vol. 14: 1511–1524.
Engelke, et al., (1988) "Direct Sequencing of Enzymatically Amplified Human Genomic DNA", PNAS 85: 544–548.
Jagadeeswaran, et al., (1984) "Isolation and Characterization of Human Factor IX cDNA: Identification of Taq I Polymorphism and Regional Assignment", *Som. Cell Molec. Genet.*, vol. 10: 465–473.
Jagus (1987) "Translation in Cell–Free Systems", *Methods in Enzymology*, vol. 152: 267–276.
Jobling, et al., (1988) "In Vitro Transcription and Translational Efficiency of Chimeric SP6 Messenger RNAs Devoid of 5' Vector Nucleotides", *Nucleic Acids Research*, vol. 16: 4483–4498.
Kimmel and Berger (1987) "Preparation of cDNA and the Generation of cDNA Libraries", *Methods in Enzymology*, vol. 152: 307–316.

Konarska, et al., (1989) "Replication of RNA by the DNA–Dependent RNA Polymerase of Phage T7", Cell, vol. 57: 423–431.
Kristenesn, et al., (1988) "T7 DNA Polymerase in Automated Dideoxy Sequencing", *Nucleic Acids Research*, vol. 16: 3487–3488.
Krupp, (1989) "Unusual Promoter–Independent Transcription Reactions with Bacteriophage RNA Polymerases", *Nucleic Acids Research*, vol. 17: 3023–3036.
Lieber, et al., (1989) "High Level Gene Expression in Mammalian Cells by a Nuclear T7–Phage RNA Polymerase", *Nucleic Acids Research*, vol. 17: 8485–8487.
Ling, et al., (1989) "Abortive Initiation by Bacteriophage T3 and T7 RNA Polymerase Under Conditions of Limiting Substrate", *Nucleic Acids Research*, vol. 17: 1605–1618.
Maniatis, et al., (1989) "Molecular Cloning", *Cold Spring Harbor Press*: 5.40–5.43.
Maxam, et al., (1980) "Sequencing End–Labeled DNA with Base–Specific Chemical Cleavages", *Meth. Enzymol.*, 74: 499–560.
McCormick, (1989) "The Polymerase Chain Reaction and Cancer Diagnosis", *Cancer Cells*, vol. 1: 56–61.
McGraw, et al., (1985) "Evidence for a Prevalent Dimorphism in the Activation Peptide of Human Coagulation Factor IX", *Proc. Natl. Acad. Sci. USA*, 82: 2847–2851.
Milligan, et al., (1987) "Oligoribonucleotide Synthesis Using T7 RNA Polymerase and Synthetic DNA Templates", *Nucleic Acids Research*, vol. 15: 8783–8797.

(List continued on next page.)

*Primary Examiner*—Eggerton A. Campbell
(74) *Attorney, Agent, or Firm*—John P. White; Cooper & Dunham LLP

(57) ABSTRACT

This invention provides methods of amplifying a sequence of interest present within a nucleic acid molecule. In addition, this invention provides a method of determining the nucleotide sequence of a sequence of interest present within a nucleic acid molecule (e.g. GAWTS and RAWTS) which can be used to sequence tissue specific genes (e.g. tsRAWTS) and genes across species (e.g. zooRAWTS).

In addition, this invention provides a method of synthesizing a polypeptide encoded for by a nucleic acid molecule (RAWIT). Further, the subject invention provides a method of determining an internal nucleotide sequence present within a nucleic acid molecule, and a method of determining a terminal nucleotide sequence present within a nucleic acid molecule (e.g. PLATS).

Also provided for is a method of determining the nucleotide sequence of sequences present within a nucleic acid molecule which are adjacent to areas of known sequence (e.g ASWATS) and a method of determining the nucleotide sequence of sequences present within a nucleic acid molecule and a method of detecting point mutation or polymorphism (e.g. PASA) which can be used in low cost methods of carrier testing and prenatal diagnosis.

Lastly, this invention provides methods for determining the exonic nucleotide sequence of a gene as well as methods of detecting genomic mutations.

37 Claims, 31 Drawing Sheets

OTHER PUBLICATIONS

Ochman, H., et al., (1988) "Genetic Applications of an Inverse Polymerase Chain Reaction", *Genetics* 120: 621–623.

Oste, Christian, (1988) "Polymerase Chain Reaction", *BioTechniques*, vol. 6: 162–167.

Paddock, Gary, V., (1989) "Construction of mRNA Genes for the Synthesis and Translation of Duck Alpha Globin mRNA", *BioTechniques*, vol. 7: 856–865.

Sanger, et al., (1977) "DNA Sequencing with Chain–Terminating Inhibitors", *Proc. Nat'l. Acad. Sci. USA* 74: 5463–5467.

Schenborn, et al., (1985) "A Novel Transcription Property of SP6 and T7 RNA Polymerases: Dependence on Template Structure", *Nucleic Acids Research*, vol. 13: 6223–6235.

Schneider, et al., (1989) "Excess Information at Bacteriophage T7 Genomic Promoters Detected by a Random Cloning Technique", *Nucleic Acids Research*, vol. 17: 659–673.

Studier, William, F. and Moffatt, Barbara, A., (1986) "Use of Bacteriophage T7 RNA Polymerase to Direct Selective High–Level Expression of Cloned Genes", *J. Mol. Biol.*, vol. 189: 113–130.

Tabor, et al., (1987) "DNA Sequence Analysis with a Modified Bacteriophage T7 DNA Polymerase", *Proc. Natl. Acad. Sci. USA*, vol. 84: 4767–4771.

Vosberg, (1989) "The Polymerase Chain Reaction: An Improved Method for the Analysis of Nucleic Acids", *Hum. Genet.*, vol. 83: 1–15.

Wallace, (1987) "Large and Small–Scale Phenol Extractions", *Methods in Enzymology*, vol. 152: 33–41.

Williams, (1989) "Optimization Strategies for the Polymerase Chain Reaction", *BioTechniques*, vol. 7: 762–769.

Wong, et al., (1987) "Characterization of β–thalassaemia Mutations using Direct Genomic Sequencing of Amplified Single Copy DNA", *Nature* 330: 384–386.

* cited by examiner

FIGURE 1B

```
          1230  BP-E4(1230)-16D                    1259  BP-E4(1259)-17D
...ATG GTC AAC AAC CGT AAC CAT GGG CTG GAC TTA CGG CTT GTC ACC ATT CCT TCA
   Met Val Asn Asn Arg Asn His Gly Leu Asp Leu Arg Leu Val Thr Ile Pro Ser

1293  BP-E4(1293)-17D                                  1330
TTC TTC TCC AAG AGT GCT TGC ATC TAC AAT CGC ATC ATC TAC TGC TTC ATG AAT
Phe Phe Ser Lys Ser Ala Cys Ile Tyr Asn Pro Ile Ile Tyr Cys Phe Met Asn

GTAAAGCTCT...Intron 4 (987 bp total)...TTCTCTCCAG 1340                                     1438
AAG CAG TTC CAA...93bp...ACC CAA GTT GGC CCC AAC TGA GGACCCAATA TTGGCCTGTT...3'
Lys Gln Phe Gln                 Gln Val Gly Pro Asn
                                GTT CAA CCG GGG TTG
                                    1453
                                                           1476
                                AGA GGGATATCAC TGAGCATAAT CCATGG 5'
                                BP-(T7-29)E5(1453)-44U
```

FIGURE 4

```
human      30054  AAA GTT GAT GCA TTC TGT GGA GGC TCT ATC GTT AAT GAA AAA TGG ATT GTA
mouse                -   -   -   -   -   -   -  TGC A
rat                  -   -   -   -   -   -   -  GC  A
guinea pig         G  AC   A                    T   C           G                     C
rabbit             G   A  CG   T                T   C                                 G
sheep                      G   G                T       A                             GC
human        201  Lys Val Asp Ala Phe Cys Gly Gly Ser Ile Val Asn Glu Lys Trp Ile Val
mouse                -   -   -   -   -   -   -   -  Ala Ile
rat                  -   -   -   -   -   -   -   -  Ala Ile
guinea pig        Glu Thr Glu
rabbit            Glu Ile Ala Ser                                                     Val
sheep                      Glu                                  Ile                   Val
cow               Glu Ile Ala                                                         Val
```

```
                                                                        |Intron G|
ACT GCT GCC CAC TGT GTT GAA ACT GGT GTT AAA ATT ACA GTT GTC GCA GGT GAA CAT AAT ATT GAG
                 C   A   C       A           GAG     T   T           T   C           T
                 C   A   C       A           GAG T   T                   T            T
 A               A  CTC  C       A           GAG T           A                        A
     A        C  A  C   A   G   C                 T                     C  C
     A           A  C   A       C   G   A   T     T                     T  C          C
Thr Ala Ala His Cys Val Glu Thr Gly Val Lys Ile Thr Val Val Ala Gly Glu His Asn Ile Glu
                    Leu Lys Pro     Asp         Glu                     Tyr           Asp
                    Leu Lys Pro     Asp         Glu                                   Asp
                    Ile Leu         Ile         Glu                     Lys
                    Ile Lys Pro
                    Ile Lys Pro Asp Asp Asn                                           Gln
                    Ile Lys Pro                                                       Thr
```

```
GAG ACA GAA CAT ACA GAG CAA AAG CGA AAT GTG ATT CGA ATT ATT CCT CAC CAC AAC TAC AAT
 A      AG   G   C       A       G   A                   C   C       T       C  G
        AG   G   C       A       G   A                   C   C       T       C  G
 A      AG   G               G               CA  AG              TG          T  GT
 A   C       C                                C   T  GC          T           GGT
     T       G   A                                                           A
Glu Thr Glu His Thr Glu Gln Lys Arg Asn Val Ile Arg Ile Ile Pro His His Asn Tyr Asn 260
Lys Lys     Asp         Arg                         Thr                 Gln
    Lys     Asp         Arg                         Thr                 Gln
Lys Lys     Asp         Arg             Thr Gln             Leu         Ser
Lys Pro     Pro                             Ala             Tyr         Gly
        Asn                                                 Tyr         Lys
Lys Pro     Pro                             Ala             Tyr         Ser
```

FIGURE 6

```
                                    T7 Promoter                    E8(30884)-48D
                          ┌GGTACCTAATACGACTCACTATAGGGAGA┐┌─────────
        ....Thr Glu Gln Lys Arg Asn Val Ile Arg Ile Ile Pro His His Asn Tyr Asn Ala Ala Ile Asn Lys
244.
30851  5'...ACA GAG CAA AAG CGA AAT GTG ATT CGA ATT ATT CCT CAC CAC AAC TAC AAT GCA GCT ATT ATT AAG
       3'........TGT CTC GTT TTC GCT TTA CAC TAA GCT TAA TAA GGA GTG GTG TTG ATG TTA CGT CGA TAA TTA TTC Tyr Asn His Asp Ile Ala Leu Leu Glu Pro Leu Asp Leu Val Leu Asn Ser Tyr Val Thr Pro Ile Cys Ile
TAC AAC CAT GAC ATT GCC CTT CTG GAC GAA CCC CTT GTG CTA AAC AGC TAC GTT ACA CCT ATT TGC ATT
ATG TTG GTA CTG TAA CGG GAA GAC CTG CTT GGG AAT CAC GAT TTG TCG ATG CAA TGT GGA TAA ACG TAA Ala Asp Lys Glu Tyr Thr Asn Ile Phe Leu Lys Glu Tyr Val Ser Gly Trp Gly Arg Val      ...313
GCT GAC AAG GAA TAC ACG AAC ATC TTC CTC AAA TTT GGA TCT GTA AGT GGC TGG GGA AGA GTC   ...3'
CGA CTG TTC CTT ATG TGC TTG TAG AAG GAG TTT AAA CCT AGA CAT TCA CCG ACC CCT TCT CAG┘  GACGTCCAC...5' 31060
                                      └E8(31022)-17U┘    └─────E8(31048)-27U─────┘
```

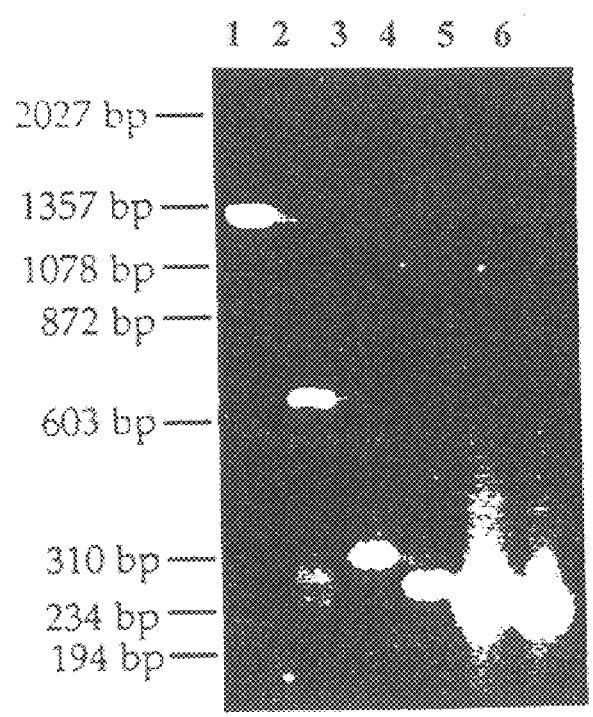
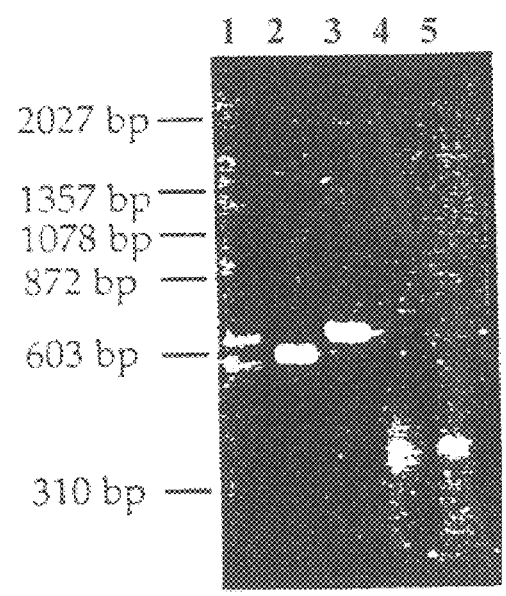
FIGURE 11A
FIGURE 11B

FIGURE 13

```
1    GAATT CAC GGA GAT AAC AAG ACT CGC AAA GAA GAA CGC AAG TTG CAT GAA GAA CGT TGG CAG GCA GCA TCC GCA GCA GCT CAT CAA CAT CTC
     Ile His Gly Asp Asn Lys Thr Arg Lys Glu Glu Arg Lys Leu His Glu Glu Arg Trp Gln Ala Ala Ser Ala Ala His Gln His Leu

93   TCA ACA CCA CAA ACG GCT GCA GGA GGT GGT GGT GGT GCA GTT ACT CTT CGT GAA GTT CGA ATG CCA GAG ATG CCA ATT CGT TAT GCT CCT AGT GAT GCT GTT
     Ser Thr Pro Gln Thr Ala Ala Gly Gly Gly Gly Ala Val Thr Leu Arg Glu Val Arg Met Pro Glu Met Pro Ile Arg Tyr Ala Pro Ser Asp Ala Val

183  GAA AAG TGG CTC AAC AAT CTT TTG TGC TGT GGT TCT ACG CCA AAT CGT ATC ATC GGT GTT ACA CCA CAT CCT CGT GAG TGT GAA
     Glu Lys Trp Leu Asn Asn Leu Leu Cys Cys Gly Ser Thr Pro Asn Arg Ile Ile Gly Gly Thr Pro His Pro Arg Glu Cys Glu

273  CTC TAC TAT GTT GAT CGT GAC TCG CTC TTT TCC TAC CAC AAG CTT CTC GAA AGC TTT TTG CAG CGC ATT ATG GCT CTA TAC GTT GCT TCT
     Leu Tyr Tyr Val Asp Arg Asp Ser Leu Phe Ser Tyr His Lys Leu Leu Glu Ser Phe Leu Gln Arg Ile Met Ala Leu Tyr Val Ala Ser

363  CAT TAC AAG AAT CAG CCA AAT CTT CAA TTG TCT CAT GCT CCA GCT CAT CAT TTT GTT CTT CTT GGA CCT CAA GCC GGA GAA GGA
     His Tyr Lys Asn Gln Pro Asn Leu Gln Leu Ser His Ala Pro Ala His His Phe Val Leu Leu Gly Pro Gln Ala Glu Gly

453  CAA GGC AAT GCT GGG CAG CTT TGC GTC GTC CAA GTT GCT GCT CTG GAA ATC TCA AAG GAA TCT GTT GCT GCA CAA
     Gln Gly Asn Ala Gly Gln Leu Cys Val Val Gln Val Ala Ala Leu Glu Ile Ser Lys Glu Ser Val Ala Ala Gln

543  CTC TCT CGA GGA CAA CGT GCC AGT GAT GGC GAT CTA ATT CCT ACG GTG GCT GCT CAA TTC CAG GAT AAT GAA TTT GCT GGT CTC TCT GGA
     Leu Ser Arg Gly Gln Arg Ala Ser Asp Gly Asp Leu Ile Pro Thr Val Ala Ala Gln Phe Gln Asp Asn Glu Phe Ala Gly Leu Ser Gly

633  GCC CGA GTG GTT GTG CGT ATT CGT ACG CAT CCT GAT GTC ACT GGA TAT GGC ATG GTG TCT CGT GCC GTT GAA TTA TTG ACA AAA TAC TAC CAA
     Ala Arg Val Val Arg Ile Arg Thr His Pro Asp Val Thr Gly Tyr Gly Met Val Ser Arg Ala Val Glu Leu Leu Thr Lys Tyr Tyr Gln

723  GGT GAA CTC GCA AGC GGT GAA TTT GAA GAT GAA AAC GAA GCT GCC AAG CCT GAC GAA GAA TCC GAT GAT GAA AGC AAT CTT CTC AAA
     Gly Glu Leu Ala Ser Gly Glu Phe Glu Glu Glu Asn Glu Ala Ala Lys Pro Asp Glu Glu Ser Asp Asp Glu Ser Asn Leu Leu Lys

813  GAA AAA GTC AAA CCT CGC AAA GCC CTT CCA CCC CTC ACA GAT CGT CCT GCT GAA CGC TTG CAT TGG TTT GGT TTT ACA TCG
     Glu Lys Val Lys Pro Arg Lys Ala Leu Pro Pro Leu Thr Asp Arg Pro Ala Glu Arg Leu His Trp Phe Gly Phe Thr Ser

903  TTC GGC TTG ACT CTT CAA CTT TAC ACC TTC TGG CAG CGC TCT GGT TTC CGA TCT GTT TAC ATT CGC CAA ACC GCG AAT CCA TTG AAC ACT GGT
     Phe Gly Leu Thr Leu Gln Leu Tyr Thr Phe Trp Gln Arg Ser Gly Phe Arg Ser Val Tyr Ile Arg Gln Thr Ala Asn Pro Leu Asn Thr Gly

993  GAG CAC ACT GCT ATT CTC ATG CTG AAA TGC GAC GAC CTG CAA TCT CCA GCT GCA GGA TGG CTT GAT GAA TTT GTT GGT GAC
     Glu His Thr Ala Ile Leu Met Leu Lys Cys Asp Asp Leu Gln Ser Pro Ala Ala Gly Trp Leu Asp Glu Phe Val Gly Asp

1083 GCT CGT AAA CGA TTC ATG TTG CTT ATG ACG TAT GCT GAA TTC
     Ala Arg Lys Arg Phe Met Leu Leu Met Ala Leu Ala Tyr Glu Phe
```

FIGURE 15

```
Aa1.2  Cys Leu Asp Cys Gly Ser Thr Pro Asn Arg Ile Ile Gly Gly Thr Pro His Pro Arg Glu Cys Glu Leu Tyr
RAD18  Cys Pro Ile Cys Gly Gln Phe Tyr Pro Leu Lys Ala Leu Glu Lys Thr His Leu Asp Glu Cys Leu Thr Gln
Cons   Cys xxx Val Cys Gly Asp xxx Ala xxx His Tyr xxx Gly xxx Lys xxx xxx Thr Cys Glu Gly Cys Lys Phe
```

FIGURE 16

F9-E1(61)-15U($T^{n-1}$)        GATTCTGCCATGA T C

Common Sequence (eg., E100M)    ...TGATTCTGCCATGA T CATGTTC...
                                              `—Bcl I—`

E91M Sequence                   ...TGATTCTGCCATGA A CATGTTC...

F9-E1(59)-12U($A^n$)                     TTCTGCCATGA A

F9-E1(62)-15U($A^n$)               TGATTCTGCCATGA A

F9-E1(61)-15U($A^{n-1}$)            GATTCTGCCATGA A C

F9-E1(60)-15U($A^{n-2}$, $C^{n-10}$, $T^{n-11}$)   ATTTCGCCATGA A CA

HB27 FAMILY

NUCLEIC ACID AMPLIFICATION WITH DIRECT SEQUENCING

This application is a continuation application of U.S. Ser. No. 08/399,855, filed Dec. 27, 1994, now U.S. Pat. No. 6,027,913, issued Feb. 22, 2000, which is a continuation of U.S. Ser. No. 08/151,461, filed Nov. 12, 1993 now abandoned, which is a continuation of U.S. Ser. No. 07/385,013, filed Jul. 24, 1989 now abandoned, which is a continuation-in-part of U.S. Ser. No. 07/149,312, filed Jan. 28, 1988 now abandoned, the contents of which are hereby incorporated by reference into the present application.

BACKGROUND OF THE INVENTION

Methods have been described for the direct sequencing of genomic DNA which are based on polymerase chain reaction (PCR) [Wong, et al. (1987) and Engelke, et al. (1988)]. Genomic amplification with transcript sequencing (GAWTS), incorporates a phage promoter sequence into at least one of the PCR primers and is described in the parent application serial no. 149,312, filed Jan. 28, 1988.

In contrast to autosomal recessive mutations, deleterious X-linked mutations are eliminated within a few generations because the affected males reproduce sparingly if at all. Thus, each family in an X-linked disease such as hemophilia B represents an independent mutation. From the perspective of efforts to understand the expression, processing, and function of factor IX, this is useful since a large number of mutations are potentially available for analysis. In addition to facilitating structure-function correlations, the rapidity of GAWTS makes it practical to perform direct carrier testing and prenatal diagnosis of at risk individuals. By amplifying and sequencing 11 regions of the hemophilic factor IX gene which total 2.8 kb, it should be possible to delineate the causative mutation in the overwhelming majority of individuals as these regions contain the putative promoter, the 5' untranslated region, the amino acid coding sequences, the terminal portion of the 3' untranslated region, and the intron-exon boundaries. Once the mutation is delineated, GAWTS can be used to directly test an at-risk individual, thereby finessing the multiple problems associated with indirect linkage analysis.

Another aspect of the subject invention concerns a direct method for rapidly obtaining novel sequences from clones involving promoter ligation and transcript sequencing, and uses thereof.

The hallmark of the steroid/thyroxine/retinoic acid receptor gene superfamily is a pair of zinc binding "fingers" which determine the specificity of DNA binding [Evans, R. M., Science, 240:889–895(1988). Certain amino acids in the zinc finger DNA binding domains are highly conserved, and recent members of this gene family have been found in Drosophila by analyzing sequences that cross-hybridize in a low stringency Southern blot with a human retinoic acid receptor cDNA probe [Oro, A. E., E. S. Ong, J. S. Margolis, J. W. Posakony, M. McKeown, and R. M. Evans, Nature 336:493–496 (1988)]. The inventor has used the same approach to isolate members of the superfamily in fungi since steroid-specific, high affinity binding proteins have been described in the cytosols of *Saccharomyces cervisiae*, *Paracoccidioides brasiliensis*, and *Candida albicans* [Burshell, A., P. A. Stathis, Y. Do, S. C. Miller, and D. Feldman, J. Biol. Chem, 259:3450–3456 (1984); Feldman, D., Y. Do, A. Burshell, P. Stathis, and D. S. Loose, Science, 218:297–298 (1982); Loose, D. S., and D. Feldman, J. Biol. Chem, 257:4925–4930 (1982); and Loose, D. S., D. J. Schurman and D. Feldman, Nature, 293:477–479 (1981)]. In the water mold *Achlya ambisexualis*, the receptor for antheridiol (a steroid that regulates sexual physiology) was found to have many of the same properties of steroid receptors in higher eucaryotes [Reihl, R. M., D. O. Toft, M. D. Meyer, G. L. Carlson and T. C. McMorris, Exp. Cell Res. 153:544–549 (1984); and Reihl, R. M., D. O. Toft, J. Biol. Chem., 259:15324–15330 (1984)].

Since false positive signals commonly occur with low stringency Southern blots, the inventor has developed a method called promoter ligation and transcript sequencing (PLATS) to allow rapid analysis of cross-hybridizing segments by reducing the effort required to determine the precise sequence of the segment. In a broader sense, PLATS is a general method for obtaining novel sequence which eliminates lambda DNA purification and subcloning steps which are required by conventional methods. PLATS is illustrated by sequencing a 1.1 kb segment of *Achlya ambisexualis* which cross-hybridizes to the DNA binding domain of the Xenopus and chicken estrogen receptor. This segment contains a transcribed open reading frame which is not a member of the steriod/thyroxine/retinoic acid receptor superfamily. However, the inventor speculates that the Achlya gene product may belong to a novel class of transcriptional regulators that bind DNA with a zinc finger containing three cysteines and one histidine.

The ability to screen populations for carriers of genetic disease in an accurate, inexpensive, and rapid manner would provide the opportunity for widespread genetic counseling and, ultimately, the possible elimination of such diseases. A successful example of protein based carrier screening is Tay-Sachs disease ($G_{M2}$ gangliosidosis type B), which is caused by a deficiency in β-hexosaminidase activity. Since non-carrier and carrier levels of enzymatic activity do not overlap, genetic status can be unequivocally assigned. [Ben-Yoseph, U., J. E. Reid, B. Shapiro, H. L. Nadler., Am. J. Hum. Genet., 37:733–748 (1985)] Screening for Tay-Sachs has reduced markedly the incidence of this disease in Ashkenazi Jews. [O'Brien, J. S., the gangliosidases, In: Stanbury J. B., J. B. Wyngaarden, D. S. Fredrickson, J. L. Goldstein, M. S. Brown, eds. Metabolic Basis of Inherited Disease. New York: McGraw-Hill, 1983:945–969]. Unfortunately, measurements of protein or metabolite levels for other genetic diseases are not usually accurate enough for this type of population screening. Population screening may eventually be possible, however, with DNA-based methods.

Phenylketonuria (PKU) is one disease amenable to DNA-based screening. Classical PKU is an autosomal recessive disease affecting one in 10,000 newborn Caucasians of northern European descent. The disease is the result of a deficiency in hepatic phenylalanine hydroxylase activity (PAH), which causes a primary elevation of serum phenylalanine and secondary abnormalities in compounds derived from aromatic amino acids. [Blau, K. In: Yondim M B H, ed. Aromatic Amino Hydoxylases and Mental Diseases. New York: Wiley, 1979:79–139] If left untreated in infancy, severe mental retardation ensures. While treatment with a low phenylalanine diet can prevent mental retardation, the disease has not been rendered benign. Phenylketonurics still encounter problems, including: 1) failure to reach full intellectual potential due to incomplete compliance with the very stringent dietary therapy [Holtzman, N. A., R. A. Kronmal, W. Van Doorninck, C. Azen, R. Koch, New Engl. J. Med., 314:593–598 (1986)]; 2) a high frequency of birth defects in children of affected females [Scriver, C. R., C. L. Clow, Ann Rev. Genet., 14:179–202 (1980)]; and 3) a high incidence of behavioral problems. [Holtzman, et al., (1986); Realmuto, G. M., B. D. Garfinkel, M. Tuckman, M. Y. Tsai, P-N. Chang, R. O. Fisch, S. Shapiro., J. Nerv. Mental Dis., 174: 536–540 (1986)]

Subsequent to the cloning of PAH cDNA, [Kwok, S. C. M., F. D. Ledley, A. G. DiLella, K. J. H. Robson, S. L. C. Woo. Biochem., 24:556–561 (1985)] it was found that 90% of the PKU alleles in the Danish population are confined to four haplotypes. [Chakraborty, R., A. S. Lidsky, S. P. Daiger, F., Guttler, S. Sullivan, A. G. DiLella, S. L. C. Woo., Hum. Genet., 76: 40–46.(1987)] The mutations in haplotypes 2 and 3 represent 20% and 40% of the PKU alleles, respectively. The mutation in haplotype 2 is a C to T transition at amino acid 408 in exon 12 of the PAH gene [DiLella, A. G., J. Marvit, K. Brayton, S. L. C. Woo., Nature, 327:333–336. (1987)] and the mutation in haplotype 3 is a G—A transition at the intron 12 donor splice junction. [DiLella, A. G., J. Marvit, A. S. Lidsky, F. Guttler, S. L. C. Woo., Nature, 322:799–803 (1986)] The mutant alleles associated with haplotypes 2 and 3 are also prevalent in the United States population. [Moore, S. D., W. M. Huang, R. Koch, S. Snyderman, S. L. C. Woo., Am. J. Hum. Genet., 43:A90 (1988)] When the mutations in haplotypes 1 and 4 are defined, 90% of all PKU carriers of northern European descent (approximately 4 million individuals in the United States alone) could be directly diagnosed by DNA methods.

The current methods which can detect such point mutations include: i) direct DNA sequencing, [Gyllensten, U. B., H. A. Erlich., Proc. Natl. Acad. Sci., 85:7652–7656 (1988)]; ii) denaturing gradient gel electrophoresis [Myers, R. M., N. Lumelsky, L. S. Lerman, T. Maniatas, Nature, 313:495–498 (1985)]; iii) polymerase chain reaction (PCR) followed by allele-specific oligonucleotide hybridization [DiLella, A. G., W-M. Huang, S. L. C. Woo., Lancet, 1:497–499 (1988)]; iv) allele specific DNA ligation [Landegren, U., R. Kaiser, J. Sanders, L. Hood, Science, 241:1077–1080 (1988)]; and v) ribonuclease cleavage of mismatched heteroduplexes. [R. M., Myers, Z. Larin, T. Maniatas. Science, 230:1242–1246 (1985)] However, these techniques in their present form are unlikely to find widespread application in population screening because they lack the requisite speed, technical ease, and/or cost effectiveness.

This invention extends GAWTS by providing a method for rapid and direct access to an mRNA sequence or its protein product which is not limited by either tissue or species specificity. In addition, this application provides a direct method for rapidly obtaining novel sequences from clones involving promoter ligation and transcript sequencing.

Lastly, the subject invention provides a method for polymerase chain reaction amplification of specific alleles to reliably distinguish between alleles differing in only part.

SUMMARY OF THE INVENTION

The subject invention provides a method of amplifying a sequence of interest present within a nucleic acid molecule which comprises:

A) obtaining a sample of the nucleic acid molecule which contains the sequence of interest;

B) if the nucleic acid molecule is a single-stranded RNA molecule, treating the sample from step (A) so as to prepare a sample containing a DNA molecule which contains a sequence complementary to the sequence of interest;

C) treating the sample from step (A) if the nucleic acid molecule is a DNA molecule or the sample from step (B) if the nucleic acid molecule is a single-stranded RNA molecule so as to obtain a further sample containing a single-stranded DNA molecule which contains a sequence complementary to the sequence of interest;

D) contacting the further sample from step (C) under hybridizing conditions with one oligonucleotide primer which includes at least (a) a promoter and (b) a nucleic acid sequence present within the nucleic acid molecule which contains the sequence of interest, which primer sequence is located adjacent to, and 5' of, the sequence of interest, so that the oligonucleotide primer hybridizes with the single-stranded DNA molecule which contains the sequence complementary to the sequence of interest;

E) treating the resulting sample containing the single-stranded DNA molecule to which the oligonucleotide primer is hybridized from step (D) with a polymerase under polymerizing conditions so that a DNA extension product of the oligonucleotide primer is synthesized, which DNA extension product contains the sequence of interest;

F) treating the sample from step (E) so as to separate the DNA extension product from the single-stranded DNA molecule on which it was synthesized and thereby obtain single-stranded DNA molecules;

G) contacting the resulting sample from step (F) containing the single-stranded DNA molecule which contains the sequence complementary to the sequence of interest under hybridizing conditions, with one oligonucleotide primer, which includes at least (a) a promoter and (b) a nucleic acid sequence located adjacent to, and 5' of, the sequence of interest, so that the oligonucleotide primer hybridizes with the single-stranded DNA molecule present in the sample which contains the sequence complementary to the sequence of interest;

H) treating the sample containing the single-stranded DNA molecule to which the oligonucleotide primer is hybridized from step (G) with a polymerase so as to synthesize a further DNA extension product containing the sequence complementary to the sequence of interest;

I) repeating steps (F) through (H), as desired;

J) contacting the sample from step (I) with an RNA polymerase which initiates polymerization from the promoter present, under polymerizing conditions, so as to obtain multiple RNA transcripts of each DNA extension product which contains the sequence complementary to the sequence of interest, thereby amplifying the sequence of interest.

The subject invention provides a second method which is a method of amplifying a sequence of interest present within a nucleic acid molecule which comprises:

A) obtaining a sample of the nucleic acid molecule which contains the sequence of interest;

B) if the nucleic acid molecule is a single-stranded RNA molecule, treating the sample from step (A) so as to prepare a sample containing a DNA molecule which contains a sequence complementary to the sequence of interest;

C) treating the sample from step (A) if the nucleic acid molecule is a DNA molecule or the sample from step (B) if the nucleic acid molecule is a single-stranded RNA molecule so as to obtain a further sample containing a single-stranded DNA molecule which contains a sequence complementary to the sequence of interest;

D) contacting the further sample from step (C) under hybridizing conditions with two or more oligonucleotide primers at least one of which includes at least (a) a promoter and (b) a nucleic acid sequence present within the nucleic acid molecule which contains the sequence of interest, which primer sequence is located adjacent to, and 5' of, the sequence of interest, and at least one other of which includes a nucleic acid sequence complementary to a sequence present within the nucleic acid molecule which contains the sequence of interest, which primer sequence is located adjacent to, and 5' of, the nucleic acid sequence complementary to the sequence within the nucleic acid molecule which contains the sequence of interest, so that at least one of the oligonucleotide primers hybridizes with the single-stranded DNA molecule present in the sample which contains the sequence complementary to the sequence of interest, and at least one other of the oligonucleotide primers hybridizes with the single-stranded DNA molecule which contains the sequence of interest;

E) treating the resulting sample containing the single-stranded DNA molecules to which the oligonucleotide primers are hybridized from step (D) with a polymerase under polymerizing conditions so that DNA extension products of the oligonucleotide primers are synthesized, some of which DNA extension products contain the sequence of interest and some of which DNA extension products contain the sequence complementary to the sequence of interest;

F) treating the sample from step (E) so as to separate the DNA extension products from the single-stranded DNA molecules on which they were synthesized and thereby obtain single-stranded DNA molecules;

G) contacting the resulting sample from step (F) containing the single-stranded DNA molecule which contains the sequence complementary to the sequence of interest under hybridizing conditions, with two or more oligonucleotide primers at least one which includes at least (a) a promoter and (b) a nucleic acid sequence located adjacent to, and 5' of, the sequence of interest, and at least one other of which includes a nucleic acid sequence complementary to a sequence present within the nucleic acid molecule which contains the sequence of interest, which primer sequence is located adjacent to, and 5' of, the nucleic acid sequence complementary to the sequence within the nucleic acid molecule which contains the sequence of interest, so that at least one of the oligonucleotide primers DNA molecule present in the sample which contains the sequence complementary to the sequence of interest, and at least one other of the oligonucleotide primers hybridizes with the single-stranded DNA molecule which contains the sequence of interest;

H) at least treating the sample containing the single-stranded DNA molecules to which the oligonucleotide primers are hybridized from step (G) with polymerase so as to synthesize further DNA extension products, some of which DNA extension products contain the sequence of interest and some of which DNA extension products contain the sequence complementary to the sequence of interest;

I) repeating steps (F) through (H), as desired;

J) contacting the sample from step (I) with an RNA polymerase which initiates polymerization from the promoter present, under polymerizing conditions, so as to obtain multiple RNA transcripts of each DNA extension product which contains the sequence complementary to the sequence of interest, thereby amplifying the sequence of interest.

Further the subject invention provides a method of determining the nucleotide sequence of a sequence of interest present within a nucleic acid molecule which comprises:

a) amplifying the amount of the sequence of interest present within a nucleic acid molecule;

b) if the sequence generated in step (a) is double-stranded, treating the molecule to generate single-stranded nucleic acid molecules;

c) determining the sequence of the single-stranded nucleic acid molecules of either step (a) or (b) thereby determining the nucleotide sequence of the sequence of interest.

The subject invention further comprises a method of determining an internal nucleotide sequence present within a nucleic acid molecule which contains promoters at both ends of the nucleic acid molecule which comprises:

a) cleaving the nucleic acid molecule under such conditions so as to generate fragments of the nucleic acid molecule;

b) if the fragments of the nucleic acid molecule do not have blunt ends, treating the fragments of the nucleic acid molecule so as to generate blunt ends;

c) ligating a promoter to the blunt end of a fragment of the nucleic acid molecule obtained in step (a) or (b);

d) amplifying a sequence of the fragment of the nucleic acid molecule containing the promoter obtained in step (c);

e) transcribing the amplified fragment of the nucleic acid molecule obtained in step (d); and f) sequencing the transcript obtained in step (e) thereby determining an internal nucleotide The subject invention also provides a method of determining the nucleotide sequence of sequences present within a nucleic acid molecule which are adjacent to areas of known sequence which comprises:

a) cleaving the nucleic acid molecule adjacent to the sequences of interest under conditions so as to generate fragments of the nucleic acid molecule which contain the sequences of interest;

b) if the fragments of the nucleic acid molecule do not have blunt ends, treating the fragments of the nucleic acid molecule so as to generate blunt ends;

c) contacting the fragments containing the sequences of interest obtained in step (a) or (b) with an oligonucleotide containing two different promoter sequences adjacent to each other by blunt end ligation under conditions such that the promoter sequence binds adjacent to the sequence of interest and it is unlikely that the fragment will bind a promoter at both ends;

d) transcribing the fragments containing the sequences of interest and promoter sequence obtained in step (c) using a polymerase specific to the 5' promoter sequence;

e) degrading or removing the fragments which were generated in steps (a) and (b);

f) synthesizing a nucleic acid sequence complementary to the first sequence to be determined using a downstream primer specific for the known sequence adjacent to the first sequence to be determined;

g) amplifying the amount of fragments containing the sequence to be determined using a downstream primer specific for the known sequence adjacent to the second sequence to be determined and an upstream primer specific for the second promoter sequence;

h) transcribing the fragments containing the sequence of interest using a polymerase specific to the second promoter sequence;

i) sequencing using a downstream primer specific for the third known sequence.

BRIEF DESCRIPTION OF THE FIGURES

FIG. 1B: oligonucleotides for RAWTS of a segment of blue pigment mRNA. Portions of exons 4 and 5 which correspond to the amplified region are illustrated.

FIG. 4: Cross-species sequencing with RAWTS (ZooRAWTS). A comparison of novel nucleotide and amino acid sequences of amino acids 201–260 of the factor IX gene of mouse, rat, guinea pig, rabbit, sheep and cow.

FIG. 6: Region of factor IX gene and location of the PCR primers and the reverse transcriptase primer to sequence one region of factor IX gene of the present invention.

FIG. 11A: 2.0% agarose gel of the amplified 1.1 kb Achyla clone followed by digestion with Rsa 1 promoter ligation, amplification, and transcription.

FIG. 11B: Generation of sequencing templates subsequent to Taq 1 restriction enzyme digestion of Aa1.1. After digestion, blunt ends were generated with Klenow.

FIG. 13: The nucleotide and amino acid sequences of Aa1.1 The lambda gt10 Eco R1 cloning sites have been underlined. The 5' box outlines a possible DNA binding "zinc finger" domain as noted in the specification. The 3' box outlines an acidic region of 19 amino acids with 58% Asp+Glu. The region of 76% similarity to the Xenopus estrogen receptor DNA binding region probe is 752–789, and is indicated in bold face type and arrows.

FIG. 15: Sequence comparison between the proposed zinc finger domain of the Aa1.1, RAD18 third finger domain [Evans (1988)], and the consensus sequence (cons) for the first zinc finger of the steroid receptor family [Evans and Hollenberg (1988)].

FIG. 16: Sequence of selected Factor Ix oligonucleotides.

DETAILED DESCRIPTION OF THE INVENTION

Figure 1A:
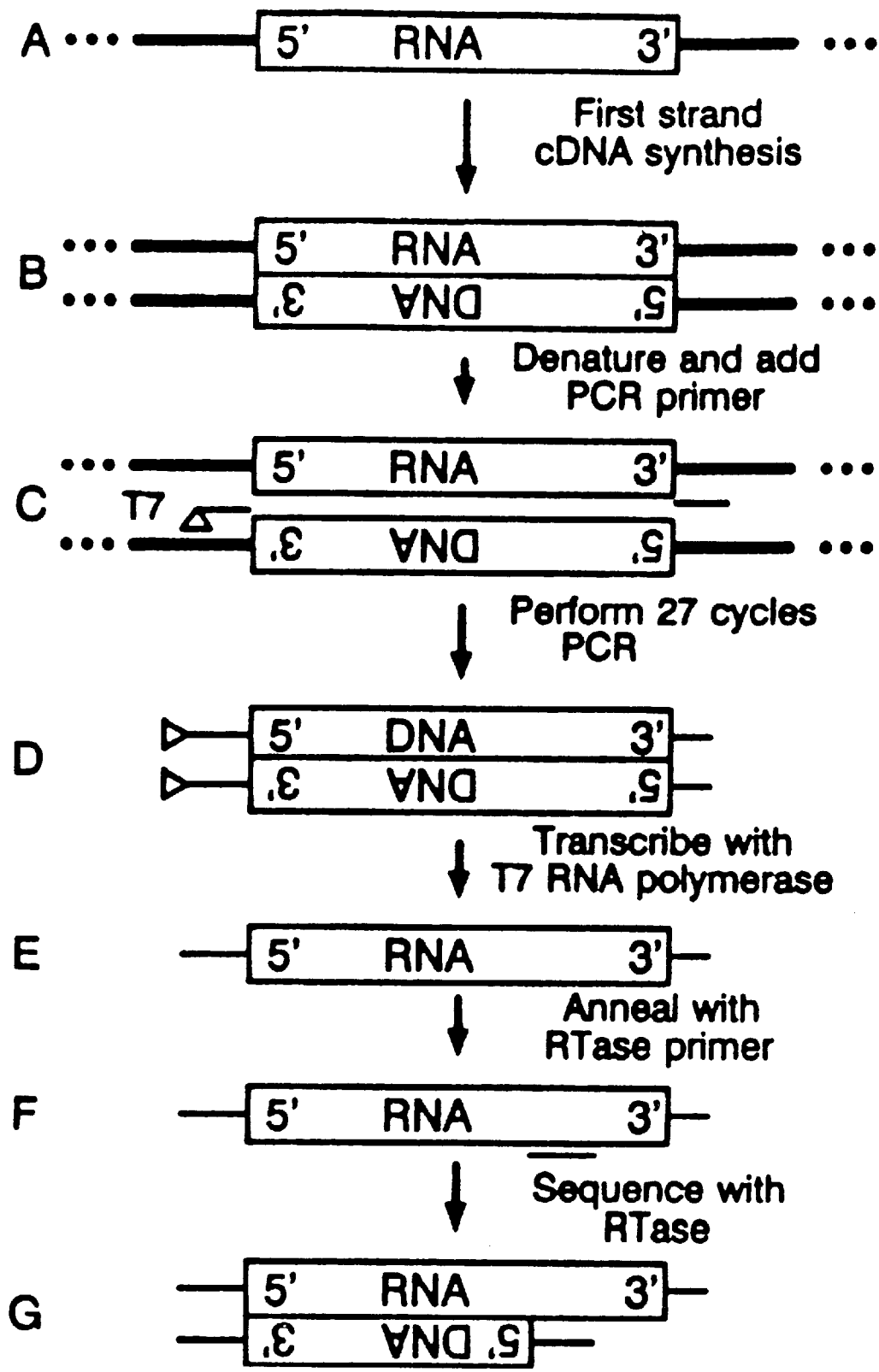
FIG. 1A: Schematic representation of RNA amplification with transcript sequencing (RAWTS).

As used throughout this application, the following terms will have the following meanings:

GAWTS—Genomic amplification with transcript sequencing.

RAWTS—RNA amplification with transcript sequencing.

tsRAWTS—RAWTS of tissue specific genes in tissues where the gene expression is not detected by conventional methods.

RAWIT—RNA amplification with in vitro translation.

zooRAWTS—Sequencing homologous genes across species.

ASAWTS—Adjacent sequence amplification with transcript sequencing.

PASA—Polymerase chain reaction amplification of specific alleles

PLATS—Promoter ligation with transcript sequencing.

"sequence of interest" —Nucleic acid "sequence of interest" encompasses sequences having identical nucleotide sequences as well as sequences having corresponding nucleotide sequences. For example, in the case of a DNA molecule the term "sequence of interest" includes both the identical DNA sequence and the corresponding, as distinct from complementary, RNA sequence.

The subject invention provides a method of amplifying a sequence of interest present within a nucleic acid molecule which comprises:

A) obtaining a sample of the nucleic acid molecule which contains the sequence of interest;

B) if the nucleic acid molecule is a single-stranded RNA molecule, treating the sample from step (A) so as to prepare a sample containing a DNA molecule which contains a sequence complementary to the sequence of interest;

C) treating the sample from step (A) if the nucleic acid molecule is a DNA molecule or the sample from step (B) if the nucleic acid molecule is a single-stranded RNA molecule so as to obtain a further sample containing a single-stranded DNA molecule which contains a sequence complementary to the sequence of interest;

D) contacting the further sample from step (C) under hybridizing conditions with one oligonucleotide primer which includes at least (a) a promoter and (b) a nucleic acid sequence present within the nucleic acid molecule which contains the sequence of interest, which primer sequence is located adjacent to, and 5' of, the sequence of interest, so that the oligonucleotide primer hybridizes with the single-stranded DNA molecule which contains the sequence complementary to the sequence of interest;

E) treating the resulting sample containing the single-stranded DNA molecule to which the oligonucleotide primer is hybridized from step (D) with a polymerase under polymerizing conditions so that a DNA extension product of the oligonucleotide primer is synthesized, which DNA extension product contains the sequence of interest;

F) treating the sample from step (E) so as to separate the DNA extension product from the single-stranded DNA molecule on which it was synthesized and thereby obtain single-stranded DNA molecules;

G) contacting the resulting sample from step (F) containing the single-stranded DNA molecule which contains the sequence complementary to the sequence of interest under hybridizing conditions, with one oligonucleotide primer, which includes at least (a) a promoter and (b) a nucleic acid sequence located adjacent to, and 5' of, the sequence of interest, so that the oligonucleotide primer hybridizes with the single-stranded DNA molecule present in the sample which contains the sequence complementary to the sequence of interest;

H) treating the sample containing the single-stranded DNA molecule to which the oligonucleotide primer is hybridized from step (G) with a polymerase so as to synthesize a further DNA extension product containing the sequence complementary to the sequence of interest;

I) repeating steps (F) through (H), as desired;

J) contacting the sample from step (I) with an RNA polymerase which initiates polymerization from the promoter present, under polymerizing conditions, so as to obtain multiple RNA transcripts of each DNA extension product which contains the sequence complementary to the sequence of interest, thereby amplifying the sequence of interest.

The subject invention provides a second method which is a method of amplifying a sequence of interest present within a nucleic acid molecule which comprises:

A) obtaining a sample of the nucleic acid molecule which contains the sequence of interest;

B) if the nucleic acid molecule is a single-stranded RNA molecule, treating the sample from step (A) so as to prepare a sample containing a DNA molecule which contains a sequence complementary to the sequence of interest;

C) treating the sample from step (A) if the nucleic acid molecule is a DNA molecule or the sample from step (B) if the nucleic acid molecule is a single-stranded RNA molecule so as to obtain a further sample containing a single-stranded DNA molecule which contains a sequence complementary to the sequence of interest;

D) contacting the further sample from step (C) under hybridizing conditions with two or more oligonucleotide primers at least one of which includes at least (a) a promoter and (b) a nucleic acid sequence present within the nucleic acid molecule which contains the sequence of interest, which primer sequence is located adjacent to, and 5' of, the sequence of interest, and at least one other of which includes a nucleic acid sequence complementary to a sequence present within the nucleic acid molecule which contains the sequence of interest, which primer sequence is located adjacent to, and 5' of, the nucleic acid sequence complementary to the sequence within the nucleic acid molecule which contains the sequence of interest, so that at least one of the oligonucleotide primers hybridizes with the single-stranded DNA molecule present in the sample which contains the sequence complementary to the sequence of interest, and at least one other of the oligonucleotide primers hybridizes with the single-stranded DNA molecule which contains the sequence of interest;

E) treating the resulting sample containing the single-stranded DNA molecules to which the oligonucleotide primers are hybridized from step (D) with a polymerase under polymerizing conditions so that DNA extension products of the oligonucleotide primers are synthesized, some of which DNA extension products contain the sequence of interest and some of which DNA extension products contain the sequence complementary to the sequence of interest;

F) treating the sample from step (E) so as to separate the DNA extension products from the single-stranded DNA molecules on which they were synthesized and thereby obtain single-stranded DNA molecules;

G) contacting the resulting sample from step (F) containing the single-stranded DNA molecule which contains the sequence complementary to the sequence of interest under hybridizing conditions, with two or more oligonucleotide primers at least one which includes at least (a) a promoter and (b) a nucleic acid sequence located adjacent to, and 5' of, the sequence of interest, and at least one other of which includes a nucleic acid sequence complementary to a sequence present within the nucleic acid molecule which contains the sequence of interest, which primer sequence is located adjacent to, and 5' of, the nucleic acid sequence complementary to the sequence within the nucleic acid molecule which contains the sequence of interest, so that at least one of the oligonucleotide primers DNA molecule present in the sample which contains the sequence complementary to the sequence of interest, and at least one other of the oligonucleotide primers hybridizes with the single-stranded DNA molecule which contains the sequence of interest;

H) at least treating the sample containing the single-stranded DNA molecules to which the oligonucleotide primers are hybridized from step (G) with polymerase so as to synthesize further DNA extension products, some of which DNA extension products contain the sequence of interest and some of which DNA extension products contain the sequence complementary to the sequence of interest;

I) repeating steps (F) through (H), as desired;

J) contacting the sample from step (I) with an RNA polymerase which initiates polymerization from the promoter present, under polymerizing conditions, so as to obtain multiple RNA transcripts of each DNA extension product which contains the sequence complementary to the sequence of interest, thereby amplifying the sequence of interest.

In one preferred embodiment of methods one and two, the nucleic acid molecule containing the sequence of interest comprises double-stranded DNA. Another preferred embodiment is wherein the double-stranded DNA comprises genomic DNA. The nucleic acid molecule containing the sequence of interest can also comprise cDNA.

Other embodiments of the subject invention are wherein the nucleic acid molecule containing the sequence of interest comprises RNA or more specifically, wherein the nucleic acid molecule containing the sequence of interest comprises mRNA.

The sample of the nucleic acid molecule which contains the sequence of interest may vary depending on the sequence of interest to be amplified and are reality determinable to one skilled in the art. In a preferred embodiment, the sample comprises a biological sample. This biological sample may be any biological sample conducive to amplification. One preferred embodiment is wherein the biological sample is a cell sample and another is wherein the biological sample is a tissue sample. In one embodiment, the tissue sample is blood.

The choice of promoter to be used is readily determinable to one skilled in the art and will vary upon application. In the preferred embodiment, the promoter is a phage promoter, and more preferably, a T7 promoter, a T3 promoter, or an SP6 promoter.

In another embodiment of the first two methods, in step (D) the oligonucleotide primer which hybridizes with the single-stranded DNA molecule which contains the sequence complementary to the sequence of interest comprises a T7 promoter and in step (J) the RNA polymerase comprises a T7 RNA polymerase.

Further, a preferred method of both methods one and two is wherein in step (D) the oligonucleotide primer which hybridizes with the single-stranded DNA molecule which contains the sequence complementary to the sequence of interest comprises a T3 promoter and in step (J) the RNA polymerase comprises a T3 RNA polymerase. And yet a further preferred method of methods one and two is wherein in step (D) the oligonucleotide primer which hybridizes with the single-stranded DNA molecule which contains the sequence complementary to the sequence of interest comprises a SP6 promoter and in step (J) the RNA polymerase comprises a SP6 RNA polymerase.

This method is not limited by tissue specificity and may be used for obtaining novel mRNA sequences from other species. In turn, the mRNA sequences obtained may be used to aid in the study of protein evolution and the identification of sequences crucial for protein structure and function.

The third method provided by the subject invention is a method of determining the nucleotide sequence of a sequence of interest present within a nucleic acid molecule which comprises:

a) amplifying the sequence of the nucleic acid molecule to be determined using one of the first two described methods;

b) treating the sample from step (J) of method one or method two, under conditions such that a primer hybridizes to the RNA transcript;

c) contacting the sample from step (b) with a polymerase under polymerizing conditions such that a single-stranded nucleic acid molecule which is complementary to the RNA transcript is synthesized; and d) determining the nucleotide sequence of the single-stranded nucleic acid molecule obtained in step (c) thereby determining the nucleotide sequence of a sequence of interest.

The choice of polymerase will depend on conditions employed. However, the choice of polymerase is readily determinable to one skilled in the art. One preferred embodiment is wherein the polymerase is reverse transcriptase.

A preferred embodiment of this method is wherein in step (d) the determining comprises enzymatic sequencing, and more preferably Sanger dideoxy sequencing.

In another embodiment in step (d) the determining comprises chemical sequencing, and more preferably, Maxam Gilbert sequencing.

In yet another embodiment in step (d) the determining comprises both chemical and enzymatic sequencing and even more preferably comprises the use of phosphorothioate.

The fourth method provided by the subject invention is a method of determining the nucleotide sequence of a sequence of interest present within a nucleic acid molecule which comprises:

a) amplifying the amount of the sequence of interest present within a nucleic acid molecule;

b) if the sequence generated in step (a) is double-stranded, treating the molecule to generate single-stranded nucleic acid molecules;

c) determining the sequence of the single-stranded nucleic acid molecules of either step (a) or (b) thereby determining the nucleotide sequence of the sequence of interest.

In a preferred embodiment, in step (c) the determining comprises enzymatic sequencing, and more preferably, Sanger dideoxy sequencing.

In another embodiment, in step (c) the determining comprises chemical sequencing, and more preferably Maxam Gilbert sequencing.

In yet another embodiment, in step (c) the determining comprises both chemical and enzymatic sequencing, and more preferably, comprises the use of phosphorothioate.

The fifth method provided by the subject invention is a method of synthesizing a polypeptide encoded for by a nucleic acid molecule which comprises:

a) amplifying a sequence of interest present within a nucleic acid molecule which encodes for the polypeptide to be synthesized using the method of either of the first two methods described hereinabove wherein at least one of the oligonucleotides contains a translation initiation signal 3' to the promoter; and b) translating the RNA of step (a) to produce the polypeptide or fragment thereof encoded for by the nucleic acid molecule.

Proteins may be recovered by any of the conventional methods including but limited to HPLC, electro- phoresis, size exclusion etc. These methods being well known to those skilled in the art. This method may be utilized in a method of producing a therapeutic agent containing one or more polypeptides or fragments thereof which comprises synthesizing the polypeptide or fragment thereof by the above-identified method.

The sixth method disclosed by the subject invention is a method of determining an internal nucleotide sequence present within a nucleic acid molecule which contains promoters at both ends of the nucleic acid molecule which comprises:

a) cleaving the nucleic acid molecule under such conditions so as to generate fragments of the nucleic acid molecule;

b) if the fragments of the nucleic acid molecule do not have blunt ends, treating the fragments of the nucleic acid molecule so as to generate blunt ends;

c) ligating a promoter to the blunt end of a fragment of the nucleic acid molecule obtained in step (a) or (b);

d) amplifying a sequence of the fragment of the nucleic acid molecule containing the promoter obtained in step (c);

e) transcribing the amplified fragment of the nucleic acid molecule obtained in step (d); and f) sequencing the transcript obtained in step (e) thereby determining an internal nucleotide sequence present within nucleic acid molecule.

One preferred embodiment is wherein in step (c) the promoter comprises a double-stranded promoter. Another embodiment is wherein in step (a) the cleaving comprises shearing the nucleic acid molecule. And in a further embodiment, in step (a) the cleaving comprises the use of a restriction endonuclease. The choice of cleaving method is well within the skill of one in the art.

The choice of promoter is also determinable to one skilled in the art. However, in the preferred embodiment, the promoters comprise phage promoters. The most preferred embodiment being wherein the promoters are a T7 promoter, a T3 promoter, and a SP6 promoter.

The subject invention further discloses a seventh method which is a method of determining a terminal nucleotide sequence present within a nucleic acid molecule which comprises:

a) digesting a nucleic acid molecule with one or more restriction enzymes to generate fragments of the nucleic acid molecule having either blunt ends, or 5' overhangs;

b) if the nucleic acid fragment has a 5' overhangs, treating the fragment of the nucleic acid molecule obtained in step (a) to generate blunt ends;

c) contacting the fragment obtained in step (b) with two different primer sequences containing different promoters under hybridizing conditions, one primer sequence being specific to the 3' end of the first strand of the nucleic acid molecule to be sequenced and the other specific to the 3' end of the complementary strand;

d) ligating a double-stranded promoter sequence to the fragment of the nucleic acid molecule obtained in step (c);

e) determining the first terminal nucleotide sequence of the fragment of the nucleic acid molecule obtained in the step (d) by the third described method, wherein the RNA polymerase is specific to the first primer sequence containing a phage promoter and the reverse transcriptase is primed with the promoter which was ligated in step (d) thereby determining the nucleotide sequence of the first terminal; and f) determining the second terminal nucleotide sequence of the nucleic acid by the third described method, wherein the polymerase is specific to the second primer sequence containing a promoter and the reverse transcriptase is primed with the promoter which was ligated in step (d) thereby determining the nucleotide sequence of the second terminal.

One embodiment of this method is wherein the treating of step (d) comprises the use of the Klenow fragment.

The choice of restriction enzyme will vary greatly and will depend upon the nucleic acid sequence to be determined. The choice of restriction enzyme is readily determinable by one skilled in the art. Restriction enzymes that may be used include, by are not limited to, Alu 1, Mn1 1, Hind III and Hae III.

It is preferred that the determining steps comprise a preliminary step of separating out the segment of, correct size. This reduces the number of spurious amplification products because PCR primers produce an abundance of short transcripts. Addition of this step produces clearer results. The isolation of the appropriate sized clone maybe realized by any method known in the art but the preferred separation is performed on agarose gel. The transcribing may be effected with any polymerase known to be effective in the art. This method allows rapid analysis of cross-hybridizing segments by reducing the effort required to determine the precise sequence of the segment. The method provides an advantage over the prior art by obtaining novel sequence which eliminate lambda DNA purification and subcloning steps which are required by conventional methods.

The eighth method disclosed by the subject invention is a method of determining the nucleotide sequence of sequences present within a nucleic acid molecule which are adjacent to areas of known sequence which comprises:

a) cleaving the nucleic acid molecule adjacent to the sequences of interest under conditions so as to generate fragments of the nucleic acid molecule which contain the sequences of interest;

b) if the fragments of the nucleic acid molecule do not have blunt ends, treating the fragments of the nucleic acid molecule so as to generate blunt ends;

c) contacting the fragments containing the sequences of interest obtained in step (a) or (b) with an oligonucleotide containing two different promoter sequences adjacent to each other by blunt end ligation under conditions such that the promoter sequence binds adjacent to the sequence of interest and it is unlikely that the fragment will bind a promoter at both ends;

d) transcribing the fragments containing the sequences of interest and promoter sequence obtained in step (c) using a polymerase specific to the 5' promoter sequence;

e) degrading or removing the fragments which were generated in steps (a) and (b);

f) synthesizing a nucleic acid sequence complementary to the first sequence to be determined using a downstream primer specific for the known sequence adjacent to the first sequence to be determined;

g) amplifying the amount of fragments containing the sequence to be determined using a downstream primer specific for the known sequence adjacent to the second sequence to be determined and an upstream primer specific for the second promoter sequence;

h) transcribing the fragments containing the sequence of interest using a polymerase specific to the second promoter sequence;

i) sequencing using a downstream primer specific for the third known sequence.

In a preferred embodiment of the eighth method, step (b) further comprises treating the blunt ends of the fragments with an endonuclease to generate one 3' overhang which is resistant to blunt end ligation at that end.

Another embodiment is wherein step (a) the cleaving comprises treating the nucleic acid molecule with a restriction endonuclease. One skilled in the art can readily determine the appropriate restriction endonuclease for use.

One preferred embodiment is wherein in step (a) the cleaving comprises shearing the nucleotide. Another embodiment is wherein step (b) further comprises the removal of self-priming RNA. Additionally, an embodiment is provided wherein the amplifying of step (g) comprises multiple rounds of polymerase chain reaction.

The subject invention also discloses a ninth method which is a method of detecting a point mutation or polymorphism in a nucleic acid molecule which comprises:

a) amplifying the sequence of interest present within the nucleic acid molecule by method one or two described above wherein the oligonucleotide primer sequence of interest hybridizes to a sequence of the nucleic acid molecule containing the nucleotide point mutation;

b) determining the amount RNA produced in step (G) of method one or two; and c) comparing the amount of RNA corresponding to the sequence of interest which has been produced with the amount of RNA expected, an increased amount of RNA indicating the presence of point mutation.

This method can be further utilized in a method of carrier testing which comprises:

a) obtaining a sample containing the nucleic acid molecule of interest from a subject; and b) detecting the presence of a point mutation in the nucleic acid molecule of interest using the above-described method thereby determining whether the subject is a carrier.

This method may also be used in a method of prenatal diagnosis which comprises:

a) obtaining a sample containing the nucleic acid molecule of interest from a subject; and b) detecting the presence of a point mutation in the nucleic acid molecule of interest using the above-identified method thereby determining whether the subject has the tested for mutation.

The invention also provides a method of detecting the presence a mutation or polymorphism in a nucleic acid molecule which comprises:

a) amplifying the sequence of interest present within the nucleic acid molecule in a sample by the first or second described method;

b) separating the amplified sequence of interest generated in step (a) from the sample; and c) comparing the sequence obtained in step (b) with a normal sequence thereby detecting the presence of a mutation or polymorphism.

Also disclosed is a method of determining the exonic nucleotide sequence of a gene which comprises determining the nucleotide sequence of the mRNA transcribed by the gene using the fourth described method and deducing the complementary sequence of nucleotide, thereby determining the exonic sequence of the gene.

This method shows promise for population screening of certain genomic diseases because it is a rapid, technically robust, inexpensive, nonisotopic and amenable to automation. Screening may be utilized for any genetic disease amiable to DNA-screening and may be used to test for carriers of these diseases. These diseases include, but are not limited to phenylketonuria, hemophilia, sickle cell anemia and the thalessemias.

In addition, multiple oligonucleotides may be analyzed at one time. This provides a substantial economic benefit because the vast majority of people tested for genetic diseases will produce negative results. This is a qualitative test, that is, there is either an increase in RNA synthesis or there is not. If the base which is specific for the allele is near the 3' end of the PCR primer, the relevant allele will be amplified and can be detected by agarose gel electrophoresis from a mixture of genomic DNA with a 40-fold excess of the other allele. Accordingly, multiple samples may be run without losing the amplification in the background "noise".

Also provided for is a method of detecting mutations in RNA in tissues not accessible to direct analysis which comprises determining the exonic nucleotide sequence of a gene using the method described above and comparing the nucleotide sequence obtained with the normal nucleotide sequence, any difference in the sequence indicating a genomic mutation.

The subject invention has shown (see Experimental Detail) that mRNA for tissue specific proteins is produced at a basal rate in cells not known to express the tissue specific protein. By testing an accessible tissue, biopsy of internal tissues may not be required to test for genomic anomalies present in such diseases a phenylketonuria (PKU) where obtaining a liver sample is not always feasible.

In a preferred embodiment of this method the gene is the Factor IX gene. The factor IX gene is associated with hemophila B. Also provided is a method of determining the predisposition of a subject to hemophilia B, which comprises determining the exonic sequence of the gene using the method described for the factor IX gene and comparing the nucleotide sequence so obtained with normal and known genetic mutants thereby determining the subject's predisposition to the disease.

A further method of this invention is a method of sequencing homologous genes in different species which comprises determining the exonic sequence of the gene of interest using the fourth described method wherein the gene of interest is identified by binding a primer corresponding to a nucleic acid sequence determined in a different species.

The subject invention provides a method of a sequencing a region of a nucleic acid molecule which is adjacent to a known region of a known sequence which comprises:

a) annealing an oligonucleotide containing a promoter to the known region of the nucleic acid molecule;

b) extending the oligonucleotide to the region to be sequenced so that the extension product for primer is complementary to the unknown region of the nucleic acid;

c) isolating the portion of the oligonucleotide extension product which is complementary to the region to be sequenced;

d) treating the oligonucleotide extension product which is complementary to the region to be sequenced so as to add a promoter;

e) transcribing the sequence of the oligonucleotide extension product;

f) treating the transcript so produced so as to prepare a cDNA which is complementary to the transcript; and g) sequencing the cDNA using the fourth described method.

Also provided for is a method of detecting and determining mutations and polymorphisms in the sequence of a nucleic acid which comprises:

a) determining the sequence of the nucleic by the fourth described method; and b) comparing the sequence obtained with that of the normal sequence, known mutations, and polymorphisms.

In addition to the above-identified methods which involve sequencing of nucleic acids to determine if they possess a different sequence, amplified nucleic acids can be analyzed without performing sequencing. For example, electrophoresis and other separation techniques, known to those skilled in the art, can be used to distinguish mutants or polymorphic sequences from normal sequence by virtue of changes in primary, secondary, or tertiary structure.

In one preferred embodiment of this method the mutation is detected in an oncogene. By extending this method, the subject invention provides a method of monitoring the progression of a cancer which comprises detecting and determining mutation and polymorphism in an oncogene using the above-described method and comparing the types of mutation and polymorphism determined with the type of mutation and polymorphism determined at earlier points of time, a change in the types of mutation and polymorphism indicating the progression of the disease.

Another use of this method is in a method of monitoring the efficiency of treatment of a cancer which comprises detecting and determining mutation and polymorphism in an oncogene using the above described method and comparing the type of mutation and polymorphism with the type of mutation and polymorphism determined at earlier points in time, a change in the types of mutation and polymorphism indicating the efficiency of the treatment.

Lastly, the subject invention discloses a method of diagnosing and subtyping infectious agents which comprises:

a) obtaining a sample containing the agent to be analyzed;

b) treating the sample so as to make the nucleic acid molecule to be tested accessible to analysis;

c) determining the nucleotide sequence of the nucleic acid molecule from the infectious agent by the method of described above; and d) comparing the nucleotide sequence obtained with known sequences of nucleotide, thereby diagnosing and subtyping the infectious agents.

EXPERIMENTAL DETAIL

RNA amplification with transcript sequencing (RAWTS) is a rapid and sensitive method of direct sequencing that involves cDNA synthesis, polymerase chain reaction (PCR) with a primer(s) containing a phage promoter, transcription for the phage promoter, and reverse transcriptase mediated sequencing. Each of four tissue specific human mRNAs examined can be sequenced by RAWTS from RNA isolated from each of the four cell types examined (white blood cell, liver, K562 erythroleukemia cells, and chronic villus cells). These results indicate that there is a basal rate of transcription, splicing, and polyadenylation of tissue specific mRNAs in adult and embryonic tissues. In addition to revealing sequence information, it is possible to generate a desired in vitro translation product by incorporating a translation initiation signal into the appropriate PCR primer.

RAWTS can be used to obtain novel mRNA sequence from other species as illustrated with a segment of the catalytic domain of factor IX. Comparison of the sequences indicates that this segment of factor IX evolved at a rate equal to the average of a recent compendium of mammalian proteins [Li, W-H., M. Tanmura, and P. M. Sharp, J. Mol. Evol., 25:330–342 (1987)]. Interestingly, a previously postulated disulfide loop was highly conserved and flanked by nonconserved amino acids. This provides evidence for both the existence of such a disulfide loop in factor IX and for its functional importance.

The ability to obtain mRNA sequences rapidly across species boundaries should aid both the study of protein evolution and the identification of sequences crucial for protein structure and function.

Recently, methods have been described for the direct sequencing of genomic DNA which are based on polymerase chain reaction [Wong, C., C. E. Saiki, R. K. Higuchi, H. A. Erlich, and H. H. Kazazian, Jr., Nature, 330:384–386 (1987); Stoflet, et al., (1988); and Engelke, D. R., P. A.

Hoener, and F. S. Collins, Proc. Natl. Acad. Sci. U.S.A., 85:544–548 (1988)]. One of those methods, known as genomic amplification with transcript sequencing (GAWTS) incorporates a phage promoter sequence into at least one of the PCR primers [Stoflet, E. S., D. D. Koeberl, G. Sarkar, and S. S. Sommer, Science, 239:491–494 (1988)]. GAWTS has been modified to allow RNA to be directly sequenced (FIG. 1).

FIG. 1A shows a schematic of RAWTS. RAWTS consists of four steps: (1) cDNA synthesis with oligo dT or an mRNA-specific oligonucleotide primer (A–B), (2) PCR where one or both oligonucleotide contains a phage promoter attached to a sequence complementary to the region to be amplified (C–D), (3) transcription with a phage promoter (E), and (4) reverse transcriptase mediated dideoxy sequencing of the transcript which is primed with a nested (internal) oligonucleotide (F–G). The incorporation of a phage promoter by PCR has three major advantages: (1) transcription produces a second round of amplification which obviates the need for purification subsequent to PCR, (2) transcription can compensate for suboptimal PCR, and (3) transcription generates a single-stranded template which in routine practice tends to give more reproducible sequence than obtained directly from a linear double-stranded PCR product.

RAWTS is extraordinarily sensitive because it combines the amplification generated by phage transcription with the amplification generated by PCR. Housekeeping mRNAs such as APRT can easily be detected and sequenced with RAWTS from total mRNA from a variety of cell types (data not shown). To determine if tissue specific mRNAs could also be detected, total RNA was isolated from white blood cells, liver, K562 erythroleukemia cells, and cultured chorionic villus cells. The RNA was isolated by lysing the cells in the presence of guanidium-HCl except for the K562 cells where lysis occurred into SDS/proteinase K followed by phenol extraction [Maniatis, T., E. F. Fritsch, and J. Sambrook, in Molecular cloning, Cold Spring Harbor Laboratory, Cold Spring Harbor, N.Y. (1982)]. Single-stranded cDNA was made from total RNA by priming reverse transcriptase with oligo dT [Sarkat, et al. (1988)]. RAWTS was performed on four tissue specific mRNAs: blue pigment (BP) which is expressed in the retina, factor IX (F9) and phenylalanine hydroxylase (PH) which are expressed in the liver, and tyrosine hydroxylase (TH) which is expressed in the brain and adrenal gland.

FIG. 1B shows oligonucleotides for RAWTS of a segment of blue pigment mRNA. Shown are portions of exons 4 and 5 which correspond to the region that was amplified and sequenced. The numbering system of Nathans, et al. [Nathans, J., D. Thomas, and D. S. Hogness, Science, 232:193–202 (1986)] was used. The first PCR was performed with the oligonucleotide primers BP-E4(1230)-16D and BP-(T7-29)E5(1453)-44U (for an explanation of the notation, see below). A 253 bp amplified segment is expected from blue pigment mRNA (224 bp of blue pigment sequence and a 29 bp T7 promoter sequence), and a 1240 bp amplified fragment is expected from genomic DNA. The 253 bp segment was not seen after electrophoresis on a 2.5% agarose gel so the amplified material was diluted 1000-fold and reamplified using BP-E4(1259)-17D and BP-(T7-29)E5 (1453)-44U. The expected 224 bp segment was seen after electrophoresis. An aliquot of the amplified material was transcribed and sequenced by using BP-E4(1293)-17D as the internal primer for reverse transcriptase. This will be further explained in the discussion of FIG. 3.

Since oligonucleotides accumulate rapidly when GAWTS is used, it is important to have informative names. The following nomenclature readily allows the determination of (i) the site of the amplified fragment, (ii) the appropriateness of any combination of oligonucleotides, and (iii) the origin and direction of the sequence generated. It is of the form: G(O)-(I-L)R(C)-SD, where G=gene abbreviation, O=organism, I=identifier(s) for the noncomplementary 5' bases, L=length of the noncomplementary bases, R=region of the gene, C=location of the 5' complementary base, S=total size, and D=5' to 3' direction of the oligonucleotide. The region of the gene (R) is abbreviated by 5', the region upstream of the gene; by E followed by exon number; by. I followed by intron number; or by 3', the region down-stream of the gene. The direction of the oligonucleotide is either U, upstream or D, downstream. If a transcript has been defined, D is the sense direction and U is the anti-sense direction. Otherwise the directions can be arbitrarily defined. Thus BP(Hs)-(T7-29)E5(1453)-44U is an oligonucleotide specific for the blue pigment gene of Homo sapiens which has a T7 promoter (includes a six-base clamping sequence of the 5' end) of 29 base pairs. It is complementary to a sequence in exon 5 that begins at base 1453. The oligonucleotide is a 44 mer, which heads upstream relative to blue pigment messenger RNA. If there is no chance of confusion with other sequences, the designations "BP", "(Hs)", and/or "(T7-29)" can be omitted in routine use. As another example, F9(Hs)-5' (-120)-15D is an oligonucleotide specific for human factor IX. It is complementary to a 15 base sequence 5' to the human factor IX gene that begins at base –120. The oligonucleotide is a 15 mer and the sequence heads downstream relative to in vivo transcription.

Figure 2A:
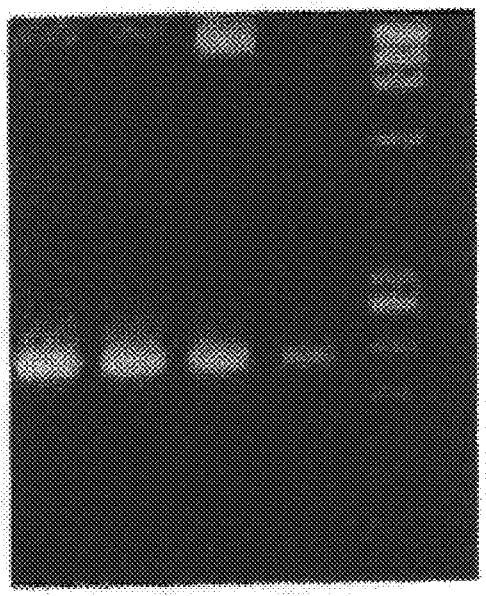
FIG. 2A: Ethidium bromide stain of a 2.5% agarose el subsequent to two rounds of PCR of the blue pigment gene.

FIG. 1B shows how the primers were chosen for the retina-specific blue pigment mRNA. The first set of PCR primers were: BP-(T7-29)E5(1453)-44U which contains the T7 promoter sequence and BP-E4(1230)-16D. The primers chosen span at least one intron so the genomic sequence can be distinguished from that of mRNA. Sequence of the blue pigment mRNA was not obtained from white blood cell RNA even after 40 cycles of PCR. Therefore, a second amplification was performed by diluting an aliquot of the first PCR mix 1,000-fold in a fresh PCR mix and reamplifying with the same T7 promoter oligonucleotide primer along with E4(1259)-17D. An amplified fragment of predicted size was seen (FIG. 2A). The fragment was transcribed and then sequenced by using BP-E4(1293)-17D as the primer for reverse transcriptase. Intronic sequence was absent confirming that mRNA and DNA was the origin of the signal (FIG. 2C). By performing the two rounds of PCR, sequence could also be obtained from liver, K562, and chorionic villus RNA (FIG. 2A, Table 1).

Figure 2B:
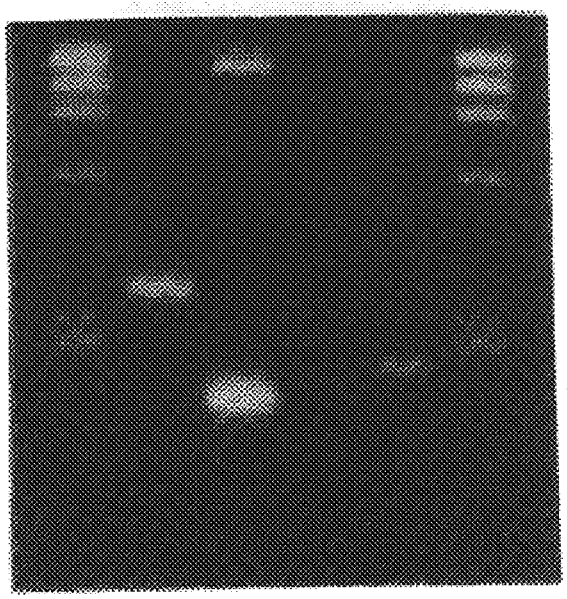
FIG. 2B: Agarose gel of PCR amplification of factor IX, blue pigment, phenylalanine hydroxylase, and tyrosine hydroxylase mRNA from total RNA extracted from blood (lanes F, B, P and T, respectively).
Figure 2C:
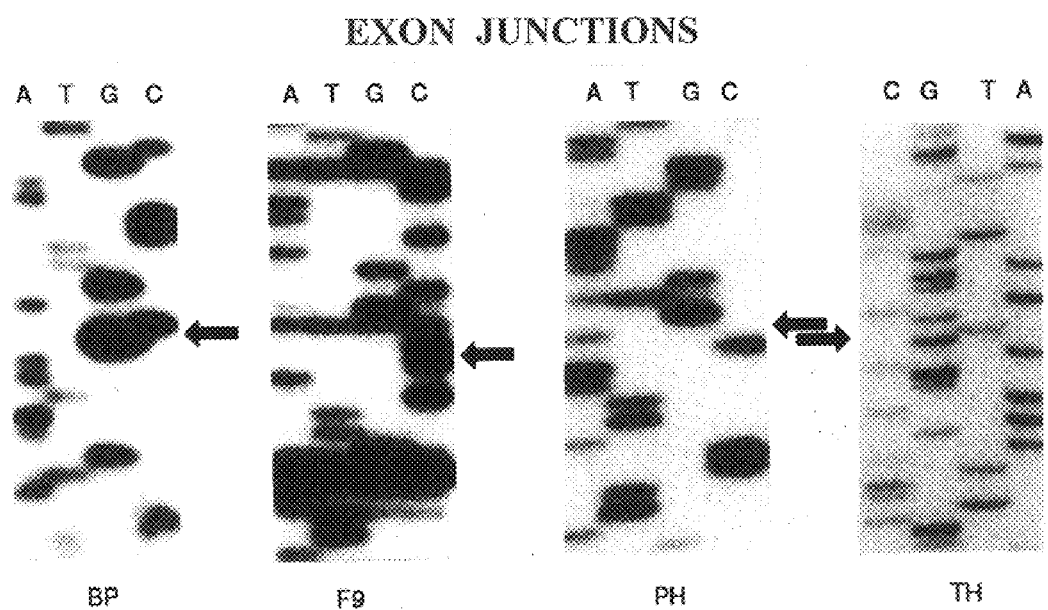
FIG. 2C: Sequence of the exon intron junction of BP, F9 and TH mRNA from blood.

By using either one or more rounds of PCR where one or both primers differed in the second round, the other three tissue specific mRNAs were also sequenced to confirm the absence of introns by using the primers described below (FIG. 2B, 2C and Table 1). Despite the extensive amplification, no sequencing errors were found in 3 kb of sequence (15 combinations of mRNAs and cells at 150–250 bases per combination). This is expected because direct sequencing provides data on a population of molecules rather than a clone of one molecule. So long as multiple mRNA molecules are amplified on the first round of PCR, an error at a specific base during polymerization will not materially affect the predominant sequence of the population of molecules.

TABLE 1

Sequencing of Tissue Specific Human mRNAs

|  |  | Blue Pigment | Factor IX | Phenylalanine hydroxylase | Tyrosine hydroxylase |
|---|---|---|---|---|---|
| T I S S U E | Blood | + | + | + | + |
|  | Liver | + | + | + | + |
|  | K562 | + | + | + | + |
|  | CVS | + | ?* | + | + |

*Factor IX could not be amplified from cultured choronic villus cells but this is most likely a consequence of the partial degradation of this RNA (as indicated by the relative intensity of the 28S and 18S ribosomal RNA species) since the primers utilized for amplification required that more than 2 kb of the mRNA be intact, whereas sequencing of the other mRNAs required that no more than 1.1. kb be intact.

FIG. 2 shows RAWTS of tissue specific mRNA. (A) Ethidium bromide stain of a 2.5% agarose gel subsequent to two rounds of PCR of the blue pigment gene (see FIG. 1B) from 100 ng of total RNA extracted from blood, K562 cells, and liver (lanes B, K, C, and L, respectively). The right most lane shows size standards produced by HaeIII digestion of φX174. (B) Agarose gel of PCR amplification of factor IX, blue pigment, phenylalanine hydroxylase, and tyrosine hydroxylase mRNA from total RNA extracted from blood (Lanes F, B, P, and T, respectively). In some cases, the amplification shown was the result of more than one round of PCR (e.g., see the discussion of FIG. 1B). Each amplified segment spanned an intron. For each gene, the following lists: (i) the source of the numbering system followed by the reference (if different) detailing the position of the introns, (ii) the PCR primers (see above for an explanation of notation), and (iii) the excepted size of the segments of the mRNA and genomic DNA which includes the 29 bp of the T7 promoter. Factor IX (F9)—(i) Yoshitake et al., [Yoshitake, et al. (1985)]; (ii) F9-(T7-29)E7(30057)-46D and F9-E8(31047)-15U; (iii) 351 bp for RNA and 1019 bp for DNA; Blue pigment (BP)—(i) Nathans et al., [Nathans, et al. (1986)]; (ii) PCR 1: BP-E4(1230)-16D and BP-E5 (1453)-44U; PCR 2: BP-E4(1259)-17D and BP-E5(1453)-44U; (iii) For PCR 2, 224 bp for mRNA and 1111 bp for DNA; Phenylalanine hydrozylase (PH)—(i) Kwok et al., [Kwok, et al. (1985)], DiLella et al., [DiLella, et al. (1986)]; (ii) PH-(T7-29)E13(1626)-46U and PH-E12(1420)-16D; (iii) 235 bp for RNA and ca. 1400 bp for DNA; Tyrosine hydroxylase (TH)—(i) Grima et al., [Grima, et al. (1987)], O'Malley et al., [O'Malley, et al. (1987)]; (ii) PCR 1: TH-E8(936)-15D and TH-E13(1507)-15U, after 100,000-fold dilution, PCR 2: TH-(T7-29)E111(1111)-49D and TH-E13(1507)-15U, after 100,000-fold dilution, PCR 3: TH-(T7-29)E11(1111)-49D and TH-E12(1333)-16U, (iii) 251 bp for RNA and 471 bp for DNA.

(c) Sequence of the exon intron junction of BP, F9, and TH, mRNA from blood which verifies that intronic sequence is absent.

Methods

1. RAWTS is a four-step procedure. First strand cDNA synthesis: 20 μl of 50 μg/ml heat denatured total RNA or mRNA, 50 mM Tris-HCl (pH 8.3), 8 mM magnesium chloride, 30 mM KCl, 1 mM DTT, 2 mM each DATP, dCTP, dGTP, dTTP, 50 μg/ml oligo dT 12–18, 10,000 U/ml RNasin, and 1000 U/ml AMV reverse transcriptase were incubated at 42° C. for 1 hr followed by 65° C. for 10 min. Subsequently 30 μl of H$_2$O was added generating a final volume of 50 μl.

2. PCR: 1 μl of the above sample was added to 40 μl of 50 mM KCl, 10 mM Tris-HCl (pH 8.3), 1.0–2.5 mM MgCl$_2$ (empirically determined for each set of primers), 0.01% (w/v) gelatin, 200 μM each NTP, 1 μM of each primer (Perkin Elmer Cetus protocol). After 10 min at 94° C., 1 U of Taq polymerase was added and 40 cycles of PCR were performed (annealing: 2 min at 50° C.; elongation: 3 min at 72° C.; denaturation: 1 min at 94° C.) with the Perkin Elmer Cetus automated thermal cycler. One primer included a T7 promoter as previously described [Stoflet, et al. (1988)].

3. Transcription: After a final 10 min elongation, 3 μl of the amplified material was added to 17 μl of RNA transcription mixture. The final mixture contains: 40 mM Tris HCl pH 7.5, 6 mM MgCl$_2$, 2 mM spermidine, 10 mM sodium chloride, 0.5 mM of the four ribonucleoside triphosphates, RNasin (1.6 U/μl), 10 mM DTT, 10 U of T7 RNA polymerase and diethylpyrocarbonate treated H$_2$O . Samples were incubated for 1 hr at 37° C. and the reaction was stopped by heating at 65° C. for 10 min.

4. Sequencing: 2 μl of the transcription reaction was added to 10 μl of annealing buffer containing the end-labeled reverse transcriptase primer. Annealing and sequencing were performed as previously described in the parent application.

The great sensitivity of PCR can potentially lead to artifact. However, the mRNA sequence that was obtained cannot be due plasmid contamination because, with the exception the factor IX gene, cloned sequences of these genes were not present in the laboratory. Likewise, retina, brain, or adrenal RNA were not present in the laboratory. In addition, contamination of solutions with previously amplified material was routinely monitored by verifying that no segments were seen when PCR was performed without input cDNA. The possibility of processed pseudogenes accounting for the data is eliminated by previously published data [Yoshitake, S., B. G. Schach, D. C. Foster, E. W. Davie, and D. Kurachi, Biochemistry, 24:3736–3750 (1985); Nathans, et al., (1986); Kwok, S. C. M., F. D. Ledley, A. G. DiLella, K. J. H. Robson, and S. L. C. Woo, Biochemistry, 24:556–561 (1985); DiLella, A. G., S. C. M. Kwok, F. D. Ledley, J. Marvit, and S. L. C. Woo, Biochemistry, 25:743–749 (1986); Grima, B., A. Lamouroux, C. Boni, J-F. Julien, F. Javoy-Agid, and J. Mallet, Nature, 326:707–711 (1987);9 O'Malley, K. L., M. J. Anhalt, B. M. Martin, J. R. Kelsoe, S. L. Winfield, and E. I. Ginns, Biochemistry, 26:6910–6914 (1987)] and the results of amplification of genomic DNA for these genes (i.e., no amplified segment is seen at the size expected for mRNA).

In summary, these data indicate that some level of mRNA synthesis occurs for some, if not all, tissue specific genes. Since one round of PCR followed by transcription can amplify a segment one billion-fold, two rounds of PCR should detect mRNAs which are present at very much less than one copy per cell. The levels of these mRNAs in various tissues is of interest, but precise quantitation depends upon: (1) quantitative isolation of RNA which is difficult in tissues with very active ribonuclease such as blood; (2) measurement of the efficiency of cDNA synthesis which depends upon multiple parameters including the concentration of RNA, reverse transcriptase, and primers as well as the particular size and sequence of mRNA of interest; and (3) measurement of the efficiency of PCR, a reaction where small differences in efficiency per cycle are exponentially amplified (work in progress).

The ability to detect basal levels of tissue specific mRNA has certain practical consequences as illustrated with the factor IX gene. First, the exonic sequence for an individual with hemophilia B can be obtained from DNA, but that requires multiple amplifications because the eight exons of the factor IX genes are dispersed over 34 kb of genomic DNA. Given the current limits on the size of efficiently amplified fragments [Saiki, R. K., D. H. Gelfand, S. Stoffel, S. J. Scharf, R. Higuchi, G. T. Horn, K. B. Mullis, and H. A. Erlich, Science, 239:487–491 (1988)], six regions must be amplified and transcribed to sequence the 1,383 base pairs of coding region. In contrast, the entire sequence of the encoding region may well be obtained from RNA with only one amplification and transcription. Second, the consequences of mutations such as the one described at the splice donor junction of intron f [Rees, D. J. G., I. M. Jones, P. A. Handford, S. J. Walter, M. P. Esnouf, K. J. Smith, and G. G. Brownlee, Embo, J. 7:2053–2061 (1988)] may well be delineated with exposing the patient to a liver biopsy a procedure whose hazards cannot generally be justified by a desire to analyze the structure of mRNA.

Figure 3:
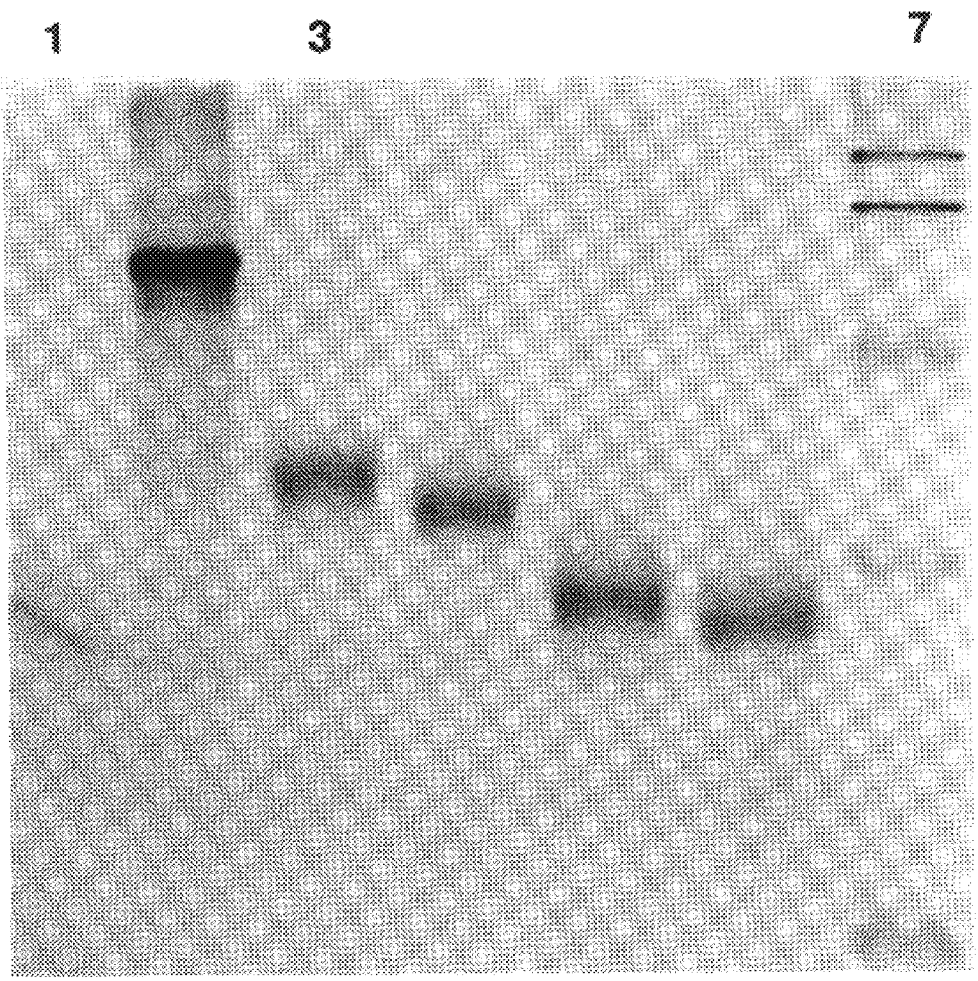
FIG. 3: In vitro translation of segment of factor IX. Lane 1: In vitro translation without an RNA template. Lane 2: In vitro translation product of full-length factor IX mRNA. Lane 3: In vitro translation product derived from a PCR which utilized E6(203365)-51D and E8(31515)-16D. Lanes 4–6: In vitro translation product of a transcript derived from a PCR which utilized E6(20365)-51D plus E8(31215)-16U and E8(31189)-16U, respectively. Lane 7: protein size markers (Amersham) 92.5, 69, 46, 30, 14.3 kd, respectively.

Once an mRNA segment has been amplified distal to a phage promoter, it is also possible to obtain the protein product by in vitro translation or by insertion into an appropriate expression vector. For factor IX, the carboxy terminal 287 amino acids encoded by exons f through h were made by RNA amplification with in vitro translation (RAWIT). An eight nucleotide translation initiation signal [CCACCATG [Koza, M., Mol. Cell. Biol., 8:2737–2744 (1988)]] was added 3' to the T7 promoter sequence of the PCR primer. When the PCR product was transcribed in the presence of 7mGpppG [Pelletier, J., and N. Sonnenberg, Cell, 40:515–526 (1985)], a capped RNA was generated which contained a predicted 5' untranslated leader of only 11 bases ad a 3' untranslated region of 146 bases. The capped RNA specifically produced a peptide of expected size in both a reticulocyte (FIG. 3) and a wheat germ (data not shown) lysate [Pelletier, et al., (1985)]. RAWIT performed with alternate PCR primers yielded similar amounts of peptides of predicted size despite the absence of a termination codon as well as all 3' untranslated sequences (FIG. 3). The ability to produce a desired segment of a protein rapidly by RAWIT should facilitate the delineation of relationships between structure and function.

FIG. 3 shows in vitro translation of segments of factor IX. E5(20365)-51D [full name: F9(Hs)-T7/TI-37 E5(20365)-51D] has a sequence GGATCCTAATACGACT-CACTATAGGGAGA CCACCATG CCATTTCCATGTGG. It contains a 29 base T7 promoter sequence followed by a 9 base translation initiation signal and a 14 base sequence complementary to exon f. PCR was performed with E5(20365)-51D and one of four additional oligonucleotides. The transcript produced by T7 contains an 11 nucleotide leader (GGGAGACCACC) followed by the initiating ATG in frame with the coding sequence.

Lane 1: in vitro translation without an RNA template.
Lane 2: in vitro translation product of full-length factor IX mRNA.
Lane 3: in vitro translation product the transcript derived from a PCR which utilized E6(203365)-51D and E8(31515)-16D. The transcript produced with T7 RNA polymerase codes for an 11 base 5' untranslated region, a 288 amino acid peptide of predicted molecular weight 31,486 d and 1 146 base 3' untranslated segment.
Lanes 4–6: in vitro translation product of a transcript derived from a PCR which utilized E6(20365)-51D plus E8(31330)-16U, E8(31215)-16U, and E8(31189)-16U, respectively. The predicted molecular weights of the peptides are 28,785, 25,872, and 25,124 d, respectively.
Lane 7: protein size markers (Amersham): 92.5, 69, 46, 30, and 14.3 kd, respectively.

For each in vitro translation, the peptide of predicted size was seen.

In addition to sequencing and translating mRNA from different tissues, it would be useful to rapidly determining mRNA sequence in other species. The human factor IX PCR primers (T7-29)E7(30057)-46D and E8(31048)-15U were used to amplify cDNA derived from mouse and rat liver mRNA. A series of amplifications were performed with increasing amounts of magnesium in order to decrease the stringency of annealing. Segments of the expected size were seen at 5 mM $MgCl_2$ in both mouse and rat. Attempts to sequence the rodent fragments by using the internal human oligonucleotide were unsuccessful. However, the PCR primer could be used to generate a sequence, albeit of low quality. From this sequence, a mouse-specific oligonucleotide was designed and resequencing of the transcript with this primer have high quality sequence for both mouse and rat (FIG. 4). By using an alternate pair of PCR primers, it was possible to obtain high quality sequence for guinea pig, rabbit, and sheep (FIG. 4). A comparison of nucleotide and amino acid sequence indicates that this segment of the catalytic domain of factor IX has evolved at approximately an average rate [Li, et al., (1987)]. However, the loop of amino acids formed by a postulated disulfide bond at $Cys^{206}$ and $Cys^{222}$ [Yoshitake, et al., (1985)] is highly conserved. Since $His^{221}$ is known to participate in the catalytic reaction [Yoshitake, et al., (1985)], this loop is most likely important for the formation of the active site.

FIG. 4 shows cross-species sequencing with RAWTS (ZooRAWTS). Novel nucleotide and amino acid sequence of amino acids 201–260 of the factor IX gene of mouse, rat, guinea pig, rabbit, and sheep were obtained by performing RAWTS on mRNA from liver. cDNA was generated with oligo dT (see the above description of FIG. 2), and then PCR was performed under low stringency (increased magnesium concentration) with the human primers (T/-29)E7(30057)-46D and E8(31048)-15U. An amplified segment of expected size was obtained from mouse and rat liver cDNA sequence was obtained by using E8(31048)-15U as the primer for reverse transcriptase, but the use of a PCR primer for sequencing did not produce data of uniformly high quality. From that data, an oligonucleotide complementary to both mouse and rat factor IX was synthesized and then utilized as a nested sequencing primer. This resulted in sequence data without any ambiguities. For guinea pig, rabbit, and sheep, a different pair of human primers was used to obtain the initial sequence. Then a sheep specific primer was synthesized and successfully utilized to obtain sequence data from the three species. The previously determined amino acid sequence of the corresponding region of bovine factor IX is included for completeness [Katayama, K., L. H. Ericsson, D. L. Enfield, K. A. Walsh, H. Neurath, E. W. Davie, and K. Titani, Proc. Natl. Acad. Sci. USA, 76:4990–4994 (1979)].

Sequence from multiple species is helpful in interpreting changes found in hemophiliacs. As examples, $Cys^{222}$ and $Asn^{260}$ are conserved in all species examined, providing further evidence that the substitutions at these positions found in a severe hemophiliac (factor IX coagulation=1%), and a mild hemophiliac (factor IX coagulant=24%), respectively, represent the causative mutations rather than rare polymorphisms.

In summary, incorporation of a phage promoter into a PCR oligonucleotide primer allows an abundance of transcript to be made after amplification of mRNA by PCR. The sensitivity of the technique allow tissue specific mRNAs to be sequenced from most if not all tissues and the conservation of sequence through evolution allows mRNAs from other species to be sequenced without cloning. In addition, the transcript can be translated in vitro, thereby allowing the intact protein or any desired segment to be produced.

The subject invention further concerns a PCR-based sequencing method called genomic amplification with transcript sequencing (GAWTS) which bypasses cloning and increases the rate of sequence acquisition by at least fivefold. The method involves the attachment of a phage promoter onto at least one of the PCR primers. The segments amplified by PCR are transcribed to further increase the signal and to provide an abundance of single-stranded template for reverse transcriptase mediated dideoxy sequencing. An end-labeled reverse transcriptase primer complementary to the desired sequence generates the additional specificity required to generate unambiguous sequence data.

GAWTS can be performed on as little as one nanogram of genomic DNA. The rate of GAWTS can be increased by coamplification and cotranscription of multiple regions as illustrated by two regions of the factor IX gene.

Since GAWTS lends itself well to automation, further increase in the rate of sequence acquisition can be expected. Further, commercial applications of GAWTS include: (1) the generation of a kit to assist others utilize the technique; (2) the generation of an instrument that automates the method; and (3) the generation of diagnostic tests that utilize the method.

In contrast to autosomal recessive mutations, deleterious X-linked mutations are eliminated within a few generations because the affected males reproduce sparingly if at all. Thus, each family in an X-linked disease such as hemophilia B represents an independent mutation. From the perspective of efforts to understand the expression, processing, and function of factor IX, this is useful since a large number of mutations are potentially available for analysis. In addition to facilitating structure-function correlations, the rapidity of GAWTS makes it practical to perform direct carrier testing and prenatal diagnosis of at risk individuals. By amplifying and sequencing 11 regions of the hemophilic factor IX gene which total 2.8 kb, it should be possible to delineate the causative mutation in the overwhelming majority of individuals as these regions contain the putative promoter, the 5' untranslated region, the amino acid coding sequences, the terminal portion of the 3' untranslated region, and the intron-exon boundaries. Once the mutation is delineated, GAWTS can be used to directly test an at-risk individual, thereby finessing the multiple problems associated with indirect linkage analysis.

Figure 5:
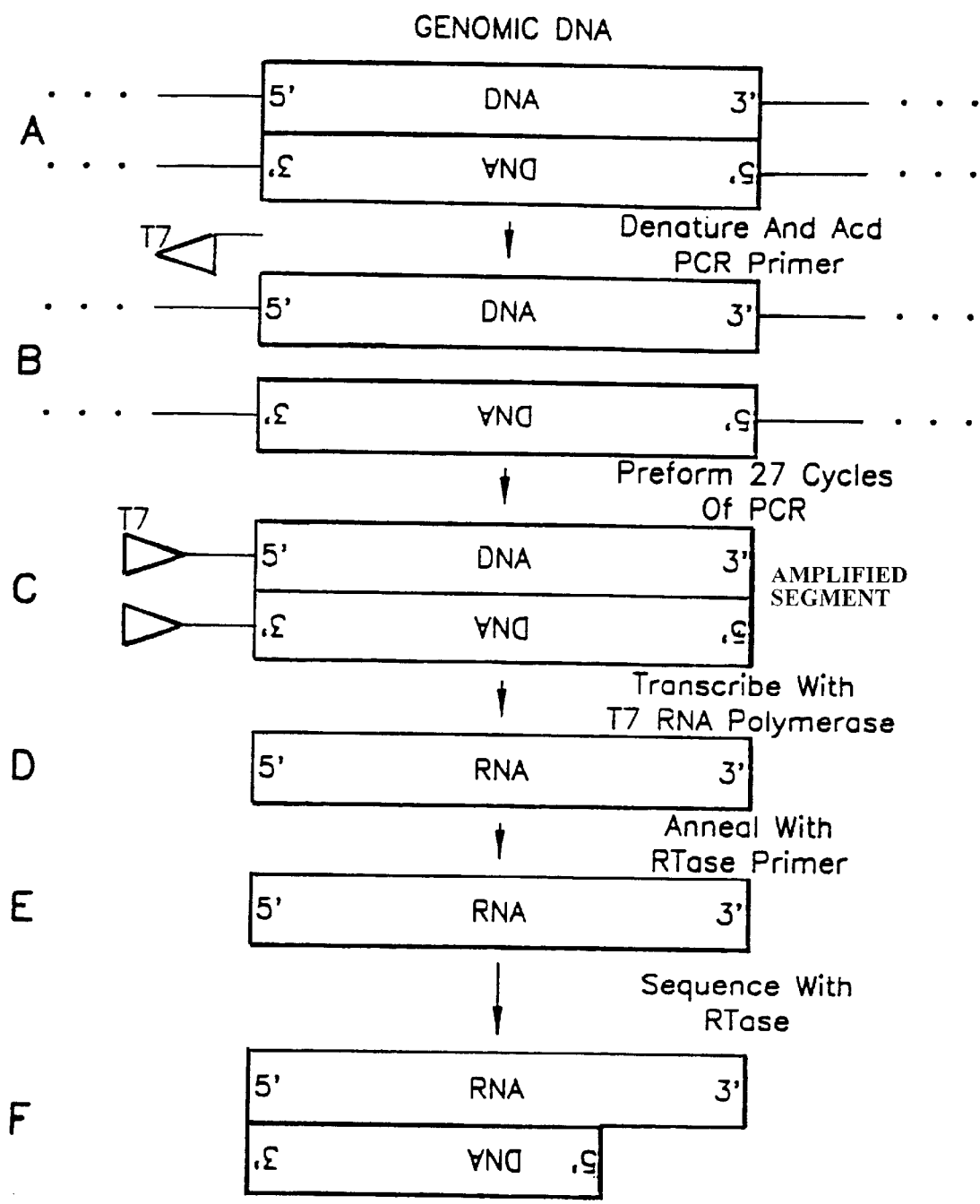
FIG. 5: A diagrammatic representation of the amplification and direct sequencing method of the present invention.

GAWTS depends on two types of sequence amplification and a total of three oligonucleotides to generate the needed specificity (see FIG. 5). The steps of GAWTS as shown in FIG. 5 are as follows:

A. The region of genomic DNA to be amplified is indicated by the open rectangle. Two strands with their 5' to 3' orientation are shown. The darkened regions represent flanking sequences.

B. The oligonucleotides anneal to sites just outside the sequence to be amplified. One of the oligonucleotides has a 29 base T7 promoter sequence.

C. PCR consists of repetitive cycles of denaturation, annealing with primers, and DNA polymerization. Since the number of fragments with defined ends increases much faster than the number with undefined ends, virtually all the fragments are of defined size after 27 cycles. However, since the oligonucleotides anneal to other sites in the genome, multiple spurious fragments are also amplified. The segment pictured is a specifically amplified sequence.

D. RNA is transcribed from the T7 promoter. This provides a convenient source of single-stranded nucleic acid for dideoxy sequencing.

E. Due to the complexity of the mammalian genome, the amplified and transcribed sequences contain other genomic segments whose flanking sequences cross-hybridize with the PCR primers at the stringency generated by the DNA polymerization reaction. As a result, another level of specificity is crucial to obtaining interpretable sequences. That specificity is provided by utilizing an oligonucleotide primer for reverse transcriptase which lies in the region of interest.

F. Reverse transcriptase is used to generate sequence data by the dideoxy method.

The first region chosen for amplification was part of the amino acid coding region of exon 8 of the factor IX gene. FIG. 6 shows the relevant sequence and indicates the locations of the PCR primers ana the reverse transcriptase primer. Primers are named using the numbering scheme in Yoshitake et al., Biochemistry, 24: 3736 (1985).

A. Oligonucleotides Synthesized (Synthetic Genetics, Inc.) for GAWTS of a Region in the Proximal Part of Exon 8.

The PCR primers are (T7-29)-E8(30884)-48D and (PST1-9)E8(31048)-27U and the reverse transcriptase primer is E8(31025)-17U. The noncomplementary bases in E8(31048)-27U may be ignored as they are not relevant to this series of experiments. Note that by replacing these bases with a different phage promoter, it should be possible to generate an amplified fragment where both strands could be selectively transcribed and sequenced.

Since oligonucleotides tend to rapidly accumulate when using GAWTS, it is helpful to have informative names. The notation used above is one of the form: (identifier for noncomplementary 5' base-length) region of the gene (location of the 5' complementary base using the numbering system of Yoshitake et al., supra)—total size and 5' to 3' direction of the oligonucleotide. The region of the gene can be abbreviated by Upstream, Exon number, Intron number, and Downstream. The direction of the oligonucleotide is either Upstream or Downstream relative to the direction of the transcription. Thus, (T7-29) E8(30884)-48D has a T7 promoter (plus a 6 base clamping sequence) of 29 bases. It is complimentary to a sequence that in exon 8 begins at base 30884. The oligonucleotide is a 48 mer which heads downstream relative to E9 mRNA. E8(310 25)-17U is also located in exon 8, lacks a 5' non-complementary sequence and begins at 31025. It is a 17 mer that heads upstream. Likewise, U (-140)-16U is a 16 mer located upstream of the gene which begins at base -140 and heads further upstream of the gene.

B. GAWTS for Exon 8 of the Factor IX Gene Utilizing the Primers Pictured in FIG. 6.

1. Method: The PCR, transcription, and sequencing reaction were performed as previously described with minor modifications. [See R. K. Saiki, et al., Nature, 324: 163 (1986); D. A. Melton, et al., Nucleic Acids Res. 12: 7035 (1984); J. Geliebter, Focus, 9: (1)5–8 (1987)]. In brief, a microfuge tube containing 1 μg (10 ng/μl) of DNA was denatured at 95° C. for 10 min (2 min in subsequent cycles) in the presence of the following: 50 mM sodium chloride, 10 mM Tris-HCl pH 7.6, 10 mM magnesium chloride, 10% DMSO, and 1.5 mM of each of the four deoxynucleotide triphosphates. After microfuging, samples were then annealed at 50° C. for 2 min and subsequently one-half unit of Klenow fragment was added. Samples were incubated at 50° C. for another 2 min. Twenty-six additional cycles of denaturation, annealing, and polymerization were performed.

It is crucial to assure that the Klenow fragment added at later cycles has the same activity as that added at early cycles. To this end, fresh aliquots of Klenow fragments were removed from the −20° C. freezer every seven cycles and diluted from the manufacturer buffer to 10 µl/l with dilution buffer (10 mM Tris pH 7.5, 1 mM DTT, 0.1 mM EDTA, and 1.5 mM of the four deoxytriphosphates).

After a final denaturation, 3 µl of the amplified material was added to 17 µl of the RNA transcription mixture: 40 mM Tris-HCl pH 7.5, 6 mM magnesium chloride, 2 mM spermidine, 10 mM sodium chloride, 0.5 mM of the four ribonucleotide triphosphates, 1.6 U/µl RNAsin, 10 mM DTT, 10 U T7 RNA polymerase, and DEPC treated $H_2O$. Samples were incubated for 1 hr at 37° C. and the reaction was stopped with 5 mM EDTA.

For sequencing, 2 µl of the transcription reaction and 1 µl of the $^{32}P$ end labeled (see below) reverse transcriptase primer were added to 10 µl of annealing buffer (250 mM KCl, 10 mM Tris-HCl pH 8.3). The samples were heated at 80° C. for 3 min (Tris-HCl pH 8.3). The samples were heated at 80° C. for 3 min and then annealed for 45 min at 45° C. (approximately 5° C. below the denaturation temperature of the oligonucleotide). Microfuge tubes were labeled with A, C, G, and T. The following was added: 3.3 µl reverse transcriptase buffer (24 mM Tris-HCl pH 8.3, 16 mM magnesium chloride, 8 mM DTT, 0.4 mM dATP, 0.4 mM dCTP, 0.8 mM dGTP, and 0.4 mM dTTP) containing 5 U of AMV reverse transcriptase, 1 µl of either 1 mM ddATP, or 1 mM ddCTP, or 1 mM ddGTP, or 2 mM ddTTP and finally, 2 ul of the primer RNA template solution. The sample was incubated at 50° C. for 45 min and the reaction was stopped by adding 2.5 µl of 100% formamide with 0.3% bromophenol blue and xylene cyanol FF. Samples were boiled for 3 min and 3 µl were loaded onto a 100 cm sequencing gel and electrophoresed for about 15,000 V-h. Subsequently, autoradiography was performed, utilizing known techniques.

End-labeling of the reverse transcriptase primer was performed by incubating a 0.1 µg sample of oligonucleotide in a 13 µl volume containing 50 mM Tris-HC1 (ph 7.4), 10 mM $MgCl_2$, 5 mM DTT, 0.1 mM spermidine, 100 µCi [$^{32}P$] ATP (5,000 Ci/mmole) and seven units of polynucleotide kinase for 30 min at 37° C. The reaction is heated to 65° C. for 5 min and 7 µl of water was added for a final concentration of 5 ng/µl of oligonucleotide. One µl of labeled oligonucleotide was added per sequencing reaction without removal of the unicorporated mononucleotide.

Figure 7A:
FIG. 7A: Agarose gel after 27 cycles of polymerase chain reaction.
Figure 7B:
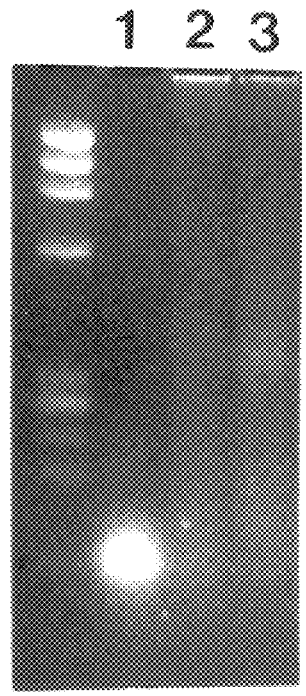
FIG. 7B: Subsequent transcription reaction in accordance with the present invention.

GAWTS for exon 8 of factor IX gene was evaluated as shown in FIG. 7 for lane 1, 40 picograms (1 picogram of sequence to be amplified) of pSP6-9A, a plasmid containing factor IX cDNA, was the input DNA. For reactions 2 and 3, 1 µg of genomic DNA from a normal and hemophiliac individual, respectively, was the input dNA. (A) 3% NuSieve/1% Seakem agarose (FMC) gel of 30% of the PCR amplified material. (B) 3% NuSieve/1% Seakem agarose gel of the transcribed material. The unlabeled lanes contain a HaeIII digest of PSFX174 as size markers. (C) Autoradiogram of segment of the sequencing gel. From left to right, the order of the lanes are ATCG. In set 3, there appears to be an extra "A" at position 2 but review of the original autoradiograph clearly indicates that this is artifact.

2. Results: FIG. 7 shows an agarose gel after 27 cycles of polymerase-chain reaction (7A) and the subsequent transcription reaction (7B). In sample 1, the input DNA was 40 picograms of pSP6-9A, a 6.5 kb plasmid containing factor IX cDNA which was kindly provided by Dr. C. Shoemaker of *Genetics Institute Inc*. The total amount of the region to be amplified is approximately 1 picogram. As FIG. 7A (lane 1) shows, there was a discrete amplified fragment (predicted size: 209 bp) which migrated as expected relative to the size markers. From the intensity of ethidium bromide fluorescence relative to known size standards, it is estimated that a 500,000 fold amplification had occurred.

Amplified material (25 mg) was transcribed with T7 RNA polymerase resulting approximately 10 µg of transcript (3B). Ten percent of the transcribed material was then added to a reverse transcriptase sequencing reaction. Perfect agreement with the published sequence was obtained.

Figure 7C:
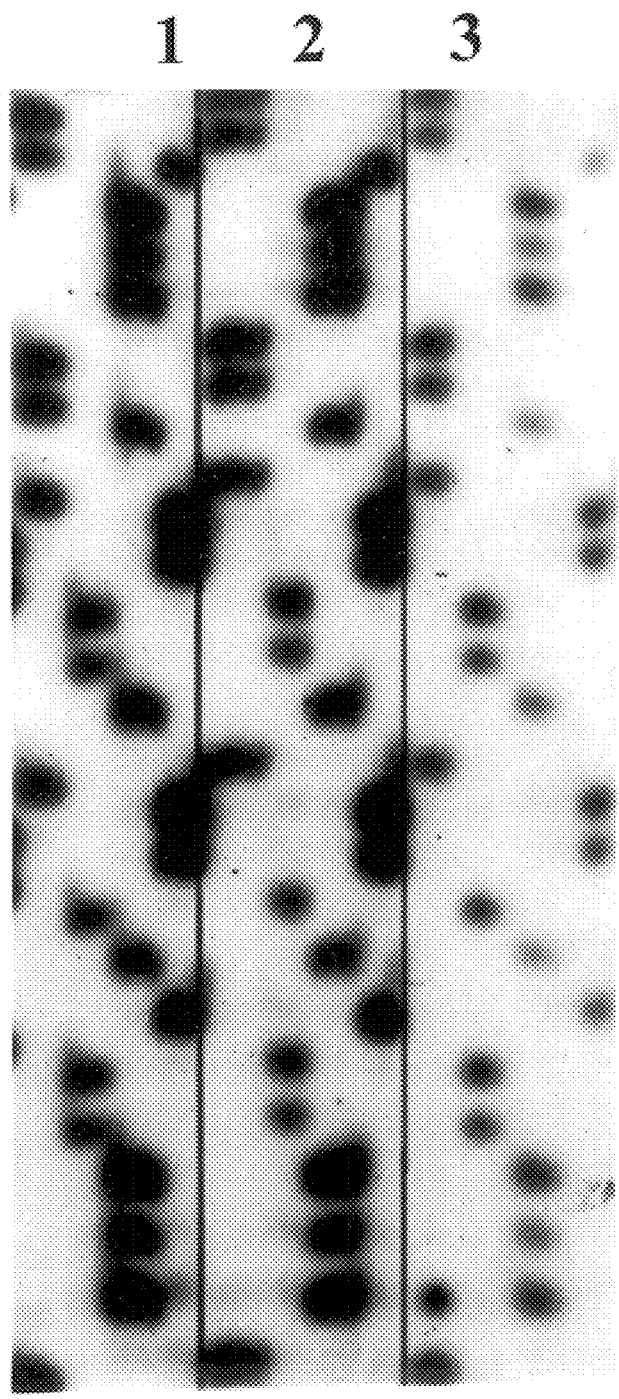
FIG. 7C: Autoradiogram of a segment of sequencing gel in accordance with the present invention.

In sample 2, the input was 1 µg of genomic DNA from a normal individual and, in sample 3, the input was 1 µg of DNA from an individual with hemophilia B. Although spurious amplification masks the expected band, the specificity conferred by the reverse transcriptase primer allowed unambiguous sequence determination (FIG. 7C). No sequence alterations were seen in the 115 bases of sequence which lie between the reverse transcriptase primer and the 48 base polymerase chain reaction primer.

This region was examined for an additional 38 males (6 with hemophilia B and 32 unaffected individuals from a variety of ethnic groups) and no sequence alterations were seen.

To test the sensitivity of GAWTS, the amount of genomic DNA was incrementally decreased. With the aid of an intensifying screen, a sequence could be discerned with 1 ng of input DNA (the amount of DNA contained in 150 diploid cells). At this level, PCR is possible in a crude cell lysate. (R. K. Saiki et al., supra).

As a test of the generality of the procedure, an attempt was made to amplify four additional regions of the factor IX gene: (1) a 332 bp sequence which includes the putative promoter region, exon 1, and the splice donor junction of intron 1; (2) a 315 bp region that includes exon 6 and the flanking splice junctions; (3) a 331 bp region in the amino acid coding region of exon 8; and (4) a 250 bp region that contains the distal 3' untranslated region of exon 8. In three of the four regions, the amplified regions had a band of expected size that was discernable above the background of nonspecific amplification and transcription on an agarose gel. Although the intensity of the signal varied, the four regions all produced unambiguous sequence data. Unlike previous methods which involved cloning of single molecules from a mixture, the error rate of GAWTS in relatively unaffected by the fidelity of polymerization because the sequence obtained is the dominant sequence in the population.

No point mutations or new polymorphisms were found in the normal and hemophilic individuals analyzed by GAWTS for the regions mentioned above. However, the previously documented polymorphism in amino acid 148 in exon 6 was detected.

C. GAWTS with Simultaneous Amplification and Transcription of a 331 bp Region (Region I) in the Amino Acid Coding Segment of Exon 8, and a 250 bp Region (Region II) which begins 1.2 kb Downstream in Exon 8.

To determine whether more than one region could be simultaneously amplified with PCR and transcribed, the 331 bp region in the amino acid coding region of exon 8 and the 250 bp region in the distal 3' untranslated region of exon 8 were utilized. Both sequences could be obtained with the appropriate reverse transcriptase primer.

Figure 8:
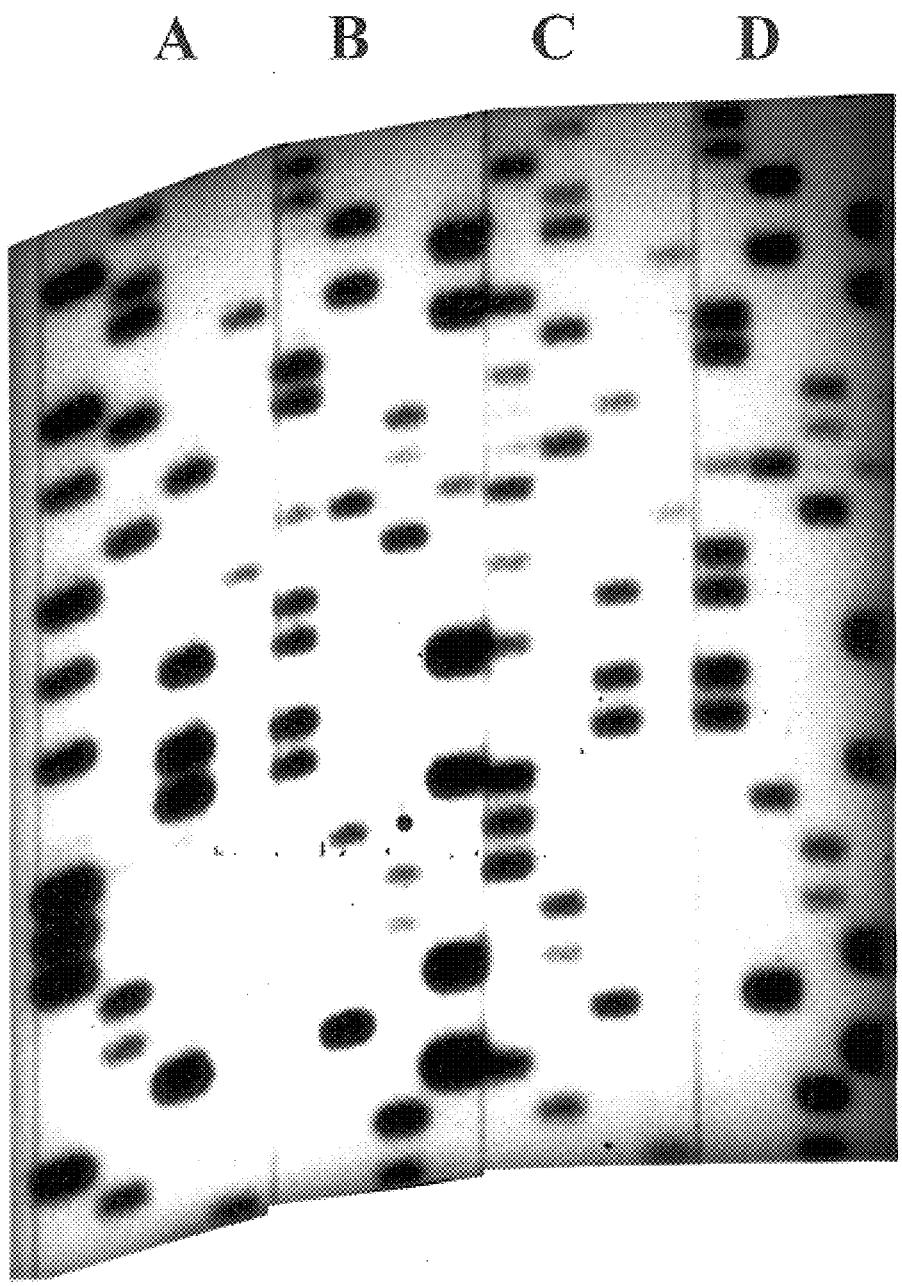
FIG. 8: Results of genomic amplification with direct sequencing with simultaneous amplification and transcription of a 331 bp region in the amino acid coding segment of exon 8, and a 250 bp region which begins 1.2 kb downstream in exon 8.

PCR and transcription reactions were performed on 1 µg of DNA with: (1) primers specific for Region I, (2) primers specific for region II, and (3) both sets of primers. Sequencing was performed as follows: (A) template from PCR/transcription reaction (1) with reverse transcriptase primer specific for Region I, (B) template from PCR/transcription reaction (2) with reverse transcriptase primer specific for Region II, (C) template from PCR/transcription reaction (3) with reverse transcriptase primer specific for Region I, and (D) template from PCR/transcription reaction (3) with reverse transcriptase primer for Region II. As seen in FIG. 8 the order of the lanes are ATGC.

Simultaneous amplification was also successful for a second pair of regions suggesting that it can further enhance the rate of sequence acquisition while decreasing the cost of sample processing.

The oligonucleotides utilized above were synthesized by the phosphoramidite chemistry and subsequently gel purified. Purification is not always necessary because crude (T7-29)E8(30884)-48D, a 48 mer, gave an acceptable sequence despite the fact that gel staining indicated that less than 50% of the molecules were of the desired length.

GAWTS substantially reduces the time required to sequence an allele as eight samples can be amplified, transcribed and loaded onto a sequencing gel in an eight to nine hour day. Thus, in a span of less than two years, the rate of detection of changes in genomic sequence has increased by a factor of about 100. As a result, an array of experiments are now feasible in a diversity of fields. As there are no centrifugations, ethanol precipitations, or complicated procedures such as plaque lifts, GAWTS lends itself well to automation. With modifications of an automated PCR instrument, [R. K. Saiki, et al., Nature, 324:163 (1986)] and an automated sequencer, [L. M. Smith, et al., Nature, 321:674 (1986)], it should be possible to generate a fully automated system.

As the sophistication of the component instruments increases, it is conceivable that the rate of genomic information retrieval could be further increased by orders of magnitude. This has broad implications for both research and clinical medicine. As one example, most DNA-based analyses of tumors currently utilize easily detectable mutations such as gene amplifications and chromosome rearrangements. If it becomes possible to rapidly sequence the promoter region, exons, and splice junctions of multiple oncogenes in neoplasms, it should be possible to obtain a much more comprehensive view of the genetic alterations that accompany malignancy. The insights gained may well aid the clinician in determining prognosis and optimizing therapy.

It is to be understood that the GAWTS method described herein can be adopted by one of skill in the art to provide kits to assist others utilize the technique. Also diagnostic tests that utilize the method are envisioned. One example of a kit incorporating the method of the present invention is designed to rapidly and specifically amplify nucleic acid and produce a transcript of the nucleic acid. Kit components include chain reaction oligonucleotide primers for hybridizing to each end of a nucleic acid sequence with at least one of said primers including a promoter sequence and components for amplifying said nucleic acid sequence.

While GAWTS as described herein is used to sequence gene fragments the present invention is more broadly directed to a rapid and sensitive method of amplification of nucleic acid sequences to provide for subsequent production of RNA transcript. This involves hybridizing oligonucleotide primers to each end of a nucleic acid sequence with at least one of the primers including a promoter sequence; and amplifying the sequence with methods such as polymerase chain reaction. Subsequent generation of an mRNA transcript and sequencing of the transcript can then be conducted in accordance with the present invention. Accordingly, the nucleic acid to be amplified can be RNA or DNA.

The sensitivity of GAWTS allows the diagnosis of infectious agents including viruses such as the HIV virus, bacteria such as gonnococus mycobacterium and mycoplasma, and eukaryotes agents such as fungi and parasites. The sequence data will facilitate the study of the epidemiology of these agents.

The sensitivity of GAWTS can be increased by performing a number of cycles of PCR with one pair of primers and then performing subsequent cycles of PCR with one pair of primers and then performing subsequent cycles with a nested pair of primers complementary to sequences internal to the initial primer pair. Multiple rounds of nested PCR are possible. Applications to in situ detection of nucleic acid sequences are possible.

Many further extensions and enhancements can be envisioned. Two of particular interest involve the amplification of RNA such as messenger RNA discussed hereinabove. cDNA can be made by established protocols. [J. Geliebter, Focus, 9:5 (1987)]. Then the cDNA can be amplified and sequenced as described above. Alternately, the amplified cDNA can be used for other purposes such as insertion into an expression vector or transcription followed by in vitro translation.

Previously undefined genomic sequence at the junction of a defined sequence can be obtained by a number of variations of GAWTS including the following:

1. annealing under nonstringent conditions with a specific oligonucleotide containing a promoter such as T7 (oligonucleotide A), and extending with a polymerase;
2. Elimination of the primer by a method such as ultrafilteration or gel electrophoresis;
3. Denaturation and annealing under nonstringent conditions with an oligonucleotide (oligonucleotide B) which an be enlongated with a polymerase;
4. Removal of oligonucleotide B (length of oligonucleotide B=approximately 16 nucleotides);
5. Addition of oligonucleotide B fused with a different promoter (such as T3) (oligonucleotide C), and oligonucleotide A;
6. Transcription;
7. DNAse treatment;
8. Inactivation of DNAse;
9. Production of cDNA using oligonucleotide C and oligonucleotide D which anneals three primers to the known sequence that oligonucleotide A anneals to;
10. Amplification of cDNA with PCR;
11. Transcription using the second (T3) promoter; and
12. Sequencing with reverse, transcriptase using oligonucleotide E which anneals 3 to the site of annealing of oligonucleotide D.

GAWTS is a method of direct sequencing which involves amplification with PCR using primers containing phage promoters, transcription of the amplified product, and sequencing with reverse transcriptase [Stoflet, E. S., D. D. Koeberl, G. Sarkar, and S. S. Sommer, Science, 239:491–494 (1988)] GAWTS requires a knowledge the sequence directly adjacent to the region to be sequenced.

MODIFICATIONS OF RAWTS AND GAWTS

Many alternate embodiments can be envisioned to the methodology described above. The following are some examples:

1. The amplified RNA can be analyzed for sequence variation without necessarily performing sequencing. Electrophoresis and other separation techniques can be used to distinguish mutants or polymorphic sequences from the normal sequence by virtue of changes in primary, secondary, or tertiary structure.
2. The primers can be any molecule that primes a polymerase. Ribonucleotides or nucleotides not found in nature can be used. So long as primer a polymerase is possible, molecules other than nucleotides could suffice.
3. PCR could be performed by polymerizing RNA or some nucleotide analogues rather than by polymerizing DNA.
4. PCR or its modifications are not crucial for the amplification. For example, a DNA polymerase such as Q-β replicase can conceivably substitute for PCR if it could be adapted to contain a promoter sequence. As long as amplification and transcription can be performed, the invention and its variation such as GAWTS and RAWTS, etc., can be performed. Transcription is sometimes defined as the formation of an RNA from a template such as DNA or double-stranded RNA. In a broader fashion, it can be viewed as a process that catalytically generates a single-stranded nucleic acid or nucleic acid analog where initiation of the process requires a recognition sequence (promoter) rather than extension of a primer sequence.
5. Sequence need not be generated by reverse transcriptase. Any method of generating sequence from the amplified RNA could be used.

The subject invention also provides promoter ligation and transcript sequencing (PLATS), a direct method for rapidly obtaining novel sequences from clones. PLATS involves restriction digestion of the amplified vector insert, ligation with a phage promoter, and then GAWTS using phage promoter sequences as the PCR primers. PLATS is rapid and economical because it uses a limited set of generic oligonucleotides, and is potentially amenable to automation because it does not require in vivo manipulations. PLATS has been applied to the sequencing of a 1.1 kb clone from the fungus, *Achlya ambisexualis*. The sequence reveals a large, transcribed open reading frame which is markedly deficient in the dinucleotide, TpA. A putative zinc finger and an acidic segment hint that Aa1.1 may be a member of a novel class of transcriptional regulators.

Materials and Methods

The plasmid pXER4.4 containing the Xenopus estrogen receptor cDNA was obtained from David Shapiro [Weiler, I. J., D. Lew, and D. J. Shapiro, Mol. Endo., 1:355–362 (1987)], and the SPA plasmid containing the chicken estrogen receptor cDNA was obtained from Bert O'Malley [Maxwell, B. L., D. P. McDonnell, O. R. Connelly, T. Z. Schulz, G. L. Green, and B. W. O'Malley, Mol. Endo. 1:25–35 (1987)]. The stock solutions of 20×SSPE buffer, SM buffer, LB media, and Denhardt's solution were prepared as described previously [Maniatis, T., E. F. Fritsch, and J. Sambrook, Molecular Cloning: A laboratory manual. Cold Spring Harbor Laboratory, Cold Spring Harbor, N.Y. (1982)]. The Sequenase DNA sequencing kit (United States Biochemical) was used for M13 subclone sequencing with α-$^{35}$S-DATP (Amersham).

The oligonucleotides for PCR were designed to give a $T_m$ of 48°–50° C. under standard conditions (1M NaCl) as estimated by the formula $T_m$=4° C.×(number of guanines and cytosines)+2° C.×(number of adenines and thymines) [Meinkoth, J. and G. Wahl, al. Biochem 138:267–284 (1984)]. All oligonucleotides used in these experiments are shown in Table 2.

Double stranded promoters (for review, see [Chamberlin, T. and T. Ryan In boyer, P. D. (ed), The Enzymes, Academic Press, New York, N.Y., Vol. XV, pp. 87–108]) were prepared for ligation by synthesizing two oligonucleotides: the first contained a 3 base clamping sequence, such as CTT, followed by the 23 base sequence of the SP6 RNA polymerase promoter (e.g. SP6-26, see Table 2), and the second contained the 23 base anti-sense sequence (e.g. SP6-23). Three nmoles (approx. 24 μg) of each oligonucleotide were mixed in 1 ml of 10 mM Tris pH 7.4, 5 mM NaCl, and 1 mM EDTA, heated to 80° C. for 10 min, and cooled to 25° C. over 1 hr. These annealed promoters, at a final concentration of 3 pmole/ml, shall be referred to as apSP6, apT7, or apT3.

TABLE 2

Primers for Sequencing termini of inserts into Lambda gt10[1]

A. PCR primers with T3 and T7 promoters attached to lambda specific sequences:
IM(GT10)-(BAM/T3-30)-(-35)-47D
   CGGATCCAATTAACCCTCACTAAAGGGAAGCTTTTGAGCAAGTTCAG IM(GT10)-(SAL/T7-32)-(86)-51U
   GCGGAATTCTAATACGACTCACTATAGGGAGACAAATACA-GTTTTTCTTGT B. Nested (internal) lambda specific sequencing primers:
IM(GT10)-(-18)-16D  CCTGGTTAAGTCCAAG

IM(GT10)-(38)-24U  CTTATGAGTATTTCTTCCAGGGTA

Primers for PLATS[2]

A. Phage promoter oligonucleotides used for ligation:
SP6-26          CTTAATTAGGTGACACTATAGAATAG
    annealed pair = apSP6

SP6'-23         CTATTCTATAGTGTCACCTAATT

T7-26           TTCTAATACGACTCACTATAGGGAGA
    annealed pair = apT7

T7'-23          TCTCCCTATAGTGAGTCGTATTA

T3-26           TCTAATTAACCCTCACTAAAGGGAAG
    annealed pair = apT3

T3'-23          CTTCCCTTTAGTGAGGGTTAATT

B. Oligonucleotides available for use in PCR and in reverse transcriptase sequencing:
SP6-26, T7-26, T3-26

[1]All nucleotides are in 5'>3' orientation. Nomenclature for the oligonucleotides was previously described [Stoflet, et al., (1988)]. Briefly, the format is A(B)-(C-D)-E-F' A = the gene; B = the organism; C = description of any segment 5' to those that target the oligonucleotide to the appropriate site; D = total number 5' nucleotides as described in C; E = the location in the gene for the 5' most base which targets the nucleotide; F = the total length of the oligonucleotide, with "D" corresponding to a downstream orientation and "U" upstream. For these nucleotides, Im(GT10) refers to the Imm 434 EcoR1 site.
[2]To avoid confusion, trivial names were assigned to the consensus of promoter sequence.

Sequence data analysis and database searches were performed with the Sequence Analysis Software Package of the Genetics Computer Group (Univ. of Wisconsin Biotechnology Center, Madison, Wis. 53705), and dinucleotide frequency analysis performed on DNASTAR (DNASTAR Inc., Madison, Wis.).

Achlya DNA Preparation and Southern Blotting

DNA was prepared from E87, a male strain of Achlya, as previously described [Hudspeth, M. E. S., D. S. Bradford, C. J. R. Bradford and L. I. Grossman, Proc. Natl. Acad. Sci. 80:142–146 (1983)], with the substitution of Driselase (Sigma) in place of Cellulysin for the preparation of spheroplasts. Southern blotting [Manaiatis T., et al. (1988)] of moderate stringency was performed by hybridizing at 42° C. in 5×SSPE, 40% formamide, 2×Denhardt's solution, 10% dextran sulfate, 0.5% SDS (wt/vol), 0.1 mg/ml denatured E. coli DNA (Sigma). The estrogen receptor DNA binding regions from Xenopus and chicken were radiolabeled to high specific activity ($5 \times 10^9$ CPM/μg), by the method of PCR labeling [Schowalter, D. B. and S. S. Sommer, Anal. Biochem. 177:90–94 (1989]. Membrane washing was performed at a maximal stringency of 0.2×SSPE and 0.2% SDS at 45° C.

Size-fractionated Library Preparation and Screening

Eco R1 digested Achlya DNA for library preparation was size fractionated on a 1% agarose gel, the 1 kb to 1.3 kb range excised, and the DNA eluted following GENECLEAN (Bio101, La Jolla, Calif.) protocol. Size-fractioned DNA (50 ng) was ligated into calf intestinal phosphatase treated, Eco R1 digested lambda gt10 (Promega), packaged with Promega packagene extracts, diluted with SM buffer, plated with exponential c600 hfl cells, and screened with radiolabeled Xenopus estrogen receptor DNA binding region as previously described [Davis, L. G., M. D. Dibner, and J. F. Battey, Basic Methods in Molecular Biology, Elsevier, New York (1986)].

Crude Fractionism of Lambda DNA and Direct Sequencing of the Termini of the Clones Positive plaques from the secondary screen plates were mixed with 0.2 OD (600 nm) of exponential c600hfl cells in 20 ml of LB media, and incubated approximately 4 hr at 37° C. to lysis [Davis, et al. (1986)]. One ml of each lysis culture was removed and centrifuged for 3 min at 12,500×g. The supernatant was extracted in 1 volume of phenol/chloroform/Isoamyl-alcohol (50:49:1), diluted 1:10,000-fold, and sequenced with genomic amplification with transcript sequencing [Stoflet, et al., (1988], as modified by [Sarkar, et al. (1988)] PCR was performed with primers containing phage RNA polymerase promoters and sequences complementary to the lambda gt10 imm 434 gene which flanks the insert: IM(GT10)-(Sal/T7-32)-(86)-51U and IM(GT10)-(Bam/T3-30)-(30)-47D (see Table 2). Transcription of the amplified segments and transcript sequencing with the $^{32}$p radio-labeled internal sequencing primers IM(GT10)-(-18)-16D and IM(GT10)-(38)-24U yielded the sequence of the termini of the clones.

Figure 9:
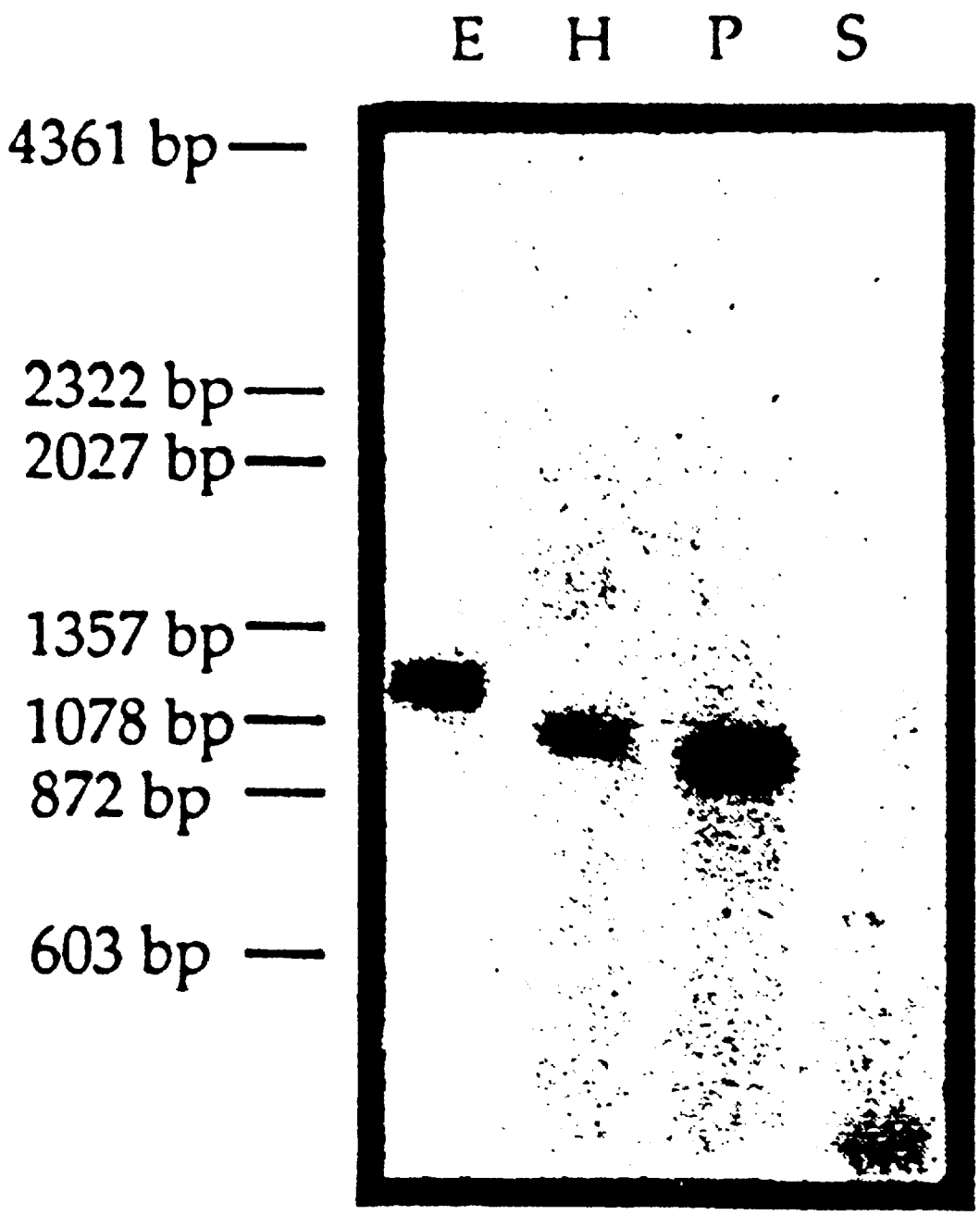
FIG. 9. Southern blot of Achlya DNA probed with the 200 bp DNA binding region of the Xenopus estrogen receptor. Ten µg of Achlya DNA digested with Eco R1 (E), Hind III (H), Pst 1 (P), and Sau 3a (S) were elecrophoresed on a 1% agarose gel, blotted, and hybridized with 40 million cpm of probe. Final wash was 0.2×SSPE, 0.1% SDS, at 45° C. for 30 min. Hind III digested lambda DNA, and Hae III digested φX174 DNA size markers are noted to the left.

Protocol for Direct Sequencing of Internal Regions by Promoter Ligation and Transcript Sequencing Generally, PLATS was performed on an amplified segment of DNA that contained a different phage promoter on each and (see Results and FIG. 9). Aliquots of DNA (50 ng) were digested in 20 μl with restriction enzymes that generate blunt ends or 5' base overhangs. If 5' base overhangs were produced, blunt ends were generated by increasing the incubation volume to 30 μl with 0.5 μl Klenow fragment (2.5 units), 3 μl 10×Klenow buffer (500 mM Tris-HCl pH 7.5, 100 mM MgCl$_2$, 10 mM dithiothreitol (DTT), 500 μg/ml bovine serum albumin, and 3 mM each dATP, dTTP, dGTP, and dCTP), and 6.5 μl dH$_2$O and continuing the incubation at 37° C. for 20 min [Cobianchi, F. and S. H. Wilson, S. L. In Berger, and A. R. Kimmel, (eds) Methods in Enzymology, Academic Press Orlando, Fla., Vol. 152:94–110]. Ligations were performed in 10 μl reactions containing 1 μl 10×ligase buffer (500 mM Tris-HCl pH 7.4, 100 mM MgCl$_2$, 200 mM DTT, 10 mM ATP, and 50 μg/ml BSA), 1 μg apSP6, apT7 or apT3 (3 pmoles), 1 μg digested, blunt-ended fragment (2–3 ng), 0.05 BRL units T4 DNA ligase (BRL), and 6 μl dH2O for >4 hr at 15° C.

The following conditions for PCR amplification were used in all experiments. Target sequence, in this case 1 μl of the above ligation, was mixed with 100 μl 1×PCR buffer (10 mM Tris-HCl pH 8.3, 50 mM KCl, 1.5 mM MgCl$_2$, 0.01% (w/v) gelatin, and 200 μM each dATP, dttp, dGTP, and dCTP), and 100 pmoles of each of two specified oligonucleotides. After incubating 10 min at 94° C., 2:5 units of Taq DNA polymerase (Perkin Elmer/Cetus, Norwalk, Conn.) and 50 μl of light mineral oil were added, and 30 cycles of PCR were performed (denaturation: 1 min at 94° C.; annealing: 2 min at 50° C.; and elonation: 2 min at 72° C.) with the Perkin Elmer/Cetus automated thermal cycler.

Amplified material was electrophered on a 2% agarose gel for 150 V-hr, from which appropriate sized segments were excised, and the DNA eluted (see below). Electrophoresis and elution are optional steps which can be omitted if the first 30–40 bases of sequence are not required. Transcription was performed on 3 μl of eluted DNA in 20 μl of IX transcription buffer (40 mM Tris-HCl pH 7.4, 6 mM MgCl$_2$, 4 mM spermidine, 10 mM DTT, 14 units of the appropriate RNA polymerase, and 500 μM each ATP, CTP, GTP, and UTP) for 1 hr at 37° C. [Davis, et al. (1986)]. Reactions were stored at −20+ C. until sequenced.

Dideoxy sequencing with reverse transcriptase was performed on transcripts primed with the appropriate oligonucleotide from the PCR reaction. The end-labeling of the oligonucleotides is as previously described, but note that gamma-$^{32}$P-ATP is the correct radialabel donor [Stoflet, et al. (1988)). Briefly, 2 μl of the transcription reaction and 1 μl of $^{32}$p radiolabeled sequencing primer were added to 10 μl of annealing buffer (250 mM KCl and 10 mM Tris-HCl pH 8.3). The samples heated at 80° C. for 3 min and then annealed for 45 min at 45° C. In 1.5 ml microfuge tubes labeled A, T, G, and C the following were added: 3.3 μl of reverse transcriptase buffer (24 mM Tris-HCl pH 8.3, 16 mM MgCl$_2$, 8 mM DTT, 0.8 mM DATP, 0.4 mM dCTP, 0.8 mM dGTP, 1.2 mM dTTP, 100 μg/ml actinomycin D, and 3 units AMV reverse transcriptase); 1 μl of 1 mM ddATP to all the "A" tubes, 1 μM of 1 ml ddTTP to all the "T" tubes, 1 μl of 1 mM ddGTP to all the "G" tubes, 1 μl of 0.25 mM ddCTP to all the "C" tubes; and finally, 2 μl of the primer RNA template solution. The samples were incubated at 45° C. for 45 min, and stopped by adding 3 μl of 100% formamide with 0.3% bromphenol blue and xylene cyanol FF. Samples were heated for 5 min at 80° C., placed on ice for 5 min, and 2 ml electrophoresed on a 50 cm 7% denaturing acrylamide gel for 4000 volt-hours.

Several of the transcripts were sequenced with the inclusion of α-$^{35}$S-DATP and nonradiolabelled primer as described previously [Mierendorf, R. C. and D. Pfeffer, S. L. In Berger, and A. R. Kimmel, (eds) Methods in Enzymology, Academic Press, Orlando, Fla., Vol. 152:563–566). The success of good sequence from both techniques was dependent on the quality and homogeneity of the transcript.

Elution of Segments from Agarose Gels

Segments were eluted from agarose gels by one of two methods depending upon size. For segments <400 bp, bands were excised with a minimum of exposure to UV light, placed in a 0.5 ml centrifuge tube, frozen for 5 min in a methanol dry ice bath, and spun through a pin hole into a 1.5 ml centrifuge tube (Tautz, D. and M. Renz, Anal. Biochem., 132:14–19 (1983)] as modified by the GENECLEAN protocol (Bio 101).

RNA Amplification and Northern Analysis

Achlya mRNA was isolated on cesium chloride gradients from freeze fractured Achlya in guanidine-isolthiocyanate and purified on an oligo-dT column [Davis, et al., (1986)]. PCR amplification of first strand cDNA prepared from the above Achlya mRNA was as previously described [Sarkar, G. and S. S. Sommer, Nucleic Acids Research 16:5197 (1988); Vogelstein, B. and D. Gillespie, Proc. Natl. Acad. Sci. 76:615–619 (1979)].

Northern analysis was performed on Achlya mRNA electrophoresed in a 1% formalydehyde gel, blotted, and hybridized with random primer radiolabeled DNA probes (Amersham) to each of the strands of the 1.1 kb Achlya clone as previously described [Davis, et al., (1986)]. E. coli DNA was used as nonspecific nucleic acid in prehybridization and hybridization conditions as described for Southern blotting. Membrane washing conditions were increased to a final wash of several hours at 65° C. in 0.05×SSPE and 0.1% SDS.

Results

In an attempt to find additional members of the steroid receptor family in the water model *Achlya ambisexualis* and the yeast *Saccharomyces cerevisae*, low stringency Southern analysis was performed on genomic DNA after genomic DNA after digestion with multiple restriction enzymes. Hybridization with the probes from either the Xenopus or chicken estrogen receptor DNA binding region revealed a cross-reacting signal from Achlya DNA (FIG. 9), while *S. cerevisiase* showed no cross-reactivity. The signal obtained with the Xenopus probe persisted when the stringency of the wash was increased to 0.2×SSPE at 55° C. (data not shown). The 1.1 kb band seen in the Eco R1 lane (from here on referred to Aa1.1) was cloned into lambda gt10 by making a 1.0–1.3 kb size fractionated mini-library of Eco R1 digested Achlya DNA.

Screening the library with the Xenopus estrogen receptor DNA binding region probe yielded eight positive clones. Of these eight, five were selected for secondary screening by PCR. Four positive plaques from each of the five clones in secondary screening were grown in small scale liquid culture. A crude DNA fraction was rapidly prepared (approx. 10 min) by phenol extraction without subsequent ethanol precipitation (see Materials and Methods), and the termini of the inserts were directly sequenced with GAWTS. In brief, PCR was performed with oligonucleotides containing T3 and T7 phage promoters with specificity for vector sequences flanking the Eco R1 site in lambda gt10 (Table 2). From each of the five initial clones, PCR amplification produced a segment of the same size (1.3 kb). Transcripts were prepared with T7 and T3 RNA polymerase respectively, and transcript sequencing of the termini performed with internal sequencing primers. All five initial clones were found to be identical.

Sequencing with PLATS

Figure 10:
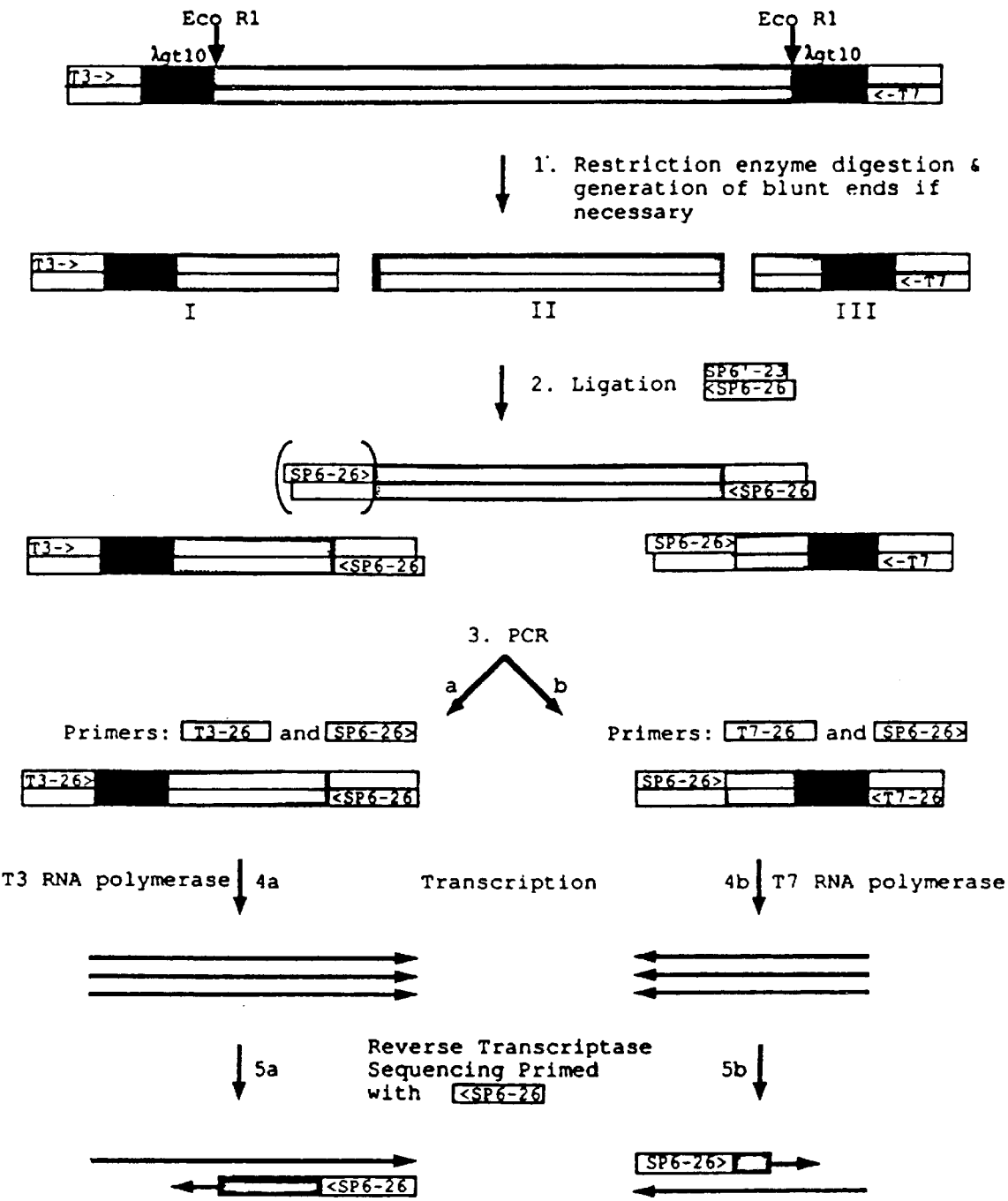
FIG. 10. Steps in the sequencing of an insert with promoter ligation, and transcript sequencing (PLATS) as described in the specification.

To obtain internal sequence data without subcloning or continually generating new sequencing primers, PLATS was developed (FIG. 10). In the example shown, the T3 and T7 phage promoters flank the amplified gt10 insert. The size of clone amplified is limited only by the ability to amplify with PCR. Digestion with a restriction enzyme results in three fragments. Ligation of a double stranded SP6 promoter sequence (apSP6) to these fragments produces a mixture of fragments as shown after step 2 in FIG. 10. Neither the promoter nor the ends of the original clone contain 5' terminal phosphates, thus forcing the promoters to ligate only to the newly generated blunt ends. After ligation, sequence from restriction fragment 1 can be obtained by: 1) performing PCR with T3-26 and SP6-26 (see Table 2); 2) eluting the segment of correct size from an agarose gel, (optional, but this eliminates a short spurious transcript presumably arising by self-priming of the oligonucleotides which attenuates the desired sequence and obscures the first 30–40 bp); 3) transcribing with T3 RNA polymerase; and 4) reverse transcriptase mediated dideoxy sequencing with SP6-26 as the sequencing primer (steps 3a, 4a, and 5a). Likewise, sequence from restriction fragment II can be obtained by performing an amplification with T7-26 and SP6-26 (steps 3b, 4b and 5b). Note that restriction fragment II can potentially be amplified by acquiring an SP6 promoter at each end. However, blunt-end ligation is inefficient, and such spurious amplification products have not been observed in practice (e.g., see FIG. 11), presumably because only a small fraction of molecules acquire even on SP6 promoter sequence.

FIG. 11 illustrates steps 1–4 of PLATS for Rsa 1 and Taq 1 fragments which produces fragments with blunt ends and 5' overhang, respectively.

FIG. 11A shows a generation of novel sequencing templates with PLATS using 2.0% agarose gel of the amplified 1.1 kb Achyla clone followed by digestion with Rsa 1 promoter ligation, amplification, and transcription. Five µl was loaded from each reaction. Lane 1: PCR of the entire lambda gt10 clone Aa.1 with the oligonucleotides IM(GT10)-(BAM/T3-30)-(-35)-47D and IM(GT10)-(SAL/T7-32)-(86)-51U. Lane 2: Three fragments produced by digestion of this amplified segment with Rsa 1. The 240 and 290 bp fragments stain less intensely. Lanes 3 and 4: PCR amplified material subsequent to promoter ligation (apSP6) of Rsa 1 digested Aa1.1. T3-26 and SP6-26 (lane 3) or T7-26 and SP6-26 (lane 4) were the PCR primers. The amplified segments are 26 bp larger than the corresponding restriction fragments shown in lane 2. Lanes 5 and 6: Transcription of the segment from lane 3 with T3 RNA polymerase (lane 5) or the segment from lane 4 with T7 RNA polymerase (lane 6). FIG. 11B show generation of sequencing templates subsequent to Taq 1 restriction enzyme digestion of Aa1.1. After digestion, blunt ends were generated with Klenow. Lane 1: Taq 1 digestion of Aa1.1. Lanes 2 and 3: PCR amplified material subsequent to promoter ligation (apSP6) of Taq 1 digested Aa1.1. T3-26 and SP6-26 (lane 2) or T7-26 and SP6-26 (lane 3) were the PCR primers. Lane 4 and 5: Transcription of the segment from lane 2 with T3 RNA polymerase (lane 4) or the segment from lane 3 with T7 RNA polymerase (lane 5). Hind III digested lambda DNA, an Hae III digested φX174 DNA size markers are noted to the left of both panels.

Figure 12:
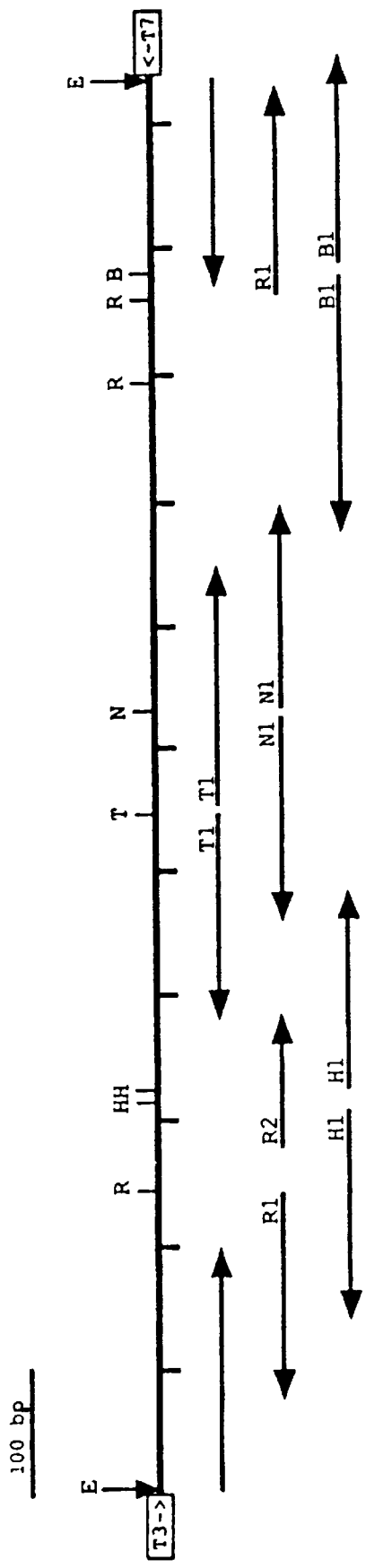
FIG. 12. Partial restriction map and PLATS sequencing strategy for Aa1.1 clone. The two arrows extending from the T3 and T7 ends were obtained by direct sequencing of the termini as described in the specification. The restriction enzymes used in the PLATS sequencing of the internal regions are shown at the base of the arrows (B-Bs1 U1, E-Eco R1, H-Hind III, N-Nla IV, R-Rsa L, and T-Taq 1). Segments labeled "1" were sequences resulting from one round of PLATS. The label "2" denotes that two rounds of PLATS were required to obtain the sequence.

Sequences from the Taq 1 site and the terminal Rsa 1 sites toward the ends of the clone Aa1.1 were generated after one round of PLATS (FIG. 12). To generate sequence internal to the 5' Rsa 1 site, a second round of PLATS was performed (R2 in FIG. 12). For the second round of PLATS, the Taq 1 segment containing the T3 and SP6 promoters flanking the Aa1.a segment from 1 to 550 bp (FIG. 12) was digested with Rsa 1. Ligation was performed with apT7, and PCR was performed with T7-26 and Sp6-26. The amplified product was transcribed with Sp6 polymerase and sequenced with T7-26 as a primer. Although two rounds were sufficient for Aa1.1 (by choosing another restriction enzyme, only one round would have been required), ligation with the appropriate phage promoter can provide as many rounds as desired.

After initial sequence has been generated, computer analysis can indicate which other restriction endonucleases cleave at useful locations. In this manner, readily available restriction enzymes can be used, and the sequence of the entire segment can rapidly be obtained without the need for formal restriction mapping (FIG. 12).

To verify the PLATS sequencing technique, the Aa1.1 clone was subcloned into M13 phage as a full-length Eco R1 fragments. Both strands of two of each of these clones were sequenced using the Sequenase DNA sequencing kit. The sequence agreed with that obtained using PLATS. In two clones, unique single base changes were noted relative to the other clones and to PLATS. This probably represents an error by Taq polymerase during DNA amplification by PCR as previously described [Dunning, et al., (1988)]. PLATS generates sequence from a population of molecules, making it insensitive to occasional errors by Taq polymerase.

Sequence of Aa1.1

One long open reading frame was found (FIG. 13). Search of the NBRL protein database and the GENBANK DNA database did not reveal a similarity to previous sequence. Comparison of Aa1.1 to the Xenopus estrogen receptor DNA binding region probe shows a stretch of 37 base pairs (752–789) with 76% identity to the probe which includes a segment with identity at 18 out of 19 bp. This portion of the Xenopus DNA binding region corresponds to the second half of the second "zinc finger". However, this does not provide a complete "zinc finger" region, and the amino acid sequence is not in an open reading frame, making Aa1.1 a false positive. On further examination of the Aa1.1, two interesting motifs are noted: (1) a possible zinc finger form $C-X_2-C-X_{12}-H-X_3-C$, and 2) a stretch of 19 amino acids where 58% are glutamate and aspartate (see boxes in FIG. 13).

Aa1.1 represents the first sequence obtained from the Oomycetes, one of the two subdivisions of the Phycomycetes. Phycomycetes are characterized by a lack of hyphal septation, and they constitute one of the four subclasses of fungi. For Aa1.1., codon preference is quite marked (Table 3). The preferences bear some resemblance to that found in the Ascomycetes such as S. Cerevisiae [Sharp, P. M., T. M. F. Tuohy, and K. R. Mosurski, Nucleic Acids Research, 14:5125–5143 (1986)]. The distribution of dinucleotides is of note in that there is a marked deficiency of TpA when compared to other AT-rich dinucleotides (Table 4). TpA is avoided in many organisms [Boudraa, M. and P. Perrin Nucleic Acids Research 15:5729–5737 (1987)], although to a lesser extent in mammals [ca. 75% of the expected frequency, 29] and S. cervisiae (unpublished).

TABLE 3

Aa1.1 ORF Codon Preferences

| First Position | Second Position | | | | Third Position |
|---|---|---|---|---|---|
| (5'-end) | U | C | A | G | (3'-end) |
| U | Phe-7 | Ser-10 | Tyr-4 | Cys-2 | U |
|  | Phe-6 | Ser-4 | Tyr-8 | Cys-3 | C |
|  | Leu-1 | Ser-2 | End-0 | End-0 | A |
|  | Leu-14 | Ser-2 | End-0 | Trp-6 | G |
| C | Leu-14 | Pro-10 | His-9 | Arg-12 | U |
|  | Leu-12 | Pro-1 | His-3 | Arg-7 | C |
|  | Leu-2 | Pro-10 | Gln-13 | Arg-4 | A |
|  | Leu-2 | Pro-0 | Gln-6 | Arg-0 | G |
| A | Ile-8 | Thr-6 | Asn-9 | Ser-2 | U |
|  | Ile-3 | Thr-2 | Asn-3 | Ser-3 | C |
|  | Ile-0 | Thr-5 | Lys-8 | Arg-0 | A |
|  | Met-5 | Thr-4 | Lys-7 | Arg-0 | G |
| G | Val-11 | Ala-23 | Asp-13 | Gly-13 | U |

TABLE 3-continued

Aa1.1 ORF Codon Preferences

| First Position | Second Position | | | | Third Position |
|---|---|---|---|---|---|
| (5'-end) | U | C | A | G | (3'-end) |
|  | Val-4 | Ala-6 | Asp-6 | Gly-5 | C |
|  | Val-0 | Ala-8 | Glu-26 | Gly-9 | A |
|  | Val-4 | Ala-2 | Glu-3 | Gly-1 | G |

TABLE 4

Aa1.1 Nearest Neighbor Analysis

| 5' \ 3' | A | C | G | T |
|---|---|---|---|---|
| A | 8.12 | 5.08 | 4.73 | 6.33 |
| C | 7.14 | 4.01 | 4.55 | 8.83 |
| G | 6.33 | 7.23 | 4.19 | 5.26 |
| T | 2.68 | 8.30 | 9.46 | 7.67 |

Aa1.1 is transcribed

Figure 14:
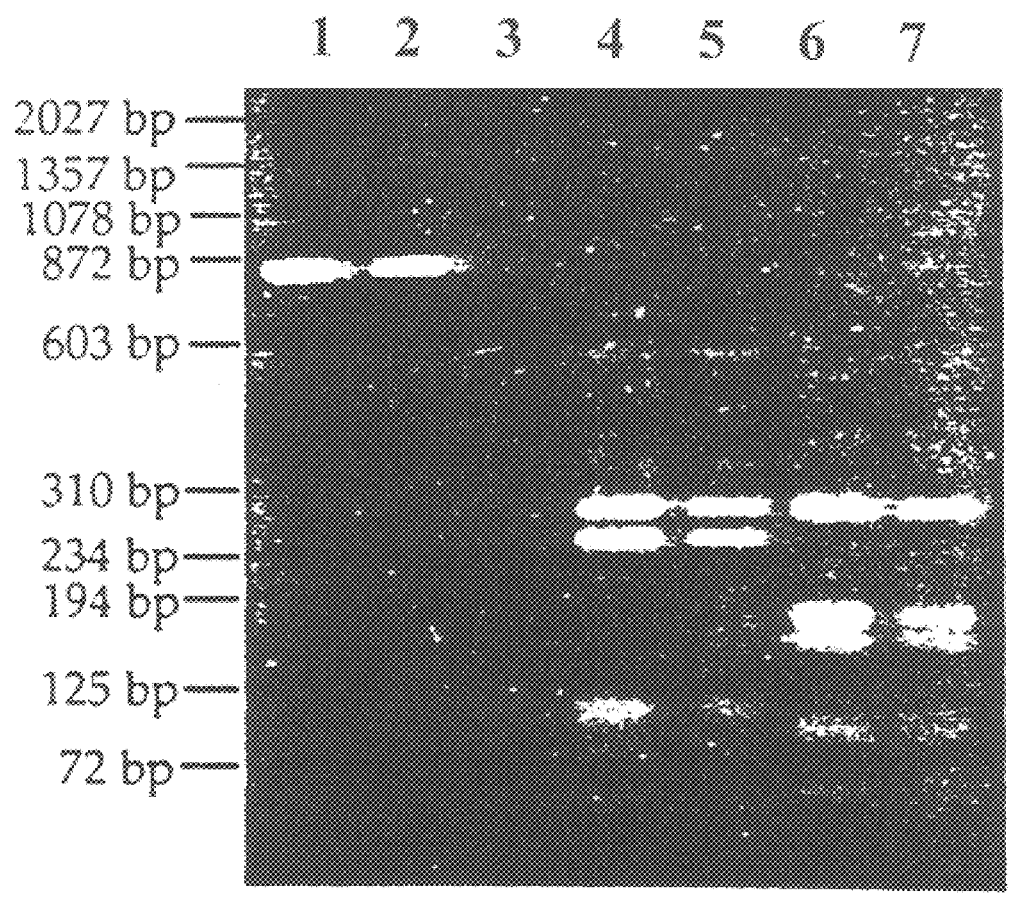
FIG. 14: An 800 bp segment of Aa1.1 was transcribed and lacks introns. PCR was performed with Aa-(213)-16D and Aa-(1017)-17U on 100 ng Achlya genomic DNA, 10 ng first strand cDNA, and 100 ng of the mRNA used to make the cDNA. Five µl of each segment was electrophoresed on a 2.5% agarose gel (lanes 1–3, respectively). The 800 bp genomic segment was digested with Alu 1 (lane 4) and Mn1 1 (lane 6). Likewise, the cDNA segment was digested with Alu 1 (lane 5) and Mn1 1 (lane 7). Hind III digested lambda DNA, and Hae III digested φX174 DNA size markers are noted to the left.

PCR was performed on Achlya genomic DNA, cDNA, and the poly A RNA used to prepare cDNA. The PCR primers, when applied to genomic DNA, should amplify an 801 bp segment spanning bases 217 to 1017. An 800 bp segment was obtained from both DNA and cDNA (FIG. 14). No segment was observed from mRNA indicating that the cDNA signal reflects sequences in mRNA rather than contamination of the RNA preparation by genomic DNA. When the segments were digested with Alu 1 and Mnl 1, the fragments from genomic DNA and cDNA appeared identical (FIG. 14). This strongly suggests that there is no intron in this segment of Aa1.1 which includes the putative zinc finger and the acidic stretch. Northern analysis of Achlya mRNA with strand specific radiolabelled probes reveals a single band in the range of 3 to 4 kb corresponding to the coding strand of the ORF (data not shown).

Discussion

Promoter ligation and transcript sequencing is an alternative method for sequencing clones isolated form DNA libraries. Several advantages of PLATS include: 1) lambda DNA preparation and subcloning are not required; 2) simple, completely in vitro laboratory manipulations results in rapid progression from clone isolation to sequence data; 3) the primers, six generic and four vector specific, can be utilized to sequence all clones in a vector class, making it an economical method; 4) the amplifications afforded by both PCR and phage transcription can compensate for poor yields in other steps, making the method technically robust; 5) sequences from both strands can readily be obtained from one starting clone; and 6) single molecules are not cloned from a PCR mix, rendering the method insensitive to the error rate of Taq polymerase since the sequence at every base represents the predominant one of the population of molecules.

The transcription and sequencing steps of PLATS were performed after the isolation of the appropriate band from an agarose gel because spurious amplification products from the PCR primers produce an abundance of short transcripts. In another context, it has been observed that optimizing the concentration of the oligonucleotides can eliminate these short spurious transcripts. A similar optimization may allow transcription to be performed directly on the amplified material. This may well allow the entire procedure to be performed by sequential pipetting from one tube to the next without centrifugation or in vivo manipulations, thereby facilitating automation. The potential for automation is an important attribute of PLATS.

As a final technical note, it is initially necessary to find one or more enzymes that cleave the insert. Enzymes with four base recognition sites (such as Taq 1 and Rsa 1) are generally best. However, certain endonucleases with five and six base recognition sequences may in some cases be better choices in organisms with a skewed GC content. For example, if an organism has a GC content of 30%, a restriction endonuclease with a four base recognition sequence of 100% G and C is expected to cleave an average of once per 1675 bp. An endonuclease with a 6 base recognition sequence that is 100% A and T is expected to cleave once per 1372 bp.

The clone isolated was false positive, yet the stability of the hybridization signal (0.2×SSPE, 55° C.) was greater that used to isolate the Knirps-related gene in Drosophila with the retinoic acid receptor probe. This gene, a member of the steroid/thyroxine/retinoic acid receptor superfamily, is thought to be involved in the development of the organism [Oro, A. E., E. S. Ong, J. S. Margolis, J. W. Posakony, M. McKeown, and R. M. Evans, Nature, 336:493–496 (1988)]. Fortuitously, Aa1.1 is an expressed open reading frame which contains two interesting sequence motifs. The potential DNA-binding finger identified (C—$X_2$—C—$X_{12}$—H—$X_3$—C) contains three cysteines and a histidine with amino acid spacings that are consistent with known zinc-finger domains [Klug, A. and D. Rhodes, TIBS 12:464–469 (1987); Berg, J. M., Science, 232:485–487 (1986)]. While the amino acid arrangement commonly observed for zinc-binding finger domains are either all cysteines (with 4 to 6 cysteins that may participate in zinc binding [Evans, R. M., S. M. Hollenberg, Cell, 52:1–3 (1988)]), or one pair of cysteins and one pair of histidines, no known chemical or steric constraint precludes three cysteins and one histidine from forming a zinc-binding configuration. The RAD18 DNA repair gene of S. cerevisiae, which is thought to bind DNA [Jones, J. S., S. Weber, and L. Prakash, Nucleic Acids Research, 16:7119–7131 (1988)), contains three cysteines and one histidine in the above spacing. RAD18 also contains two other potential DNA-binding zinc-fingers: the 5' most sequence (C—$X_2$—C—$X_{11}$—C—$X_4$—C) is of more conventional structure while the middle sequence once again contains three cysteines and one histidine (C—$X_3$—H—$X_6$—C—$X_2$—C).

A comparison of the putative zinc-finger domains in Aa1.1 and RAD18 with a steroid receptor consensus sequence [Evans (1988)] is shown in FIG. 15. Comparison of Aa1.1 with the individual receptor sequences does not shown any more similarity than that shown in the consensus comparison. It is intriguing that Aa1.1 contains a pair of tyrosines in a position analogous to the invariant phenylalanine pairs that are absolutely conserved in members of the steroid/thyroxine/retinoic acid receptor superfamily. Moreover, RAD18 contains a phenylalanine, tyrosine pair in the loop segment of the finger structure. Pairs of phenylalanine and tyrosine (PHE/PHE, PHE/TYR, TYR/PHE, or TYR/TYR) are infrequent combinations. In Aa1.1, RAD18, and the Xenopus estrogen receptor, they are found elsewhere at a frequency of one per 380 amino acids. Such pairs may aid DNA binding by intercalation.

In both GCN4 and GAL4, acidic domains have been implicated in transcriptional activation in the context of zinc fingers (Hope, I., M. Subramony, and K. Struhl, Nature, 333:635–640 (1988); Ma, J. and M. Ptashne, Cell, 51:11–119 (1987)]. Acidic domains also have been implicated in transcriptional activation by the glucocorticoid receptor [Hollenberg, S. M. and R. M. Evans, Cell, 55:899–906 (1988)] Aa1.1 also has an acidic domain suggesting that it is a member of a class of transcriptional regulators which contains a zinc finger with three cysteines and one histidine coupled to an acidic activator sequence.

Novel Genomic Sequencing W/Plats

Plats can be modified if novel sequence adjacent to a genomic or cDNA sequence is desired.

The example of a genomic sequence will be considered where ABC are known sequence and DEF are adjacent unknown sequence.

Step 1: Cleave genomic DNA with a restriction endonuclease.

Step 2: if necessary, generate blunt ends.

Step 3: Attach a dual promoter sequence (e.g. T7 followed by SP6) by blunt end ligation, preferably under conditions there it is unlikely that a molecule will receive a promoter at both ends.

Step 4: Transcribe. In this example, T7 RNA polymerase would be used for transcription.

Step 5: Digest with DNase and subsequently inactivate the DNase.

Step 6: Perform cDNA synthesis using a downstream primer specific for sequence A.

Step 7: Perform PCR with a downstream primer specific for sequence B and an upstream primer specific for SP6.

Step 8: Transcribe with SP6 RNA polymerase.

Step 9: Sequence with reverse transcriptase using downstream primer specific for sequence C.

Multiple variations of the general approach can be envisioned as examples:

1) A second endonuclease can be used in step 1 to generate a fragment with one 3' overhang which will be resistant to blunt end ligation at that end.
2) DNA can be sheared in step 1 rather than digested with a restriction endonuclease.
3) Self-priming RNA can be eliminated before entering step 4.
4) Multiple rounds of PCR can be performed in step 6.
5) Another promoter (such as T3) can be added to sequence B in step 6 so that sequence from an upstream strand could generated by eluting the appropriate band from a gel, transcribing with T3 RNA polymerase, and sequencing with a primer containing the SP6 promoter sequence.
6) Sequence from mRNA can be obtained by additional modifications which capitalize on the reduced sequence complexity and the presence of poly A on virtually all mRNAs.

PCR Amplification of Specific Alleles

Inefficient DNA amplification occurs if a genomic sequence contains a single base mismatch near the 3' end of a polymerase chain reaction (PCR) oligonucleotide primer. This readily allows two alleles that differ by one base pair to be distinguished by PCR. Such PCR amplification of specific alleles (PASA) shows promise for population screening of certain genetic diseases because the technique is rapid, technically robust, inexpensive, nonisotopic, and amenable to automation. PASA was used successfully to screen a population for one possible polymorphism in Factor IX and two mutations associated with phenylketonuria.

The ability to screen populations for carriers of genetic disease in an accurate, inexpensive, and rapid manner would provide the opportunity for widespread genetic counseling and, ultimately, the possible elimination of such diseases. A successful example of protein based carrier screening is Tay-Sachs disease ($G_{M2}$ gangliosidosis type B), which is caused by a deficiency in β-hexosaminidase activity. Since non-carrier and carrier levels of enzymatic activity do not overlap, genetic status can be unequivocally assigned. [Ben-Yoseph, U., J. E. Reid, B. Shapiro, H. L. Nadler., Am. J. Hum. Genet., 37:733–748 (1985)] Screening for Tay-Sachs has reduced markedly the incidence of this disease in Ashkenazi Jews. [O'Brien, J. S. The gangliosidases. In: Stanbury J. B., J. B. Wyngaarden, D. S. Fredrickson, J. L. Goldstein, M. S. Brown, eds. Metabolic Basis of Inherited Disease. New York: McGraw-Hill, 1983:945–969]. Unfortunately, measurements of protein or metabolite levels for other genetic diseases are not usually accurate enough for this type of population screening. Population screening may eventually be possible, however, with DNA-based methods.

Phenylketonuria (PKU) is one disease amenable to DNA-based screening. Classical PKU is an autosomal recessive disease affecting one in 10,000 newborn Caucasians of northern European descent. The disease is the result of a deficiency in hepatic phenylalanine hydroxylase activity (PAH), which causes a primary elevation of serum phenylalanine and secondary abnormalities in compounds derived from aromatic amino acids. [Blau, K. In: Yondim MBH, ed. Aromatic Amino Hydoxylases and Mental Diseases. New York: Wiley, 1979:79–139] If left untreated in infancy, severe mental retardation ensures. While treatment with a low phenylalanine diet can prevent mental retardation, the disease has not been rendered benign. Phenylketonurics still encounter problems, including: 1) failure to reach full intellectual potential due to incomplete compliance with the very stringent dietary therapy [Holtzman, N. A., R. A. Kronmal, W. Van Doorninck, C. Azen, R. Koch, New Engl. J. Med., 314:593–598 (1986)]; 2) a high frequency of birth defects in children of affected females (Scriver, C. R., C. L. Clow, Ann Rev. Genet., 14:179–202 (1980)]; and 3) a high incidence of behavorial problems. [Holtzman, et al., (1986); Realmuto, G. M., B. D. Garfinkel, M. Tuckman, M. Y. Tsai, P-N. Chang, R. O. Fisch, S. Shapiro., J. Nerv. Mental Dis., 174: 536–540 (1986)]

Subsequent to the cloning of PAH cDNA, [Kwok, S. C. M., F. D. Ledley, A. G. DiLella, K. J. H. Robson, S. L. C. Woo. Biochem., 24:556–561 (1985)) it was found that 90% of the PKU alleles in the Danish population are confined to four haplotypes. [Chakraborty, R., A. S. Lidsky, S. P. Daiger, F., Guttler, S. Sullivan, A. G. DiLella, S. L. C. Woo., Hum. Genet., 76: 40–46.(1987)] The mutations in haplotypes 2 and 3 represent 20% and 40% of the PKU alleles, respectively. The mutation in haplotype 2 is a C to T transition at amino acid 408 in exon 12 of the PAH gene [DiLella, A. G., J. Marvit, K. Brayton, S. L. C. Woo., Nature, 327:333–336. (1987)] and the mutation in haplotype 3 is a G→A transition at the intron 12 donor splice junction. (DiLella, A. G., J. Marvit, A. S. Lidsky, F. Guttler, S. L. C. Woo., Nature, 322:799–803 (1986)] The mutant alleles associated with haplotypes 2 and 3 are also prevalent in the United States population. [Moore, S. D., W. M. Huang, R. Koch, S. Snyderman, S. L. C. Woo., Am. J. Hum. Genet., 43:A90 (1988)] When the mutations in haplotypes 1 and 4 are defined, 90% of all PKU carriers of northern European descent (approximately 4 million individuals in the United States alone) could be directly diagnosed by DNA methods.

The current methods which can detect such point mutations include: i) direct DNA sequencing, [Gyllensten, U. B., H. A. Erlich., Proc. Natl. Acad. Sci., 85:7652–7656 (1988)]; ii) denaturing gradient gel electrophoresis (Myers, R. M., N. Lumelsky, L. S. Lerman, T. Maniatas, Nature, 313:495–498 (1985)]; iii) polymerase chain reaction (PCR) followed by allele-specific oligonucleotide hybridization [DiLella, A. G., W-M. Huang, S. L. C. Woo., Lancet, 1:497–499 (1988)]; iv) allele specific DNA ligation [Landegren, U., R. Kaiser, J. Sanders, L. Hood, Science, 241:1077–1080 (1988)]; and V) ribonuclease cleavage of mismatched heteroduplexes. [R. M., Myers, Z. Larin, T. Maniatas. Science, 230:1242–1246 (1985)] However, these techniques in their present form are unlikely to find widespread application in population screening because they lack the requisite speed, technical ease, and/or cost effectiveness. In an effort to provide a suitable means of screening a large number of individuals, the inventor has developed PCR amplification of specific alleles (PASA), a method which uses unlabeled oligonucleotides to rapidly and reliably distinguish between alleles that differ at only one base pair.

Methods

PCR was performed as described above. DNA concentrations were 250 ng of total DNA in 25 μl reactions, unless otherwise noted. For each pair of PCR primers, the allele specific PCR primer was designed to have an estimated $T_m$ under standard conditions (1 M NaCl) of 44° C. [Bonner, T. I., D. T. Brenner, B. R. Neufeld, and R. J. Britten, J. Mol. Biol., 81:123–135 (1973)). The primer which does not anneal to the polymorphic site was designed to have a $T_m$ of 48° C. Oligonucleotide concentrations were at 1 μM each, unless otherwise noted in the text. It was observed that decreasing the total oligonucleotide concentration by 4 to 20-fold often increased specific amplification. Thirty to forty cycles were performed with little observable difference. Consequently, 35 cycles were used routinely.

Sequencing was performed using genomic amplification with transcript sequencing (GAWTS). In brief, the region to be sequenced is amplified by PCR using oligonucleotides with the T7 phage promoter. PCR aliquots are used to directly transcribe the amplified PCR product to RNA using T7 RNA polymerase. The RNA transcript is then used for dideoxy sequencing with reverse transcriptase.

Results

Optimization of PASA

Oligonucleotides were synthesized to match and mismatch the T and A alleles at base pair 48 (exon 1) of the Factor IX gene (FIG. 16). The T allele is common, while the A allele has only been identified in E91M, an individual without a known coagulopathy (Koeberl, et al., submitted). This polymorphism was chosen for the initial test of the PASA method because: 1) it was thought that specificity might be easier to achieve when two genomic alleles represent a transversion rather than a transition; 2) the rare allele abolishes a BclI site so the results of PASA could easily be checked by amplifying flanking DNA and digesting with BclI; and 3) the frequency of the A allele in the population was of interest.

It was hypothesized that a mismatch near the 3' end of the oligonucleotide would be the most likely to hinder the 3' elongation of the Taq polymerase. Two PCR primers were synthesized to be identical to the antisense strand of each allele by differing at the penultimate 3' base (FIG. 16). The $15(A^{n-1})$ oligonucleotide was specific for the uncommon A allele present in E91M, while $15(T^{n-1})$ was specific for the common T allele as found in individual E100M. A 182 base pair amplification product was expected if PCR was performed with F9-U(-121)-15D and either $15(A^{n-1})$ or $15(T^{n-1})$.

FIG. 16 shows the sequence of selected Factor IX oligonucleotides. Oligonucleotides were synthesized for detection of the A and T alleles at base 48 of the Factor IX gene. The BclI site in the T allele is indicated. The sequences shown are of the anti-sense strand. The allele specific oligonucleotides are named as follows: gene designation—region of gene (number of the 5' base corresponding to the published sequence)—length of the oligonucleotide, upstream or downstream orientation (identity of the bases(s) which determines specificity and distance form the 3' end of the oligonucleotide). For sequences without polymorphisms or mutations, the last parenthesis in the notation is omitted. The region of the gene is abbreviated by U: upstream of the gene, E: exon number, I: intron number, and D: downstream of the gene. The numbering system for Factor IX corresponds to that of Yoshitake, et al., 7 For example, F9-E1 (61)-15U($A^{n-1}$) is a Factor IX oligonucleotide in exon 1 whose 5' base corresponds to position 61. The oligonucleotide is 15 bases long and is upstream in orientation relative to the direction of transcription. It has the A allele sequence one base form the 3' end. Another example is PH-E12 (1528)-16D($A^{n-5}$) which is a phenylalanine hydroxylase oligonucleotide that begins in exon 12 at base 1528. The oligonucleotide is 16 bases in length and downstream in orientation with respect to transcription. It has the A allele sequence five bases from the 3' end.

Figure 17:
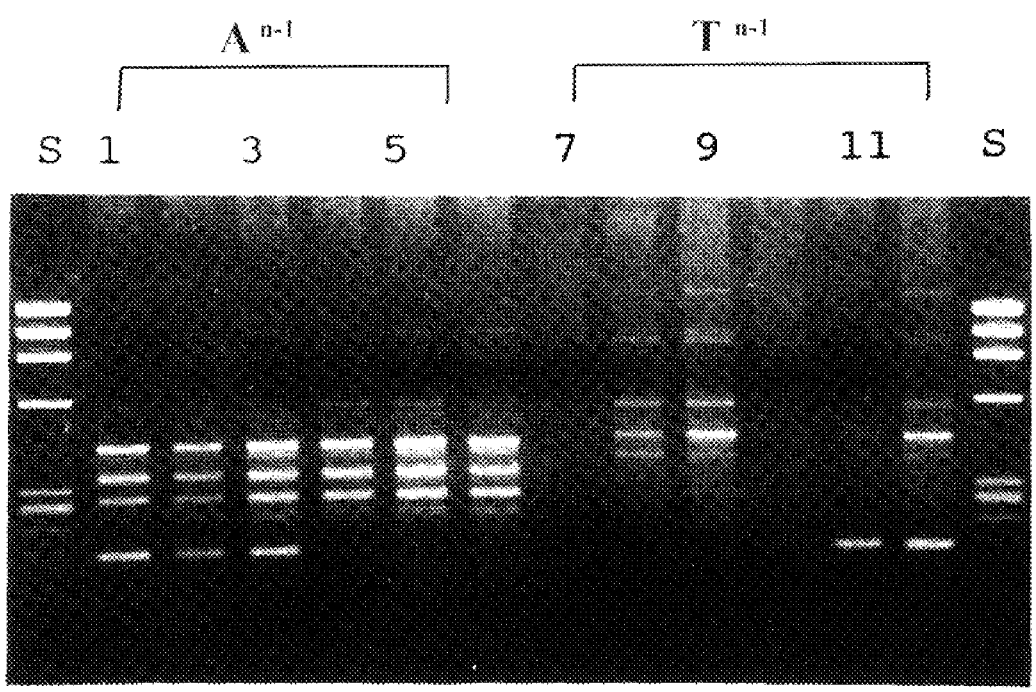
FIG. 17: Effects of $Mg^{++}$ concentration on PASA specificity.

If 15($A^{n-1}$) was used, specific amplification occurred from E91M genomic DNA but not from E100M genomic DNA (FIG. 17). Surprisingly, the difference was qualitative since it was not possible to get the 182 bp amplification product from E100M even if the stringency of the PCR was markedly reduced (FIG. 17). In contrast, three spurious amplification products of other sizes were consistently seen in E100M. It is inferred that these products are due to cross-hybridization with genomic sequences that differ at the 5' end of 15($A^{n-1}$). This inference is supported by the observation that multiple 5' mismatches can be tolerated better than one 3' mismatch (see below).

FIG. 17 shows the effects of $Mg^{++}$ concentration on PASA specificity. PCR was performed using DNA from E91M, a male with the A allele, and from E100M, a male with the common T allele. Oligonucleotides specific for the allele [F9-E1(61)-15U($A^{n-1}$) and F9-U(-121)-15D] were used with DNA from E91M (Lanes 1–3) and E100M (Lanes 4–6). Oligonucleotides specific for the T allele [F9-E1(61)-15U ($T^{n-1}$) and F9-U(-121)-15D] were used with DNA from E91M (Lanes 7–9) and E100M (Lanes 10–12). S=Standards: 250 ng φX174 HaeIII restriction fragments: Lanes 1,4,7,10: 1.5 mM $Mg^{++}$; Lanes 2,5,8,11: 2.0 mM $Mg^{++}$; Lanes 3,6,9,12: 3.0 mM $Mg^{++}$. The arrow indicates the size of the expected amplified segment.

When the oligonucleotide specific for the common allele 15($T^{n-1}$), was used with F9-U(-121)-15D, the expected 182 bp amplification product was obtained from the E100M genomic DNA but not from E91M (FIG. 17). Again, there was specificity over a wide range of stringencies.

A series of 15-mers was synthesized to test the effect of the mismatched position on specificity. $A^n$ showed excellent specificity (Table 5). $A^{n-2}$ and $A^{n-4}$ showed quantitative, but not qualitative specificity. $A^{n-7}$ showed no specificity. It was subsequently discovered that $A^{n-2}$ had inadvertently been synthesized with an additional C to T mismatch 10 bases from the 3' end and a T to C mismatch 11 bases from the 3' end. The fact that the $A^{n-2}$ oligonucleotide still retained some specificity highlights the greater flexibility of the sequence at the 5' end.

TABLE 5

Comparison of Oligonucleotide Length and Point of Mismatch.[a]

| OLIGONUCLEOTIDE | E91M[b] | E100M[b] | [$Mg^{++}$] Window[c] |
|---|---|---|---|
| F9-E1(61)-15U($T^{n-1}$) | − | + | >2 mM |
| F9-E1(61)-15U($A^{n-1}$) | + | − | >2 mM |
| F9-E1(61)-15U($A^n$) | + | − | >2 mM |
| F9-E1(60)-15U($A^{n-2}$, $C^{n-10}$,$T^{n-11}$) | + | + | 1.0 mM |
| F9-E1(58)-15U($A^{n-4}$) | + | + | 0.7 mM |
| F9-E1(55)-15U($A^{n-7}$) | + | + | 0.2 mM |
| F9-E1(61)-14U($A^n$) | + | − | >2 mM |
| F9-E1(60)-13U($A^n$) | + | − | >2 mM |
| F9-E1(59)-12U($A^n$) | − | − | |

[a]PASA was performed as detailed in the specification using the indicated oligonucleotides and F9-U(-121)-15D. E91M has the single T -> A transversion at base pair 48; E100M has the common sequence.
[b]minus (−) indicates that no amplification of the 182 bp segment occurred at the $Mg^{++}$ concentrations tested.
[c][$Mg^{++}$] Window is the difference in minimum $Mg^{++}$ concentrations required for amplification of the 182 bp segment in E91M vs. E100M.

The effect of oligonucleotide length on specificity was tested by using the oligonucleotides 14($A^n$), 13($A^n$), and 12($A^n$). There was PCR amplification of specific alleles using 14($A^n$) (Table 5). Specificity could also be achieved with 13($A^n$), but magnesium concentrations greater than 4.5 mM were required. No specific amplification was seen with 12($A^n$) even at 5 mM $Mg^{++}$.

Figure 18:
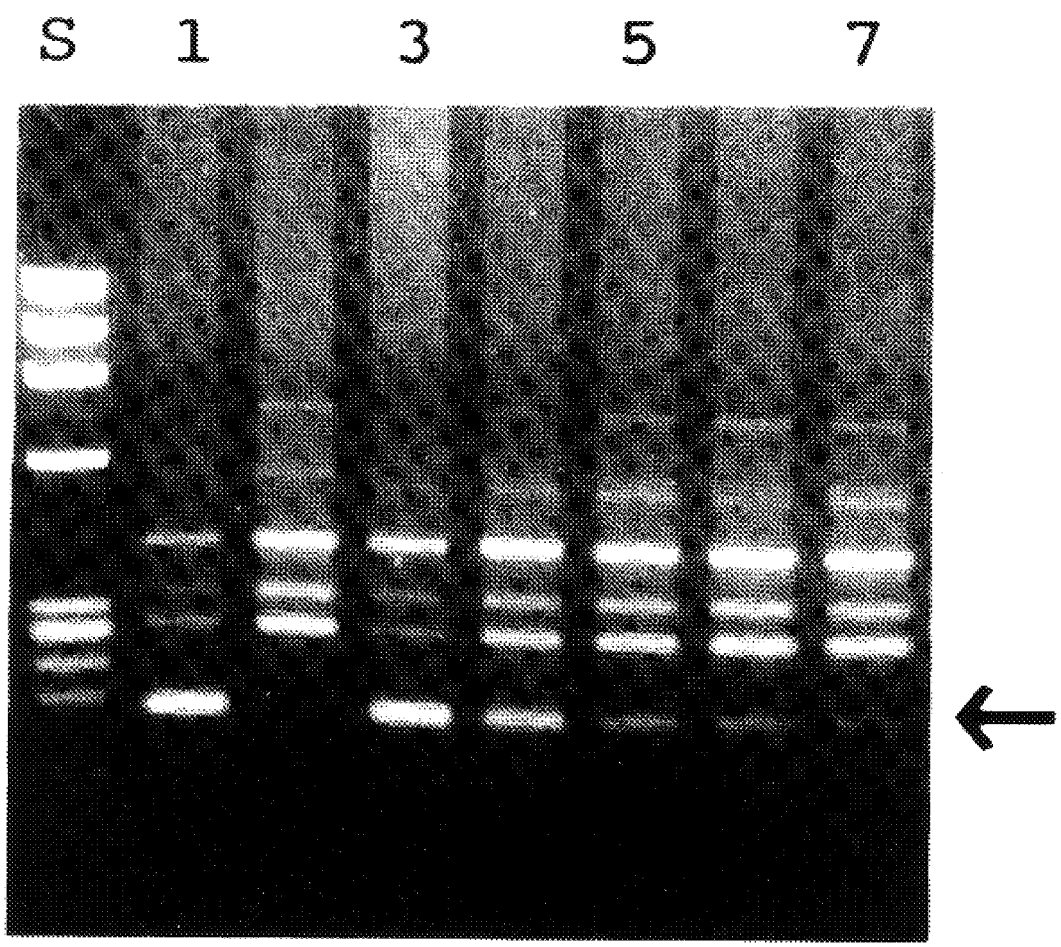
FIG. 18: Effects of Allele concentration on PASA specificity.

To determine if multiple genomic samples could be simultaneously analyzed, 250 ng of E100M genomic DNA were mixed with decreasing concentrations of E91M genomic DNA, and amplified with 15($A^{n-1}$) (FIG. 18). With as little as 6.25 ng of genomic DNA from E91M, a specific product could be seen. At 12.5 ng of E91M genomic DNA, the relative efficiency of amplification was enough to produce a 182 bp band almost as intense as produced by the spurious bands from the 250 ng of E100M DNA. This suggests that PCR should be viewed as a series of competing amplifications. If one reaction is slightly more efficient than another, the exponential nature of PCR preferentially shunts nucleotide substrates into the more efficient reaction. Multiple experiments have confirmed the specificity of amplification that exists when there is a precise match.

FIG. 18 shows the effects of allele concentration on PASA specificity. PASA was performed using the A allele specific oligonucleotides [F9-E1(61)-15U($A^{n-1}$) and F9-U(-121)-15D] with decreasing concentration of E91M DNA in the presence of 250 ng of E100M DNA. S=Standards; 250 ng φX174 HaeIII restriction fragments. Lane 1: E91M (250 ng); Lane 2: E100M (250 ng); Lane 3: E91M/E100M (250 ng/250 ng); Lane 4: E91M/E100M, (83 ng/250 ng); Lane 5: E91M/E100M, (25 ng/250 ng); Lane 6: E91M/E100M, (12.5 ng/250 ng); Lane 7: E91M/E100M, (6.25 ng/250 ng). The arrow indicates the size of the expected amplified segment.

For population screening of the E91M allele, mixtures of genomic DNA from 4 individuals were amplified with F9-U(-121)-15D and 15($A^{n-1}$). Spurious amplification products seen in individuals who lack this allele provided an internal positive control for a successful PCR reaction. Results obtained with PASA were confirmed by an alternate PCR amplification with the oligonucleotides F9-U(-239)-15D and F9-I1(157)-47U, followed by the restriction digestion of the PCR products with BclI. The presence of the E91M allele was determined by the absence of the BclI site. Over four hundred chromosomes were screened by PASA and none of them contained the E91M allele, indicating that it represents a rare variant rather than a polymorphism.

Screening for PKU Alleles

In order to screen for carriers of PKU, oligonucleotides for the mutant haplotypes 2 and 3 were synthesized. PH-E12 (1432)-14D($T^{n-1}$) corresponds to the C to T transition at $trp^{408}$ in exon 12 (haplotype 2) and PH-E12(1524)-16D($A^{n-1}$) corresponds to the G to A transition in the intron 12 splice junction (haplotype 3). These oligonucleotides, which mismatch the normal alleles at the penultimate 3' base, were tested in a PKU proband, individual #6 (FIG. 19A). individual #6 is a compound heterozygote for both mutations as determined by GAWTS. For PH-E12(1524)-16D(A-$^{n-1}$), a faint spurious PCR amplification product was seen near the size of the specific product. Therefore, PH-E12(1522)-17D ($A^n$) was used in subsequent experiments. PH-E12(1528)-16D($A^{n-5}$) was also synthesized, but had little specificity. This provides further evidence of the importance of a mismatch near the 3' end of the oligonucleotide.

Figure 19A:
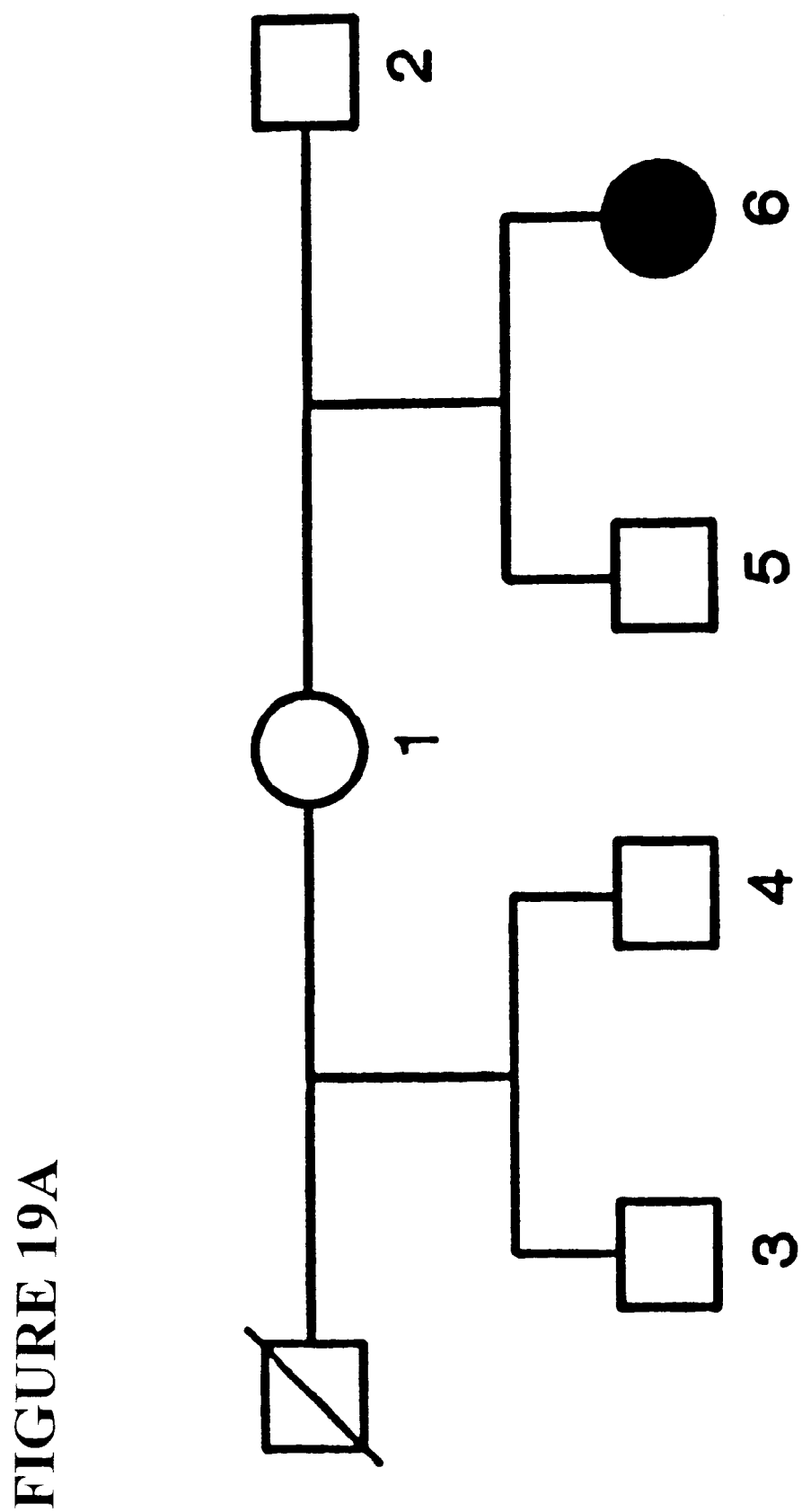
FIG. 19A: PKU carrier testing with PASA showing a pedigree of the family of the PKU proband individual #6.
Figure 19B:
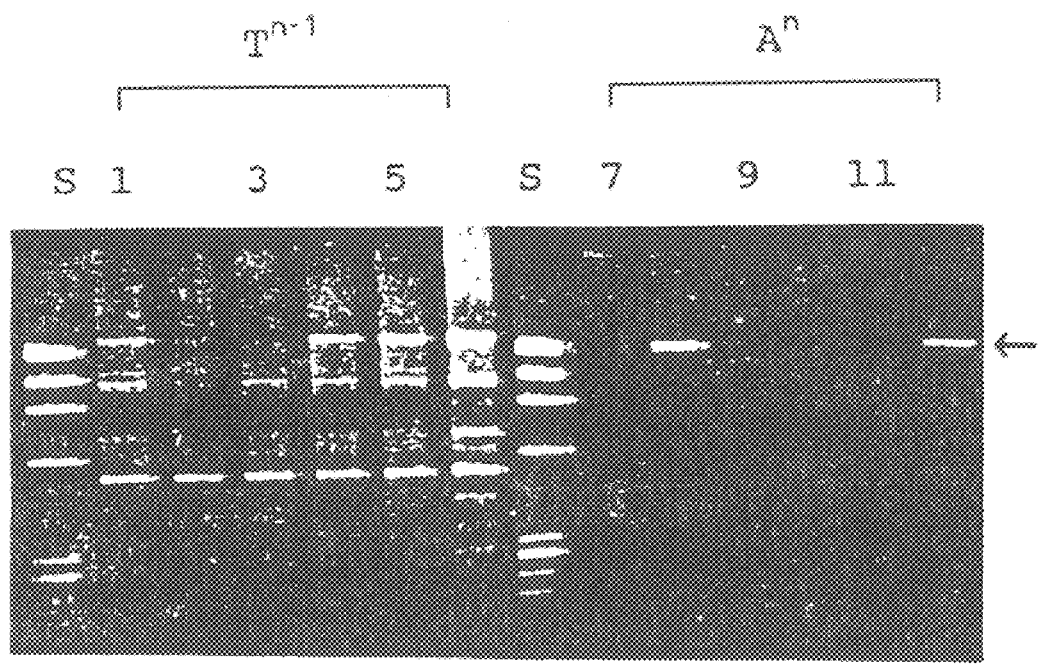
FIG. 19B: PKU carrier testing with PASA showing PASA for 2 PKU mutations.

PASA was used to perform carrier testing in the family of individual #6 (FIG. 19B). The results, which were confirmed by sequencing with GAWTS, indicated that the mother, brother, and one half-brother carry the $trp^{408}$ mutation, while the father carries the splice junction mutation.

FIG. 19 shows PKU carrier testing with PASA. PASA was performed using oligonucleotides specific for the mutation at $trp^{408}$[PH-E12(1432)-14D($T^{n-1}$) and PH-E13(1626)-46U] or the mutation at the intron 12 splice junction [PH-E12(1522)-17D($A^n$) and PH-E13(1626)-46U]. The oligonucleotide concentrations were 0.25 μM and 0.05 μM, respectively. FIG. 19A shows a pedigree of the family of the PKU proband individual #6, a compound heterozygote for these two mutations. FIG. 19B shows PASA for 2 PKU mutations. S=Standards; 250 ng φX174 HaeIII restriction fragments: Lanes 1–6: PASA for detection of the $trp^{408}$ mutation in individuals #1–6, respectively; Lanes 7–12: PASA for detection of the intron 12 splice junction mutation in individuals #1–6, respectively. The arrow indicates the size of the expected amplified segment. The numbering system for PAH corresponds to that of Kwok, et al. Kwok, et al. (1985)], The sequence of PH-E12(1432)-14D($T^{n-1}$) is GCCACAATACCT<u>T</u>G. The sequence of PH-E12(1522)-17D($A^n$) is GCTGATTCCATTAACA<u>A</u>.

Figure 20:
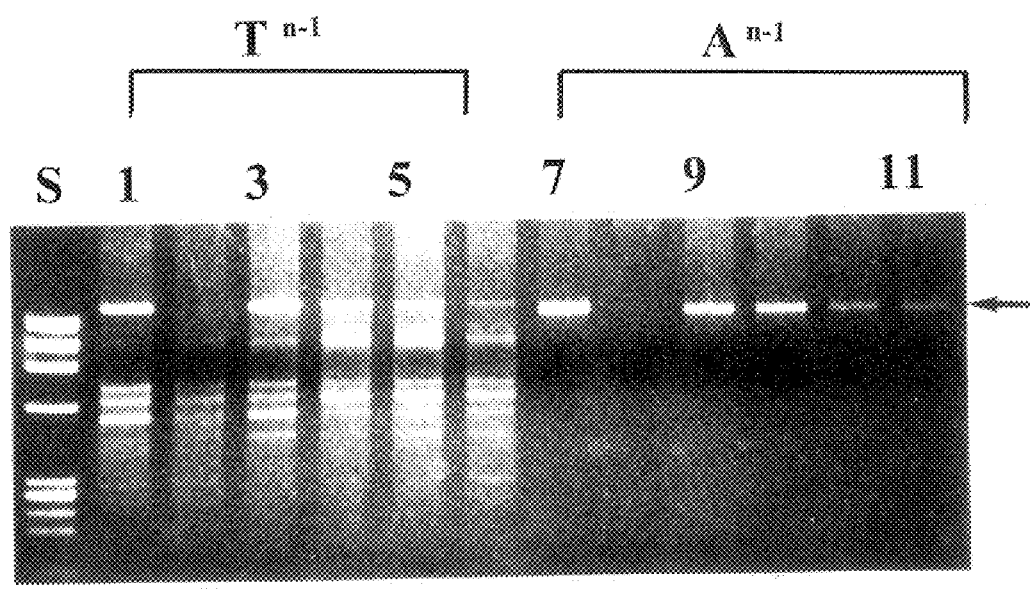
FIG. 20: Detection of PKU mutations in the presence of an excess of normal alleles.

In preparation for population screening for these two mutations, DNA from multiple individuals was mixed and analyzed by PASA. Each of the mutations could be detected in the presence of at least 39 normal alleles (FIG. 20). Six hundred chromosomes from unrelated individuals with no known family history of PKU were screened in groups of 4 individuals with PH-E12(1432)-14D($T^{n-1}$). No carriers of the $trp^{408}$ mutation were found. For each group of 4, a second PCR was performed with a spike of genomic DNA from the PKU proband, individual #6, in order to verify that the mutation would have been detected had it been present (FIG. 21A).

FIG. 20 shows detection of the PKU mutations in the presence of an excess of normal alleles. PASA was performed using decreasing concentrations of DNA from individual #6 in the presence of 250 ng of DNA from a normal individual (E102F). The oligonucleotide concentrations were 0.25 μM for [PH-E13(1626)-46U and [PH-E12(1432)-14D($T^{n-1}$)] and 0.10 μM for [PH-E13(1626)-46U and [PH-E12(1522)-17D($A^n$)]. In Lanes 1–6, 14($T^{n-1}$) was used for screening and Lanes 7–12, 17($A^n$) was used. S=Standards; 250 ng φX174 HaeIII restriction fragments. Lanes 1,7: #6 (250 ng); Lanes 2,8: E102F (250 ng); Lanes 3,9: #6/E102F, (250 ng/250 ng); Lanes 4,10: #6/E102F, (62 ng/250 ng); Lanes 5,11: #6/E102F, (25 ng/250 ng); Lanes 6,12 #6/E102F, (12.5 ng/250 ng). The arrow indicates the size of the expected amplified segment.

Figure 21A:
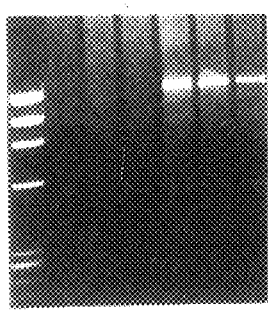
FIG. 21A: Screening of population for PKU carrier with PASA, specifically screening for the $trp^{408}$ mutation in Exon 12.
Figure 21B:
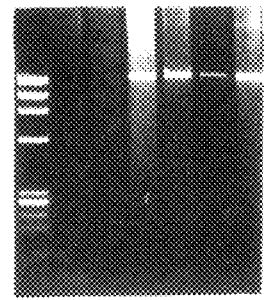
FIG. 21B: Screening of population for PKU carrier with PASA, specifically screening for intron 12 splice junction mutation.

FIG. 21 shows screening a population for PKU carriers with PASA. FIG. 21A shows screening for the $trp^{408}$ mutation in exon 12. PASA was performed on groups of 4 individuals (50 ng DNA each) with oligonucleotides PH-E13(1626)-46U and PH-E12(1432)-14D($T^{n-1}$) at concentrations of 0.25 μM each. As a positive control, PASA was repeated with each group after adding 50 ng of DNA from individual #6. S=Standards; 250 ng φX174 HaeIII restriction fragments. Lane 1: Group 1; Lane 2: Group 2; Lane 3: Group 3; Lane 4: Group 1+#6; Lane 5: Group 2+#6; Lane 6: Group 3+#6. FIG. 21B shows screening for the intron 12 splice junction mutation. PASA was performed on groups of 4 individuals (50 ng DNA each) with and without DNA from individual #6 (50 ng). Oligonucleotide concentrations of PH-E13(1626)-46U and PH-E12(1522)-17D ($A^n$) were 0.05 μM each. S=standards; 250 ng φX174 HaeIII restriction fragments; Lane 1: Group 1; Lane 2: Group 2; Lane 3; Group 3; Lane 4: Group 1+#6; Lane 2: Group 2+#6; Lane 3; Group 3+#6. Identifying the PKU carrier in Group 3. Using oligonucleotides PH-E13(1626)-46U and PH-E12 (1522)-17D($A^n$) at 0.05 μM each, DNA (250 ng) from each individual in Group 3 was screened by PASA, S=Standards; 250 ng φX174 HaeIII restriction fragments: Lane 1: N5; Lane 2: N6; Lane 3: N7; Lane 4: NB. The arrows indicate the size of the expected amplified segment.

Figure 21C:
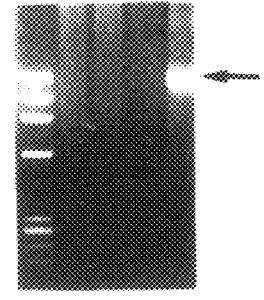
FIG. 21C: Screening of population for PKU carrier with PASA, specifically screening for the PKU carrier in group 3.

One hundred chromosomes were also screened with PH-E12(1522)-17D($A^n$) and one carrier of the intron 12 splice junction mutation was found in Group 3 (FIG. 21B). The carrier, NB, was identified from Group 3 by 4 individual PCR allele specific amplifications (FIG. 21C). Sequence analysis by GAWTS verified that this individual had the corresponding G to A transition (FIG. 22).

Figure 22A:
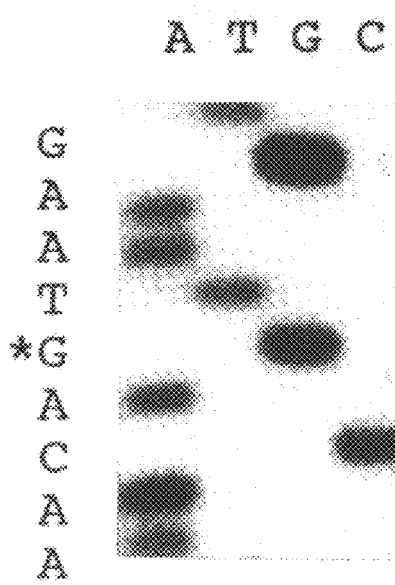
FIG. 22A: Sequencing of the PXU intron 12 splice junction mutation by GAWTS for individual #3, a non-carrier.
Figure 22B:
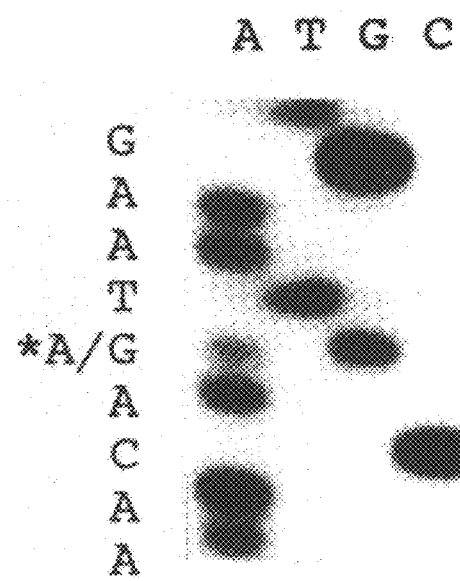
FIG. 22B: Sequencing of the PKU intron 12 splice junction mutation by GAWTS for NB, a carrier.

FIG. 22 shows sequencing of the PKU intron 12 splice junction mutation sequencing performed by GAWTS. The oligonucleotides used for the PCR amplification step of GAWTS were PH-E13(1626)-46U and PH-I11(-17)-17D. The nested (internal) sequencing primer was PH-E12(1420)-16D. FIG. 22A shows an individual #3, a non-carrier (Also see FIG. 19B); FIG. 22B shows N8, a carrier (Also see FIG. 20C). The asterisk indicates the point of mutation in the intron 12 splice junction.

Figure 23:
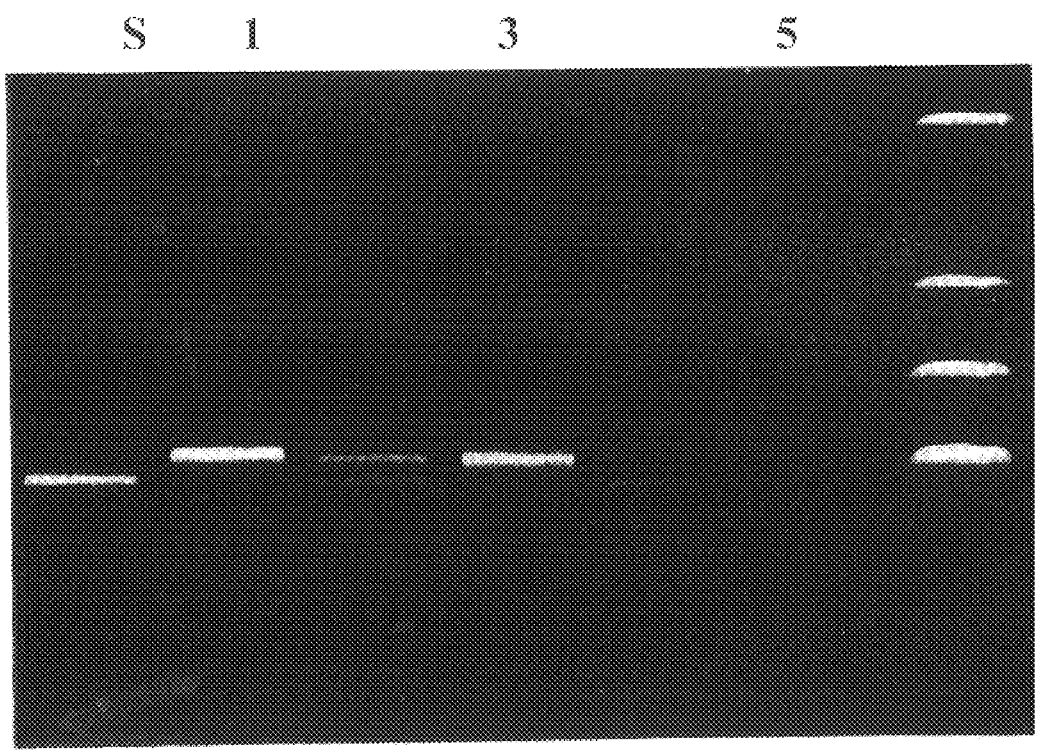
FIG. 23: Simultaneous detection of two PKU mutations with PASA.

Since future screening would benefit by simultaneous detection of the two mutations, both specific oligonucleotides PH-E12(1432)-14D($T^{n-1}$) and PH-E12(1522)-17D ($A^n$) were included with PH-E13(1626)-46U during PCR. Although the oligonucleotide concentrations had to be adjusted to obtain equal amplification, specificity was achieved (FIG. 23). Individual #6, the compound heterozygote PKU proband, had the two expected PCR products from the simultaneous PASA. The appropriate single PCR product was observed for carriers of the $trp^{408}$ and intron 12 splice junction mutations, and no specific products were observed for non-carriers.

FIG. 23 shows simultaneous detection of the two PKU mutations with PASA. PASA was performed with PH-E13 (1626)-46U and one or both PH-E12(1432)-14D($T^{n-1}$) and PH-E12(1522)-17D($A^n$). Oligonucleotide concentrations were 0.10 μM each. S=standards: 250 ng φX174 HaeIII restriction fragments; Lane 1: 14($T^{n-1}$) and 17 ($A^n$), DNA from E102F (non carrier); Lane 2: 14($T^{n-1}$); DNA from individual #6 (carrier of the both mutations); Lane 3: 17($A^n$), DNA from individual #6; Lane 4: 14($T^{n-1}$)+17($A^n$), DNA from individual #6; Lane 5: DNA from individual #2 (carrier of the intron 12 splice junction mutation); Lane 6: 14($T^{n-1}$)+17($A^n$), DNA from individual #1 (carrier of the $trp^{408}$ mutation).

Once sequence becomes available for intron 11, it should be possible to obtain better resolution between the haplotype 2 and 3 alleles by performing simultaneous PASA for the C to T mutation with an intron 11 primer and an allele specific primer oriented in the other direction. However, it was important to show that the simultaneous amplification of two overlapping segments could be performed (FIG. 23), as this may be necessary if additional PKU alleles map to exon 12.

Discussion

PCR amplification of specific alleles (PASA) uses allele specific oligonucleotides to differentially amplify alleles with the polymerase chain reaction. If the base which is specific for the allele is near the 3' end of the PCR primer, the relevant allele will be amplified and then can be detected by agarose gel electrophoresis from a mixture of genomic DNA with a 40-fold excess of the other allele. This technique was used to examine the frequency of a single base pair change observed in the Factor IX gene of an individual without apparent coagulopathy. Over 400 chromosomes were screened with PASA for this change. No other individual was found with this allele, indicating that this change occurs in less than 1% of the population. Therefore, this allele is a rare variant rather than a new polymorphism.

PASA was used in the carrier testing of a family where the proband is a compound heterozygote for two known point mutations associated with PKU. PASA was also applied in screening a population of northern European descent for these two mutations. The first mutation, the C to T transition at amino acid 408, occurs in approximately one of 500 chromosomes. [Chakraborty, et al. (1987)]. Although more than 600 chromosomes were screened, no carriers were identified. Given the frequency of this mutation, these results are not surprising.

In screening 100 chromosomes for the second PKU mutation at the exon 12/intron 12 splice junction, one carrier was identified. Carrier status was verified by direct sequencing and the individual was shown to have the G to A transition. Although this mutation has been reported to occur in approximately one of 200 chromosomes. [Realmuto, et al. (1986)], a large enough sample size to verify this frequency has not yet been screened.

For the 3 allele pairs (1 transversion and 2 transitions) that were tried with PASA, few difficulties in optimization were encountered.

Specific amplification was obtained over a range of stringencies if the oligonucleotides had the allele specific base near the 3' end. In occasional DNA samples, amplification did not occur under standard conditions. This was evidently due to the contamination of genomic DNA with EDTA, [Gustafson, S., J. A. Proper, E. J. W. Bowie, S. S. Sommer, Anal. Biochem., 165:294–299 (1987)] since higher concentrations of Mg++ resolved these problems.

PASA provides a rapid and general method for detecting mutations and polymorphisms (including RFLPs). PASA holds particular promise for population screening. The test is accurate, reproducible, and generates unequivocal results. Many individuals can be screened simultaneously and the cost of supplies and labor are relatively low (approximately $1.00/PASA reaction). The method involves techniques that inexperienced personnel can quickly master. Partial automation already exists with automated thermal cyclers and complete automation is feasible.

PCR followed by hybridization with allele-specific oligonucleotides [DiLella, et al., (1988)] is an alternative to PASA for detecting single base changes. However, PASA has a number of advantages for population screening: 1) the test is qualitative rather than quantitative; 2) 40 or more chromosomes can be screened simultaneously; 3) multiple distinct alleles can be analyzed simultaneously in one lane of a gel; and 4) automation of PASA may be easier to achieve because there are fewer steps involved.

The subject invention shows that spurious bands can serve as an internal control for the effectiveness of the PCR, and that two PKU mutations can be detected simultaneously. Others have shown that six simultaneous PCR reactions can be performed. (Chamberlain, J. S., R. A. Gibbs, J. E. Ranier, P. N. Nguyen, C. T. Caskey., Nucleic Acid Res., 16:11141–11156 (1988)] Thus it is likely that the four to six mutations that account for 90% of the PKU alleles in the U.S. Caucasian population potentially could be screened with one internally controlled PASA reaction. If 25 individuals are screened per tube, one-half of the tubes on average will contain DNA from a carrier. By consecutively subdividing the sample, 11 PASA reactions will suffice to identify one carrier. By also combining the tubes that are positive for different mutations, 12 reactions on the average can detect 2 or more carriers. Therefore, 22 million PASA reactions at approximately 22 million dollars in labor and supplies would be required to screen the U.S. population. The cost of PASA would not be limiting, as the collection of blood and extraction of DNA and the subsequent counseling of individuals would be far more expensive. However, once DNA is collected, subsequent screening for other genetic diseases would entail only the incremental costs of PASA reactions and patient counseling.

PASA offers a promising approach for population screening in PKU and other diseases such as sickle cell anemia and the thalessemias. As mutations are identified in diseases such as cystic fibrosis, neurofibromatosis, and Huntington's disease, it may also be possible to screen by PASA for carrier status in these diseases.

More than 100,000 bp of sequence have been generated by GAWTS from eight regions of the factor IX gene which include the putative promoter region, the coding region, and the spice junctions. All eight regions were examined in 20 unrelated normal individuals of defined ethnicity and subsequently in 22 hemophiliacs in different families. Three major conclusions emerge: (1) The rate of polymorphism in these eight regions of functional significance has been measured in an X-linked gene and it is about one-third of the average rate observed for intronic and intergenic sequences on the X chromosome. The rate is low enough that the causative mutation should be the only sequence change seen in the overwhelming majority of hemophiliacs. (2) Transitions at CpG account for 31% (5/16) of the distinct mutations and 38% (5/13) of the single-base changes. The rate of transitions at CpG is elevated by an estimated 77-fold presumably due to lack of repair of thymidine generated by the spontaneous deamination of 5-methylcytidine. (3) High quality, reproducible sequence data can be obtained on a time scale that makes direct carrier testing and prenatal diagnosis feasible.

The recent developments of methodolgy for direct sequence makes it technically feasible to measure the rate of polymorphism in exons and other sequences of likely functional significance [Wong C., C. E. Dowling, R. K. Saiki, R. G. Higuchi, H. A. Erlich, H. G. Kazazian, Jr., Nature, 330:384–386 (1987); Stoflet E. S., D. D. Koberl, G. Sarkar, S. S. Sommer, Science, 239:491–494 (1988); Engelke D. R., P. A. Hoener, F. S. Collins, Proc. Natl. Acad. Sci. USA, 85:544–548 (1988); Gyllensten U. B. and H. A. Erlich, Proc. Natl. Acad. Sci. USA, 85:7652–7656 (1988)]. Previously, it had only been possible by Southern blots to estimate the average rate of polymorphism in the intronic and intergenic sequence that constitutes the overwhelming majority of the human genome. (Hofker M. H., M. C. Wapenaar, N. Goor, E. Bkker, G. J. B. van Ommen, P. L. pearson Hum Gent, 70:148–156 (1985); Aldridge J., L. Kunkel, G. Bruns, Am. J. Hum. Genet. 36:546–564 (1984)]. The results indicate that the average rate of polymorphism on the X chromosome (HE) is approximately one-third that of the autosomes. By utilizing GAWTS regions of likely functional significance in the factor IX genes of multiple normal individuals of predominantly Western European descent. The data provide the first estimate of the rate of polymorphism in such regions Direct sequencing also makes it feasible to delineate point mutations in multiple individuals. For an X-linked lethal disease, direct sequencing can provide a "snapshot" of recent mutations in the population because the mutations that arise are extinguished within a few generations [Haldane, J. B. S., Genet, 31:317–326 (1935)]. Analysis of such data should reveal whether any hotspots of mutation exist. Previously protein and nucleic acid sequence of hundreds of variant α- and β-globin alleles did not reveal any dramatic hotspots in these autosomal genes [Vogel, F. and A. G. Motulsky (eds) In: Human Genetics. Edition 2, Springer-Verlag, Berlin, pp. 433–511, (1986)]. Notably, transitions of CpG were not markedly elevated. More recently the delineation of mutations in other genes has indicated that transitions at CpG occur with great frequency [Youssoufian, H., H. H. Kazazian, Jr., D. B. Phillips, S. Aronis, G. Tsifitis, V. A. Brown, S. E. Antonarkis, Nature, 324:380–382 (1986); Youssoufian, H., S. E. Antonarakis, W. Bell, A. M. Griffin, H. H. Kazazian, Jr., Am. J. Hum. Genet., 42:718–725 (1988); Vulliamy T. J., M. D. Urso, G. Battistuzzi, M. Estrada, N. S. Foulkes, G. Martini, V. Calabro, V. Poggi, R. Giordana, M. Town, L. Luzzato, M. G. Persico, Proc. Natl. Acad. Sci. USA, 85:5171–5175 (1988); Cooper D. N. and H. Youssoufian, Hum. Genet., 78:151–155 (1988)]. Eight regions of likely functional significance in 21 hemophiliacs from different families have been sequenced. The results of this large sample of germline mutations from a single gene show that CpG is a hotspot of mutation in the factor IX gene and that the rate of enhancement is about 77-fold. This enhancement is not restricted to a particular subset of CpGs with constant bases in the immediately flanking sequence.

The present results also pertain to the carrier testing and prenatal diagnosis of hemophilia B. The current RFLP-based carrier testing has multiple problems which include: 1) a 20% chance in Caucasians and a much higher probability in other population of not finding an informative polymorphism [Winship P. R., G. G. Brownlee, Lancet, ii:218–219 (1984); Hay C. W., K. A. Robertson, S-L Yong, A. R. Thompson, G. H. Growe, R. MacGillivray, Blood, 67:1508–1511 (1986); Lubahn D. B., S. T. Lord, J. Bosco, J. Kirshtein, O. J. Jeffries, N. Parker, C. Levtzow, L. M. Silverman, J. B. Graham, Am. J. Hum. Genet., 40:525–536 (1987)]; (2) uncertainty of diagnosis due to the possibility of hotspots o recombination nonpaternity germline mosaicism, genetic heterogeneity, and new mutations in the recent past; and (3) necessity of participation by multiple family members in addition to the at-risk individuals and the one affected family member. The results herein show that sequencing 2.46 kb in eight regions of the factor IX gene is sufficient to delineate the overwhelming majority of mutations. The mutations will be the only sequence change found in the overwhelming majority of hemophiliacs, allowing direct, accurate and rapid testing to be performed by sequencing the relevant regions of at-risk individuals in the family.

Materials and Methods

Twenty-four ml of blood was drawn in ACD solution B and DNA was extracted as previously described [Gustafson S., J. A. Proper, E. J. W. Bowie, S. S. Sommer, Anal Biochem 165:294–299 (1987)]. GAWTS was performed in three steps:

1. PCR: 400 ng of genomic DNA in 1 was added to 40 µl of 50 mM KCl, 10 mM Tris-HCl (pH 8.3), 1.5 mM $MgCl_2$, 0.01% (w/v) gelatin, 200 µM each DNTP, 1 µM of each primer (Perkins Elmer Cetus protocol). After 10 min 94° C., 1 U of Taq polymerase was added and 35 cycles of PCR were performed (annealing: 2 min. at 50° C.; elongation: 3 min at 72° C.; denaturation: 1 min at 94° C.) with the Perkin Elmer Cetus automated thermal cycler. One primer included a T7 promoter as described above. A final 10 min elongation step was performed after the 35th cycle.

2. Transcription: 3 µl of the amplified material was added to 17 µl of the RNA transcription mixture: 40 mM Tris HCl, pH 7.5, 6 mM $MgCl_2$, 2 mM spermidine, 10 mM sodium chloride, 0.5 mM of the four ribonucleoside triphosphates, RNasin (1.6 U/µl), 10 mm DTT, 10 U of T7 RNA polymerase, and diethylpyrocarbonte treated $H_2O$. Samples were incubated for 1 hour at 37° C. and the reaction was stopped with 5 mM EDTA.

3. Sequencing: 2 µl of the transcription reaction was added to 10 µl of annealing buffer containing the end-labeled reverse transcriptase primer. Annealing and sequencing with reverse transcriptase were performed as described above, but with only 1U of reverse transcriptase.

Base pairs sequenced. The numbering system corresponds to Yoshitake et al. (1985). Region A: −106 to 139. Region B/C: 6720 to 6265. Region D: 10544 to 10315. Region E: 17847 to 17601. Region F: 20577 to 20334. Region G: 30183 to 29978. Region H-5': 31411 to 30764. Region H-3' 32808 to 32583. The order of numbers in each region indicates the direction of sequencing. Due to technical difficulties, a variable number of the first ten bases on each region was not obtained in some individuals. At least 2460 bp of sequence were obtained on each individual.

Results

The factor IX gene is 34 kb with seven introns that account for over half the exonic sequence [Anson D. S., K. H. Choo, D. J. G. Rees, F. Giannelli, J. A. Gould, G. G. Brownlee, EMBO J., 3:1053–1060 (1984); Yoshitake S., B. G. Schach, D. C. Foster, E. W. Davie, K. Kurachi Biochemistry, 24:3736–3750 (1985)]. For this study, eight regions encompassing 2.46 kb of sequence were chosen for sequencing. The exonic sequences include the entire coding sequence (1383 bp), the 5' untranslated sequence, and portions of the 3' untranslated segment (497 bp). Region A contains the putative promoter, exon a, and the adjacent splice junction. Region B/C contains exon b, intron b, exon c, and the flanking splice junctions. Region D through G contain the appropriate exon and flanking splice juntions. Region H-5' contains a splice junction, the amino acid coding sequence of exon h and the proximal 3' untranslated segment of the mRNA. Region H-3, contains the distal 3' untranslated region in exon h (including the poly A addition sequence) as well as the sequence immediately following the gene. It was anticipated that the overwhelming majority of causative mutations in individuals with hemophilia B would lie in these regions.

Sequence Changes in Unaffected Males

To help interpret the sequence changes that might be seen in hemophiliacs and to quantitate the rate of polymorphism in an X-linked gene, these regions were first sequenced in 20 unrelated, unaffected individuals including 18 of European descent, 1 Asian Indian, and 1 Lebanese Arab. Examination of 49 kb of sequence revealed the previously described Malmo [McGraw, R. A. L. M. Davis, C. M. Noyes, R. L. Lundblad, H. R. Roberts, J. B. Graham, D. W. Stafford, Proc. Natl. Acad. Sci. USA, 82:2847–2851 (1985); Winship and Brownlee, 1986] high-frequency polymorphism (minor allele present at 20%). In addition in one individual, E91M, an A→T transversion was found at nucleotide 48 which substitutes phenylalanine for isoleucine −40 in the signal peptide (table 6). As described below, this change (which we name the bp48T allele) has a frequency of less than 1% which defines it as a rare variant rather than a polymorphism.

unaffected individuals. Subsequently oligonucleotides specific for the bp48T and the normal alleles were synthesized and 350 additional unaffected chromosomes were tested. The bp48T allele did not recur so it is likely to be a rare variant as estimated by the binomial distribution (probability of 0.027 for 0 recurrences in 360 consecutive chromosomes given a true frequency of 1% which is the lower limit for a polymorphism). Given the rarity of bp48T, efforts are now underway to obtain additional blood from E91M in order to measure factor IX coagulant and factor IX antigen although the available medical record did not report a bleeding anomaly.

TABLE 6

SUMMARY OF SEQUENCE CHANGES

| Factor IX:C[1] | Family | Nucleotide change[2] | Nucleotide number[3] | Amino acid change | Domain | Transition at CpG |
|---|---|---|---|---|---|---|
| 32 | HB13 | A -> G | 13 | 0 | 5' untranslated | N |
|  | E91M | A -> T | 48 | ile$^{-40}$ -> phe | signal | N |
| 30 | HB2 | G -> A | 6461 | arg$^{29}$ -> gln | gla | Y |
| 4 | HB9 | A -> C | 6474 | gla$^{33}$ -> asp | gla | N |
| 12–16 | HB3, 4, 7 | G -> A | 10430 | gly$^{60}$ -> ser | growth factor | Y |
| 20 | HB6 | del TTCT | 17660-3 | 0 | acceptor splice junction of intron d | — |
| 4 | HB25 | G -> A | 20414 | arg$^{145}$ -> his | activation peptide | Y |
| <1 | HB23 | del AACC-ATTTTGGAT | 20466-78 | del & fs[4] after ala$^{161}$ | activation peptide | — |
| <1 | HB17 | C -> T | 20497 | gln$^{173}$ -> TAA | activation peptide | N |
| 1 | HB24 | T -> G | 30119 | cys$^{222}$ -> trp | catalytic | N |
| 30 | HB2 | T -> C | 30134 | val$^{227}$ unchanged[5] | catalytic | N |
| 12 | HB1 | G -> A | 30150 | ala$^{233}$ -> thr | catalytic | Y |
| 24 | HB8 | A -> G | 30900 | asn$^{260}$ -> ser | catalytic | N |
| <1 | HB19 | C -> T | 31008 | thr$^{296}$ -> met | catalytic | Y |
| 3 | HB26 | G -> A | 31052 | gly$^{311}$ -> arg | catalytic | N |
| <1–6 | HB, 11, 12 14, 16, 18 | T -> C | 31311 | ile$^{397}$ -> thr | catalytic | N |
| <1 | HB20 | T -> C | 31340 | trp$^{407}$ -> arg | catalytic | N |

[1]Factor IX coagulant as recorded in the patient record.
[2]change in the sense strand.
[3]Numbering system from Yoshitake et al.
[4]Combination of deletion and frameshift.
[5]Note additional change at $^{arg29}$.

Frequency of Polymorphism

To estimate the rate of polymorphism, the frequency of the Malmo polymorphism and the bp48T allele were quantitated. Although another polymorphism may possibly have been missed this is unlikely because (1) only males were used so a polymorphism results in both the absence of the expected sequencing band and the presence of a new band, (2) the sequencing reactions and/or gels were repeated if even one base in the gel was marginally resolved, (3) although prominent shadow bands occasionally occur, especially after contiguous thymidines, a change in sequence eliminates these shadow bands, and (4) sequence changes were found in the 21 hemophiliacs examined.

The threonine allele of the Malmo polymorphism was present at amino acid 148 in 13 normal and 12 independent hemophiliac chromosomes (71% of the total), while alanine was present in the remaining 7 normal and 3 hemophiliac chromosomes (29% of the total) [Smith, K. J., A. R. Thompson, B. A. McMullen, D. Frazier, S. Wha Lin, D. Stafford, W. Kisiel, S. N. Thibodeau, S-H Chen, L. F. Smith, Blood, 70:1106–1113 (1987)]. To quantitate the frequency of bp48T, Region A was sequenced in another 10 unrelated If the published sequence of these regions from two normal individuals and the partial sequence from five others are added to the present data [Kurachi K. and E. W. Davie, Proc. Natl. Aca. Sci. USA, 79:6461–6464 (1982); Jaye M. H. De La Salle, F. Schamber, A. Balland, V. Kohli, A. Findell, P. Tolstoshev, J-P Lecocq, Nucleic Acids Res., 11:2325–2335 (1983); Anson et al., 1984; Jagadewaran P., D. E. Lavelle, R. Kaul, T. Mohandas, S. T. Warren, Somatic Cell Mol. Genet. 10:465–473 (1984); McGraw et al. 1985; Yoshitake et al. 1985], one high frequency polymorphism and one rare variant were defined from an aggregate of 71 kb from normal individuals. The frequency of polymorphism can be estimated from these data by $H_N$, the probability that two homologous sequences will have different base pairs at a given site (i.e., the probability of being heterozygous at a base pair).

$H_N=1-[(a/b)^2+((b-a)/b^2]$ [Cooper D. N. and Schmidtke J., Hum Genet 66:1–16 (1984); Hofker et al. 1985] where a is the total number of variants and b is the total number of base pairs tested.

With the aggregate data, $H_N=0.00031=1/3225$. As some regions are more heavily represented, a more conservative estimate would include the sequence of only the 22 fully characterized normal individuals (includes our 20 individuals plus the two previously published individuals) where ten variants at two sites were found on sequencing 54 kb. In this case $H_N=0.00037=1/2700$.

Alternately, the frequency of polymorphism can be estimated by $H_E$, the fraction of sites in the haploid genome at which two nucleotide types appear.

$$H_E = \frac{V}{X} \quad \text{(Ewens et al. 1981, as modified for the analysis of hemizygous males).}$$

where V is the number of polymorphic sites observed (rare variants are not counted) and X is the number of base pairs screened per haploid genome. $H_E$ takes no account of allele frequencies. With aggregate data on these 22 fully characterized individuals. $H_E=0.00041=1/2460$.

The rate of polymorphism has previously been measured by Southern blots of restriction enzyme digest. When 40 randomly obtained autosomal probes and 82 randomly obtained X chromosomal probes were used, $H_N=0.0034$ and 0.0009, respectively, and $H_E=0.0043$ and 0.0014, respectively [Hofker et al. 1985]. Other estimates were similar [Cooper et al. 1985]; Aldridge et al. 1984). These estimates quantitate the variation in a limited number of sequences which constitute the recognition sites for the restriction endonucleases used in the survey. The sequences are almost exclusively intronic and intergenic in origin.

In contrast, the sequences in this study were exons and other regions likely to affect protein function. The low frequency of polymorphism observed suggest that these sequences are more highly conserved, but a more precise estimate of the rate of intronic and intergenic polymorphism in the region around factor IX must be made before a firm conclusion can be reached. However, the available data suggest that the 30 kb of the factor IX intronic sequence may well be more polymorphic than the average for the X chromosome because four high frequency polymorphines have already been found with the available restriction enzymes which only detect 2–5% of all existing polymorphisms [Winship, P. R., D. S. Anson, C. R. Rizza, G. G. Brownlee, Nucleic Acids Res. 12:8861–8872 (1984); Hay et al. 1986; Lubahn et al. 1987].

Sequence Changes in Hemophiliacs

Having documented the low rate of polymorphism in the eight regions of the factor IX gene, it was possible to embark upon the delineation of causative mutations in hemophilia with the expectation that the overwhelming majority of sequence changes would represent true mutations.

When these regions were examined 22 hemophiliacs, 1 large deletion was found and the remaining 21 mutations were precisely delineated (Table 6). Two of these were found again in the remaining six hemophiliacs, but haplotype analysis suggests that these mutations arose once in a common ancestor. This will be further discussed hereinbelow.

Of the 16 distinct mutations, one (HB5) was a deletion of most if not all of the gene as indicated by inability to amplify any of the regions in the absence of the expected bands when a Southern blot was performed with a total cDNA probe. Two additional mutations (HB6, 23) were deletions of 4 and 13 bases, respectively. The remaining 13 mutations (81%) were single-base changes. Of these, five were due to transitions at CpG (Table 6). In HB2, glutamine substitutes for argine 29 in the calcium binding domain; in HB4, serine substitutes for glycine 60 in the first growth factor domain; in HB25, histidine substitutes for arginine 145 in the activation peptide as has previously been described (Noyes et al., 1983); in HB1, a threonine substitutes for alanine 233 in the catalytic domain, and in HB19, methionine substitutes for threoinine 296 in the catalytic domain. In HB2, a silent T→C transition also occurs more than 23,000 bp downstream at valine 227 in Region G.

Of the 21 hemophiliacs with discrete sequence changes, HB2 i the only one who had two sequence changes. As the silent change might well represent a polymorphism Region G was sequenced in another 30 normal individuals but no sequence change was found anywhere in the region. Thus the silent change in HB2 was not found in 50 normal factor IX genes and it did not appear as a second sequence change in the other hemophiliac factor IX genes. Hence, the change represents either a low frequency polymorphism/rare variant or a second mutation in HB2 as commonly occurs in cells exposed to mutagens that act at the replication fork or in cells with nucleotide pool abnormalities [Phear G., J. Nalbantoglu, M. Meuth, Proc. Natl. Acad. Sci. USA 84:4450–4454 (1987)]. As the nature of the change is currently unclear, it will not be used in subsequent calculations.

It is infered that the causative mutations have been found because only one candidate mutation was seen in each individual and the rate of polymorphism in these regions of factor IX is very low. Furthermore, the amino acids affected by substitution mutations are conserved in the two to six species where factor IX sequence data is available [Katayama K., L. H. Ericsson, D. L. Enfield, K. A. Walsh, H. Neurath, E. W. Davie, K. Titani, Proc. Natl. Acad. Sci. USA, 76:4990–4994 (1979); Sarkar G. and Sommer S. S., Science, 244:331–334 (1989)].

Rate of Mutational Enhancement

Eighty-one percent of the causative mutations were single-based changes. For these it is possible to calculate the enhancement of mutation relative to other single-base changes. The finding that 38% (5/13) of the single-base mutations were transitions at CpG contrasts with the expected frequency at random of 0.8%. The expectation of 0.8% was calculated by using an empirical estimate of 40% for transitions and 60% for transversions [Vogel and Motulsky, 1986] and determining that 52 CpG bp (19 sites in the coding region plus 7 sites elsewhere×2 bp per site) are present in the 2.46 kb which constitutes the eight regions. Therefore, $$\frac{0.008}{0.008\ F + 0.992} = \frac{5}{13}$$

where F=mutational enhancement factor. A 77-fold enhancement of mutation at CpG was calculated and a 95% confidence interval of 20 to 268 was determined from the binomial distribution.

Presumably the mutations reflect lack of DNA repair when the 5-methylcytidine that is present at CpG spontaneously deaminates to produce thymidine as has been shown in strains of E. coli that contain 5-methylcytidine [Coulandre C., J. H. Miller, P. J. Farabaugh, W. Gilbert, Nature, 274:775–780 (1978)]. Note that the G→A transition in the sense strand of HB1, 2, 4, and 25 corresponds to a C→T transition in the antisense strand. The dramatic enhancement of mutation of CpG raises the possibility that one-third or more of germline mutations in humans may well be due to "an endogenous system" which could be independent of environmental mutagens.

The sequence flanking CpG was variable and no obvious difference could be discerned between the sequence of these and the 21 CpG dinucleotides that were not mutated. This suggests that the in vivo rate of spontaneous deamination does not depend markedly on the sequence of adjacent bases.

Discussion

Eight regions of likely functional significance in the factor IX gene have been sequenced form 20 unrelated individuals without known coagulaopathy and from 21 individuals with hemophilia B. The rate of polymorphism in these regions is approximately one-third of the estimated average for the X chromosome. The estimated average of the X-chromosome reflects the rate of polymorphism in introns and intergenic sequences, while our calculations estimate the rate in exons and other regions of functional significance. For hemophiliacs, CpG was found to be a dramatic hotspot of point mutation, accounting for 5 of the 13 independent single-base mutations.

CpG

Previously, Southern blot analyses of TaqI digestions of the factor VIII gene have strongly suggested that CpG is a hotspot for mutation in that gene [Youssoufian et al., 1986; Youssoufian et al., 1988]. A review of published mutations [Cooper and Youssoufian, 1988] and sequence of seven mutations/polymorphisms in glucose-6-phosphate dehydrogenase (Vullimay et al., 1988) indicate that CpG is a hotspot for mutation. In contrast, CpG was not found to a hotspot in the α-globin and β-globin genes where the greatest number of single-base mutations have been delineated [Vogel and Motulsky 1986; Antonarakis, S. E., H. H. Kazazian, Jr., S. H. Orkin, Hum. Genet 69:1–14 (1985)]. In the case of α-globin, the frequency of GpC dinucleotides equals CpG dinucleotides throughout the gene, suggesting that the CpG is methylated in the germline [Bird, A.Nature 321:209–213 (1986)]. In the case of β-globin, it is quite possible that an enhancement of mutation at CpG is obscured by:

1. The nature of mutations at autosomal genes, i.e., new recessive mutations require many generations for elimination, thereby allowing heterozygote advantage and founder effects to distort the observed pattern of point mutations.
2. The nature of the data collected, i.e., many of the base changes were deduced from the amino acid sequence. Consequently multiple independent mutations at a CpG would not be distinguishable from the same mutation present in multiple individuals.
3. The paucity of CpG sites. No sites are present in the promoter and only five sites are present in exonic sequence. It is quite possible that one of these sites can generate the thalassemia phenotype, the only class of hemoglobinopathies where the available DNA sequence data could have detected multiple independent mutations.

Mutations

At least one mutation was found in each region except H-3' which contains the poly A addition site and 200+bp of neighboring sequence. Sequencing of the catalytic domain of six mammalian species indicates that the amino acid substitutions found in the hemophiliacs were at positions that were conserved in all the species as described hereinabove. Limited data is available for the amino acid substitutions outside the catalytic domain of factor IX.

The mutation in HB9 is intriguing in that an asparagine replaces a γ-carboxylated glutamic acid (gla). This is one of 12 gla residues which presumably chelates six moles of calcium. The marked decrease in activity (factor IX coagulant of 4%) hints that binding may be cooperative, as fluorescence data has suggested for prothrombin [Prendergast F. G., and K. G. Mann, J. Biol. Chem., 252:840–850 (1977)]. The substitutions at arginine 145 and isolecucine 397 have been previously described by others [Noyes C. M., M. J. Griffith, H. R. Roberts, R. L. Lundblad, Proc. Natl. Acad. Sci. USA, 80:4200–4202 (1983); Ware J., L. Davis, D. Frazier, S. P. Bajaj, D. W. Stafford, Blood, 72:820–822]. In our sample, multiple occurrences of the isoleucine 397 mutation in the same haplotype suggest that there is one ancestor common to these individuals.

As expected, a few of the mutations were not in the coding region. Interestingly, HB6 has a four base deletion 5 to 8 bp from the end of intron D which is associated with mild disease (factor IX coagulant of 20%). It is speculated that normal splicing still occurs 20% of the time while exon E is deleted from the mRNA the remaining 80% of the time. Without resorting to a liver biopsy, this hypothesis can potentially be tested by RAWTS. With RAWTS, a low level of basal transcription and processing can be detected for factor IX and other tissue specific mRNAs in many if not all tissues including blood.

DNA Diagnosis

The rapidity of GAWTS and the low frequency of polymorphism in the factor IX gene enables the method to be used clinically for carrier testing and prenatal diagnosis in hemophilia B, an X-linked lethal disease where each family generally will have a different mutation. After delineating the mutation in an affected individual in the family, direct diagnosis can be made by sequencing the appropriate region of an at-risk individual. This obviates may of the problems associated with the current RFLP-based methodology. In the future, the anticipated automation of GAWTS or related methods of genomic sequencing should allow direct diagnosis by sequence analysis to be extended to much larger genes such as the factor VIII gene which is defective in hemophilia A.

Note Added in Proof

The A→G translation at base 13 in the 5' untranslated region has recently been found in a hemophiliac with altered developmental expression of factor IX [Reitsma et al., 1989].

Currently a more standard measure of the extent of polymorphism is the quantity known as the average heterozygosity at the nucleotide level [Nei, personal communication]. The quantity is calculated by determining the number of mismatched bases for all combinations of pairwise sequence comparisons and the number of base pairs sequenced per individual [Nei M., Columbia University Press, p. 256, (1987)]. For 22 normal individuals where the sequence from all eight regions of factor IX is available, the average heterozygosity at the nucleotide level is 0.00024.

Direct diagnoses were made in 54 at-risk females by initially sequencing 2.46 kb in one hemophiliac per family with GAWTS. A presumptive mutation was found in each of the 14 hemophiliacs examined. Diagnoses were then made by either sequencing the appropriate region in at-risk females or detecting an altered restriction site. A stimulation indicates that the mutation will be associated with an altered restriction site in approximately 50% of the families.

The data demonstrate that GAWTS can be used to delineate the mutation and to perform direct carrier testing on a clinical time scale.

Hemophilia B is caused by a deficiency in factor IX coagulant activity, and occurs in approximately one of 30,000 males [McKee P. A., In: The Metabolic Basis of Inherited Disease, 5th ed. (eds. Stanbury J. B., J. B.

Wyngaarden, D. S. Fredrickson, H. Goldstein, M. S. Brown) pp 1531–1560, McGraw-Hill, New York (1983)]. At present, carrier status of hemophilia B in at-risk females is usually determined by linkage analysis with a restriction fragment length polymorphism (RFLP). Unfortunately, RFLP-based linkage analysis has several difficulties. First, an informative polymorphism must be found. In the case of hemophilia B, the probability of finding an informative polymorphism is only 80% in Caucasians [Winship P. R., G. G. Brownlee, Lancet, ii:218–19 (1986)] and less than 20% in other racial groups [Lubahn D. B, S. T. Lord, J. Bosco, J. Kirshtein, O. J. Jeffries, N. Parker, C. Levtzow, L. M. Silverman, J. B. Graham, Am. J. Hum. Genet., 40:527–536 (1987)]. Second, RFLP analysis requires blood samples from multiple family members who may be unavailable or uncooperative. Third, RFLP analysis is an indirect test which has may inherent uncertainties, including the possibility of recombination, nonpaternity, genetic heterogeneity, germline mosacism and ambiguities in the origin of the mutation in families with sporadic disease [Sommer, S. S., J. L. Sobell, Mayo Clin. Proc. 62:387–404 (1987)].

The problems with RFLP analysis can be circumvented by identifying the mutation and directly determining whether the at-risk females carry the mutation. Since each family usually has a unique mutation [Haldane J. B. S., J. Genet, 31:317–326 (1935)], direct diagnosis has not been feasible in a clinical setting. However, PCR-based sequencing [Stoflet, E. S., D. D. Koeberl, G. Sarkar, S. S. Sommer, Science, 239:419–424 (1988); Wong, C. C. E. Dowling, R. K. Saiki, R. G. Higuchi, H. A. Erlich, H. H. Kazazian, Jr., Nature, 330:394–396 (1988); Engelke D. R., P. A. Hoener, F. S. Collins, Proc. Natl. Acad. Sci. USA, 85:544–548 (1988); Gyllensten U. B., H. A. Erlich, Proc. Natl. Acad Sci. USA, 85:7652–7656 (1988); Mihovilovic M, J. E. Lee, Biotechniques, 7:14–16 (1989)] has now made it possible to provide direct diagnosis within a reasonable time frame. Direct carrier testing was performed in 14 families using the GAWTS method.

Methods

Blood was collected in ACD solution B and DNA was extracted as previously described [Gustafon, S., J. A. Proper, E. J. W. Bowies, S. S. Sommer, Anal. Biochem., 165:294–99 (1987)]. Sequencing was performed using genomic amplification with (GAWTS). In brief, the regions to be sequenced were amplified by the polymerase chain reaction (PCR) where one of the oligonucleotides had the T7 phage promoter. PCR was performed in a Perkin-Elmer-Cetus Thermal Cycler with Taq polymerase (Perkin-Elmer-Cetus), using a protocol detailed hereinabove. Control amplifications without genomic DNA template were routinely performed to monitor contamination of reagents. PCR aliquots were transcribed with T7 RNA polymerase (Promega). The RNA transcripts were used for dideoxy sequencing with AMV reverse transcriptase (Promega), primed with a nested (internal) oligonucleotide. A DNASTAR gel reader and computer software were used to align sequences with the published sequence [Yoshitake S., B. G. Schach, D. C. Foster, E. W. Davie, K. Kurachi, Biochemistry, 24:3736–3750 (1985)] and to determine if the changes altered any restriction sites.

The eight regions sequenced for each hemophiliac were as follows: Region A: −106–139; Region B/C: 20577–20334; Region D: 10544–10315; Region E: 17847–17601; Region F: 20577–20334; Region G: 30183–29978; Region H-5': 31411–30764; Region H-3': 32808–32583. The order of the numbers in each region indicates the direction of sequencing.

Haplotypes were determined by amplifying the flanking DNA of the polymorphic site and digesting the corresponding restriction enzyme. The three intragenic polymorphisms examined were Hinf1 (intro a). Xmn1 (intron c), and Taq1 (intron d) [Camerino G., K. H. Grzeschik, M. Jaye, H. DeLaSalle, P. Tolstoshev, J. P. Lecocq, R. Heilig, J. L. Handel, Proc. Natl. Acad. Sci., 81:498–502 (1984); Winship, P. R., D. S. Anson, C. R. Rizza, G. G. Brownlee, Nucleic Acids Res. 12:8861–8872 (1984)]. The Malmo allele (ala or thr at amino acid 148) was determined by GAWTS. These polymorphisms provide most of the information that can be obtained by RFLP analysis.

Results

In order to find the mutations in the probands, 2.46 kb of the 34 kb factor IX gene was sequenced in each hemophiliac by GAWTS. GAWTS is a three-step method. In the first step, genomic DNA is amplified with PCR, a technique that involves multiple cycles of: (1) denaturation of DNA, (2) annealing of oligonucleotide primers specific for the region of amplification, and (3) extension of the oligonucleotide primers also contains a bacteriophage promoter sequence. The T7 RNA polymerase. In step 3, the RNA is used as a singly-stranded template for sequencing by the Sanger dideoxy method.

Figure 24:
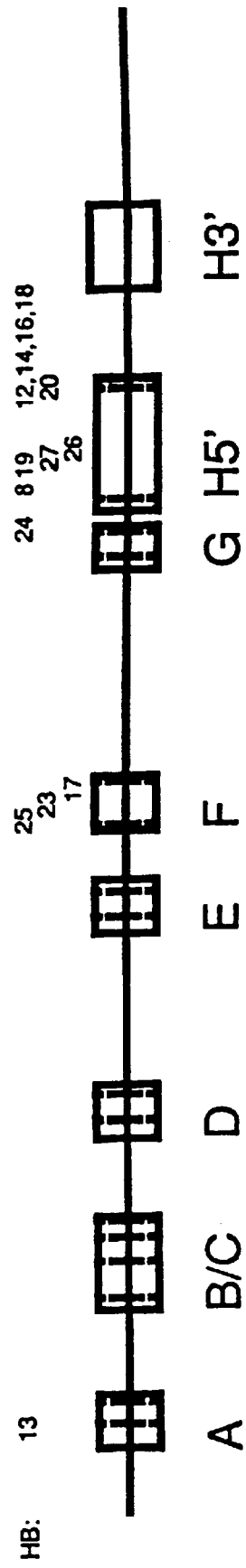
FIG. 24: Schematic of the eight regions sequenced in the factor IX gene. In each region (boxed), the coding sequences are delineated by broken lines. Additional sequences enclosed by the solid boxes include the promoter, the 5' untranslated sequence, the splice junctions, and parts of the 3' untranslated region including the poly A addition signal. The arrows indicate the start and stop of transcription. The unsequenced intronic segments which account for 92% of the gene are drawn to a different scale (kilobases vs. bases). The location of the mutation in each family is indicated.

Eight regions of the factor IX gene were sequenced. These regions were anticipated to contain the overwhelming majority of the causative mutations. The regions included the putative promoter, the coding sequence, the splice junctions, the 5' untranslated sequence, and the poly A addition region (FIG. 24). Region A contains the putative promoter, exon a, and the adjacent splice junction. Region B/C contains exon b, intron b, exon c, and the flanking splice junctions. Regions D–G contain the corresponding exon and flanking splice junctions. Region H-5' contains a splice junction, the amino acid coding sequence of exon h and the proximal 3' untranslated segment of the mRNA. Region H-3' contains the distal 3' untranslated region in exon h with the poly A addition sequence and the sequence immediately following the gene.

Once the mutation in the hemophiliac proband was identified, the region containing the mutation was also sequenced by GAWTS in family members requesting carrier testing. Alternatively, if the mutation in the proband changed a restriction site, the appropriate region was amplified in the at-risk females of the family and digested with the restriction endonuclease.

Direct Testing by Sequence Analysis

Figure 25A:
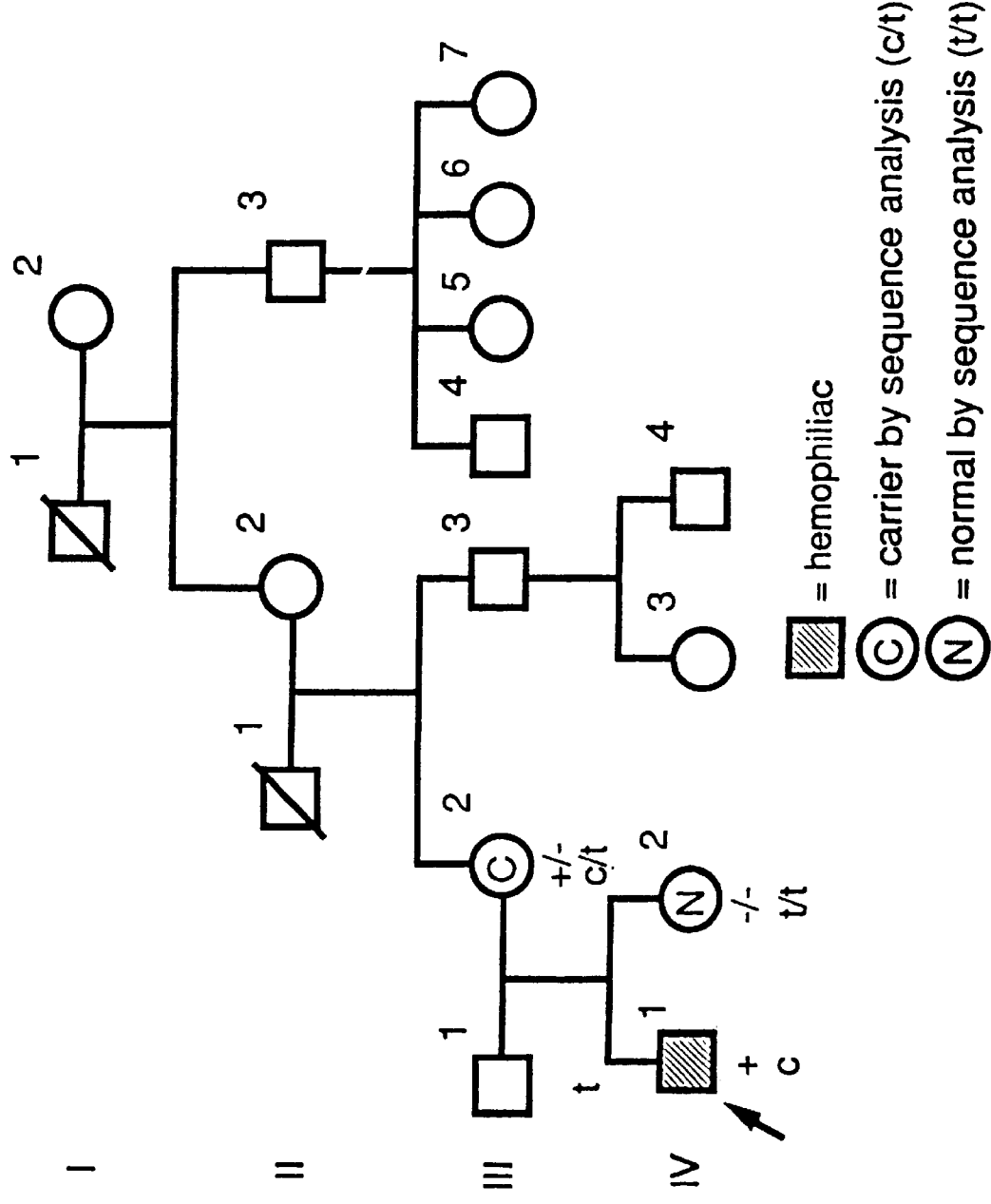
FIGS. 25A 25B: Pedigree of the family of HB27 by sequencing. Sequencing by GAWTS was performed as described in the Methods. 1 Proband HB27, 2. HB27 mother (carrier), 3. HB27 sister (noncarrier).

Certain advantages of carrier testing are illustrated with the family of HB27 (FIG. 25A). IV-1 is the only individual in the family known to be affected. The mother, III-2, wanted carrier testing for herself and here daughter (IV-2). Since the mutation could have occurred in the egg that gave rise to the hemophiliac, the mother may not be a carrier. In that case, her daughter would not be a carrier and any future male fetus would not be affected despite inheritance of the same RFLPs as the hemophiliac. Only direct detection of the mutation and not RFLP analysis can determine if the mother is a carrier. RFLP analysis can, however, accurately determine carrier status in the sister of a sporadic case of hemophilia if the mother is heterozygous for an intragenic RFLP (so that the factor IX alleles can be distinguished) and the sister does not inherit the same factor IX allele as her hemophiliac brother. Since these criteria were met in the sister of this family, IV-2 was diagnosed as a noncarrier.

Figure 25B:
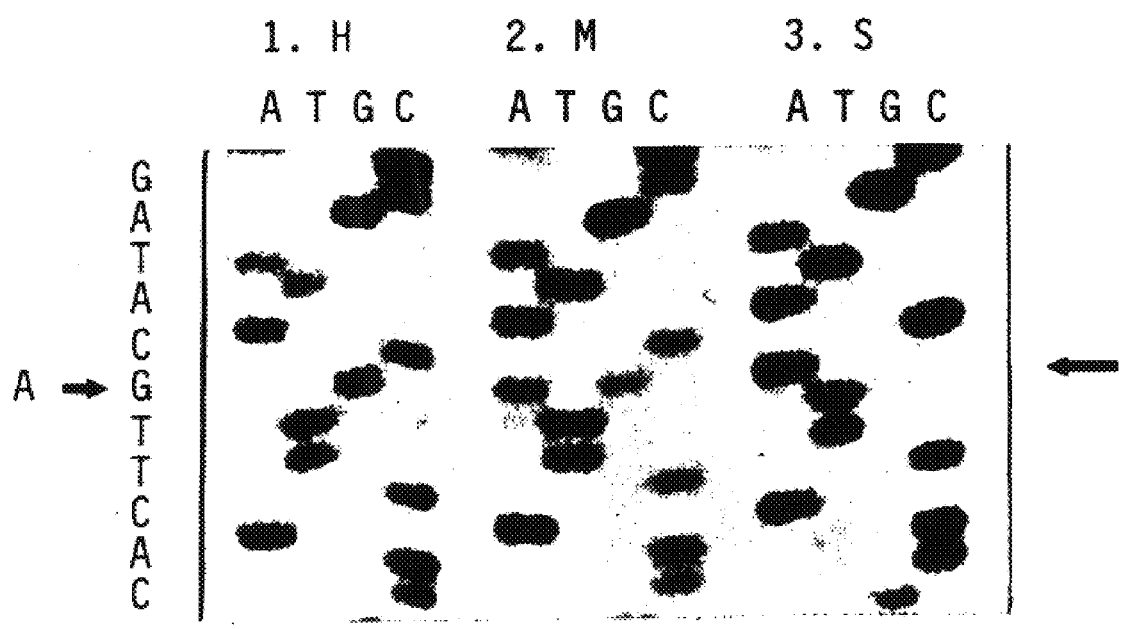

Direct sequencing of the eight regions of the hemophiliac revealed an T→C translation at base 31041 which substitutes an alanine for valine at position 307 (FIG. 25B). Sequence of the relevant region of the mother indicated that she was heterozygous for the mutation. Consequently, she is a carrier and the mutation must have originated in the germ cell of one of her parents or in a previous generation. Although the mother is at risk for having additional son with hemophilia, direct sequencing can be performed from chorionic villus samples or aminiotic fluid to determine whether a male fetus is affected.

Direct Testing by Restriction Endonuclease Digestion

Figure 26:
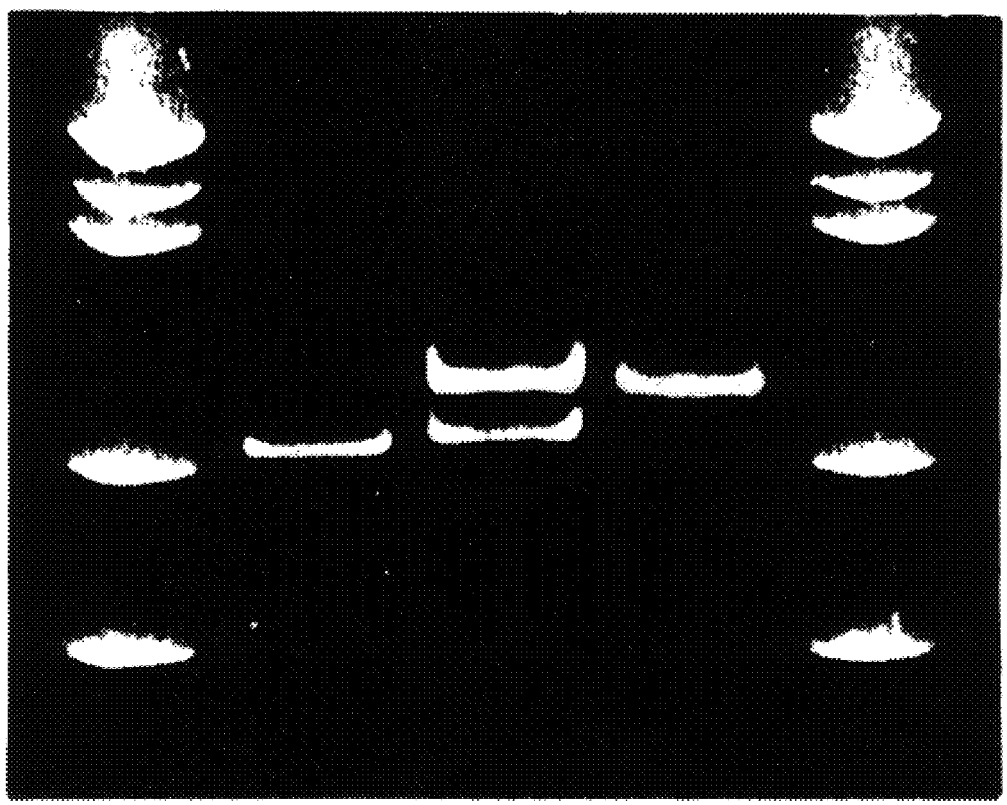
FIG. 26: Direct diagnosis in the family of HB20 by restriction digestion with HpaII. PCR amplification of the relevant segment, restriction digestion with HpaII, and polyacrylamide gel electrophoresis were performed. HB20 has acquired a novel HpaiII site 12 bp away from a normal site. The sequence data predicts that, after digestion with HpaII, HB20 DNA will produce a fragment of 12 bp (too small to be seen) and a fragment 12 bp smaller than normal. S-Standards ($\phi$X174 HaeIII restriction fragments from 194 to 310 bp). Lane H: HB20 (HpaII+), Lane C: HB20 mother (HpaII-/+, heterozygote carrier), Lane n: normal sequence (HpaII-).

When the mutation in the proband changes a restriction site, it is possible to perform carrier testing by amplification and detection of the altered site by restriction digestion rather than sequencing. The mutation in HB20, for instance, creates a new HpaII. Carrier status was determined by the presence of the HpaII site in the mother (FIG. 26).

TABLE 7

Direct Testing for Hemophilia Carriers in 14 Families

| Proband[1] | Factor IX:C[2] | Mutation | RS Change[3] | Pedigree type | Diagnoses[4] (C/N) |
|---|---|---|---|---|---|
| 13 | 32 | A -> G 5'UT[5] | — | familial | 0/3 |
| 25 | 4 | Arg$^{145}$- His | N1aIII+ | familial | 2/1 |
| 23 | <1 | 13 bp del after Ala$^{161}$ | — | sporadic | 1/1 |
| 17 | <1 | Gln$^{173}$ -> TAA | — | mother adopted | 1/0 |
| 24 | 1 | Cys$^{222}$ -> Trp | — | familial | 6/5 |
| 8 | 24 | Asn$^{260}$ -> Thr | — | familial | 1/4 |
| 19 | <1 | Thr$^{296}$ -> | N1aIII+ | familial | 5/4 |
| 27 | 18 | Val$^{307}$ -> Ala | — | sporadic | 1/1 |
| 26 | 3 | Gly$^{311}$ -> Arg | — | sporadic | 3/8 |
| 12 | 2 | Ile$^{397}$ -> Thr | — | familial | 1/0 |
| 14 | <1 | Ile$^{397}$ -> Thr | — | familial | 2/0 |
| 16 | <1 | Ile$^{397}$ -> Thr | — | familial | 1/1 |
| 18 | 2 | Ile$^{397}$ -> Thr | — | familial | 1/0 |
| 20 | <1 | Trp$^{407}$ -> Arg | HpaII+ | familial | 1/0 |

[1]The probands where at-risk females requested carrier are listed.
[2]Factor IX coagulants were provided by the Comprehensive Hemophilia Centers.
[3]Restriction site changes, The "+" indicate that a new site was created by the mutation.
[4]C = number of carriers/N = number of noncarriers
[5]The sequence change occurs in the 5' untranslated region of the mRNA.

SUMMARY OF DIRECT DIAGNOSES

A mutation was found in each of the 14 hemophiliacs sequenced (Table 7) Direct diagnosis was performed to determine whether an appropriate at-risk female was heterozygous for the mutation. Fifty-four direct diagnoses were made: 26 females were diagnosed as carriers and 28 were diagnosed as noncarriers. Of the 54 diagnoses, only 13 could have been determined by RFLP analysis. Polymorphisms were often uninformative and in many families only the probands and the at-risk females provided blood samples.

Eleven different single base pair mutations were found in the 14 families examined (Table 7). This was not surprising given that hemophilia B is an X-linked lethal disease which is normally extinguished within a few generations [Haldane, J. B. S, J. Genet., 31:317–326 (1935)]. Most of the mutations will be unique to a given family.

Of the 11 different mutations found in the 14 probands (Table 7), three of the mutations have been previously described. One mutation is an A→G transition at base +13, which is untranslated and, therefore, does not alter any amino acid [Reitsma, P. H., T. Mandalski, C. K. Kasper, R. M. Bertina, R. M. Briet, Blood, 73:743–746, (1989)]. Another mutation is an G→A transition at base 20414, changing arginine$^{145}$ to histidine. [Noyes, C. M., M. J. Griffith, H. R. Roberts, R. L. Lundblad, Proc. Natl. Acad. Sci., 80:4200–4202 (1983)]. The third mutation is a T→C transition at base 31311, changing isoleucine$^{397}$ to threonine [Ware, J., L. Davis, S. P. Bajaj, D. Stafford, Blood, 72:820–822, (1988)].

The ile$^{397}$ mutation, which causes mild hemophilia, was found in a total of four hemophiliacs, HB 12, 14, 16 and 18. The high incidence of this particular mutation (4/14) suggests that either there is a founder effect or base 31311 is a hotspot of mutation. The evidence strongly suggests a founder effect since each of the hemophiliacs with the ile$^{397}$ mutation has the same haplotype: TaqI-, Xmn1-, Hinf1-, and the Malmo allele=ala$^{148}$. The probability that these four hemophiliacs would have the same haplotype independently is less than 1.2% based on our observed frequencies for these polymorphisms.

Frequency of Restriction Site Changes

Of the 11 different mutations that were observed (Table 7), three of those changes resulted in the creation of a new restriction site (27%). Initially, this was surprising because the number of altered restriction sites due to single-base changes has been estimated at 5% [Antonarakis, S. E., et al., New Engl. J. Med., 313:842–848 (1985); Orkin, S. H., et al., Nature, 296:627–631 (1982)] To determine the expected number of changes in factor IX, every 25th base in Regions A through H-5' was changed using a random number generator. Ninety one locations were changed, and 49 (54%; 95% confidence interval, 43–64% by the binomial distribution) resulted in the loss and/or gain of one or more of the 137 restriction endonucleases were sufficient to cleave at each of the 49 susceptible sites. In the 49 changes with affected restriction specificities, a total of 107 different sites were altered. Only 37% were classical palindromic sequences (i.e., a complementary sequence without any intervening sequence).

To determine whether the high frequencies of altered sites was an unusual property of factor IX, random bases were changed at 100 locations separated by 25 bases in the cDNA sequence phenylalanine hydroxylase, a human autosomal gene and in the sequence of M13, a bacterial phage. The results indicate that 53% and 44%, respectively, of the base changes altered one or more restriction sites. The higher fraction of changes that were found compared to previous estimates presumably reflects the increased proliferation of restriction enzyme, especially those that recognize non-pallindromic sequences.

Discussion

GAWTS has been applied to the direct diagnosis of carrier status in 54 females. The mutation was delineated in a hemophiliac family member and carrier testing was then performed in at-risk females by either sequencing the relevant region or amplifying the region and digesting with a restriction endonuclease. These direct diagnoses do not suffer from the uncertainties which can plague RFLP testing. Those females diagnosed as carriers can now avail themselves of direct carrier testing on a clinical time scale. After the mutation is found in the proband, the diagnosis in a substantial fraction of families can be made by restriction endonuclease digestion. A survey of 137 restriction specifities indicates that approximately 50% of base changes will affect one or more sites. As more restriction endonucleases are discovered, the percentage of diagnoses that can be determined in this manner will increase.

A major advantage of sequencing DNA from the hemophiliac is that a sequence change is seen as both the presence of a new base and the absence of the normal base. If an affected male is unavailable, it may be necessary to sequence the at-risk female. To distinguish clearly a sequence change on one of the two X chromosomes of the female, any shadow bands that occasionally occur due to nonspecific termiation by reverse transcriptase must be eliminated. It may be necessary to sequence both strands by attaching different phage promoters to the PCR primers during GAWTS.

For each hemophiliac sequenced, one mutation has been identified (Table 7). It is infer that these changes represent the causative mutation in each family because (1) they are the only changes found in the regions of functional significance, (2) the changes have not be seen in 20 unrelated unaffected individuals as stated hereinabove or have they been observed as second sequence changes in 30 unrelated hemophilia genes, and (3) there is a low rate of polymorphism in the regions sequenced. In each family except number 13 (where no amino acid change occurs), one or more additional criteria have also been met: (1) the amino acid altered is evolutionarily conserved in factor IX of other species (2) the amino acid is evolutionarily conserved in related serine proteases, and (3) there is biochemical evidence for the functional importance of the altered amino acid (e.g., the mutation in HB25 [Noyes et al., 1983]).

Although the evidence for delineation of the causative muatation is compelling, it is conceivable that a rare polymorphism might occasionally be mistaken for the mutation. In such a case, carrier testing will still be reasonably accurate. Each change will be tightly linked to the causative mutation with the 34 kb factor IX gene. The probability of an error in diagnosis due to recombination will be very small (<1%). Given the low rate of polymorphism dicussed hereinabove the probability is also very small that another copy of the same sequence change would occur within one family and lead to a false positive diagnosis.

PCR-based sequencing of genomic DNA allows rapid and direct diagnosis of carriers and noncarriers in diseases where each family is expected to have a different mutation. Automation would further enhance the rate of sequencing, enabling routine direct diagnosis for larger gene such as factor VIII. Direct sequencing can also be applied to other areas of medicine. For example, accurate prognosis or better therapy of an individual's neoplasm may be achieved by determining which oncogenes and tumor suppressor genes have mutated.

What is claimed is:

1. A method of amplifying a sequence of interest present within a nucleic acid molecule which comprises:

A) obtaining a sample of the nucleic acid molecule which contains the sequence of interest;

B) if the nucleic acid molecule is a single-stranded RNA molecule, treating the sample from step (A) so as to prepare a sample containing a DNA molecule which contains a sequence complementary to the sequence of interest;

C) treating the sample from step (A) if the nucleic acid molecule is a DNA molecule or the sample from step (B) if the nucleic acid molecule is a single-stranded RNA molecule so as to obtain a further sample containing a single-stranded DNA molecule which contains a sequence complementary to the sequence of interest;

D) contacting the further sample from step (C) under hybridizing conditions with one oligonucleotide primer which includes at least (a) a promoter and (b) a nucleic acid sequence present within the nucleic acid molecule which contains the sequence of interest, which primer sequence is located adjacent to, and 5' of, the sequence of interest, so that the oligonucleotide primer hybridizes with the single-stranded DNA molecule which contains the sequence complementary to the sequence of interest;

E) treating the resulting sample containing the single-stranded DNA molecule to which the oligonucleotide primer is hybridized from step (D) with a polymerase under polymerizing conditions so that a DNA extension product of the oligonucleotide primer is synthesized, which DNA extension product contains the sequence of interest;

F) treating the sample from step (E) so as to separate the DNA extension product from the single-stranded DNA molecule on which it was synthesized and thereby obtain single-stranded DNA molecules;

G) contacting the resulting sample from step (F) containing the single-stranded DNA molecule which contains the sequence complementary to the sequence of interest under hybridizing conditions, with one oligonucleotide primer, which includes at least (a) a promoter and (b) a nucleic acid sequence located adjacent to, and 5' of, the sequence of interest, so that the oligonucleotide primer hybridizes with the single-stranded DNA molecule present in the sample which contains the sequence complementary to the sequence of interest;

H) treating the sample containing the single-stranded DNA molecule to which the oligonucleotide primer is hybridized from step (G) with a polymerase so as to synthesize a further DNA extension product containing the sequence complementary to the sequence of interest;

I) repeating steps (F) through (H), as desired;

J) contacting the sample from step (I) with an RNA polymerase which initiates polymerization from the promoter present, under polymerizing conditions, so as to obtain multiple RNA transcripts of each DNA extension product which contains the sequence complementary to the sequence of interest, thereby amplifying the sequence of interest.

2. A method of amplifying a sequence of interest present within a nucleic acid molecule which comprises:

A) obtaining a sample of the nucleic acid molecule which contains the sequence of interest;

B) if the nucleic acid molecule is a single-stranded RNA molecule, treating the sample from step (A) so as to prepare a sample containing a DNA molecule which contains a sequence complementary to the sequence of interest;

C) treating the sample from step (A) if the nucleic acid molecule is a DNA molecule or the sample from step (B) if the nucleic acid molecule is a single-stranded RNA molecule so as to obtain a further sample containing a single-stranded DNA molecule which contains a sequence complementary to the sequence of interest;

D) contacting the further sample from step (C) under hybridizing conditions with two or more oligonucleotide primers at least one of which includes at least (a) a promoter and (b) a nucleic acid sequence present within the nucleic acid molecule which contains the sequence of interest, which primer sequence is located adjacent to, and 5' of, the sequence of interest, and at least one other of which includes a nucleic acid sequence complementary to a sequence present within the nucleic acid molecule which contains the sequence of interest, which primer sequence is located adjacent to, and 5' of, the nucleic acid sequence complementary to the sequence within the nucleic acid molecule which contains the sequence of interest, so that at least one of the oligonucleotide primers hybridizes with the single-stranded DNA molecule present in the sample which contains the sequence complementary to the sequence of interest, and at least one other of the oligonucleotide primers hybridizes with the single-stranded DNA molecule which contains the sequence of interest;

E) treating the resulting sample containing the single-stranded DNA molecules to which the oligonucleotide primers are hybridized from step (D) with a polymerase under polymerizing conditions so that DNA extension products of the oligonucleotide primers are synthesized, some of which DNA extension products contain the sequence of interest and some of which DNA extension products contain the sequence complementary to the sequence of interest;

F) treating the sample from step (E) so as to separate the DNA extension products from the single-stranded DNA molecules on which they were synthesized and thereby obtain single-stranded DNA molecules;

G) contacting the resulting sample from step (F) containing the single-stranded DNA molecule which contains the sequence complementary to the sequence of interest under hybridizing conditions, with two or more oligonucleotide primers at least one which includes at least (a) a promoter and (b) a nucleic acid sequence located adjacent to, and 5' of, the sequence of interest, and at least one other of which includes a nucleic acid sequence complementary to a sequence present within the nucleic acid molecule which contains the sequence of interest, which primer sequence is located adjacent to, and 5' of, the nucleic acid sequence complementary to the sequence within the nucleic acid molecule which contains the sequence of interest, so that at least one of the oligonucleotide primers DNA molecule present in the sample which contains the sequence complementary to the sequence of interest, and at least one other of the oligonucleotide primers hybridizes with the single-stranded DNA molecule which contains the sequence of interest;

H) at least treating the sample containing the single-stranded DNA molecules to which the oligonucleotide primers are hybridized from step (G) with polymerase so as to synthesize further DNA extension products, some of which DNA extension products contain the sequence of interest and some of which DNA extension products contain the sequence complementary to the sequence of interest;

I) repeating steps (F) through (H), as desired;

J) contacting the sample from step (I) with an RNA polymerase which initiates polymerization from the promoter present, under polymerizing conditions, so as to obtain multiple RNA transcripts of each DNA extension product which contains the sequence complementary to the sequence of interest, thereby amplifying the sequence of interest.

3. A method of detecting a point mutation or polymorphism in a nucleic acid molecule which comprises:

(a) amplifying the sequence of interest present within the nucleic acid molecule by the method of claim 1 or 2, wherein the oligonucleotide primer sequence of interest hybridizes to a sequence of the nucleic acid molecule containing the nucleotide point mutation;

(b) determining the amount RNA produced in step (J) of claim 1 or 2; and (c) comparing the amount of RNA corresponding to the sequence of interest which has been produced with the amount of RNA expected, an increased amount of RNA indicating the presence of point mutation.

4. A method of carrier testing which comprises:

a) obtaining a sample containing the nucleic acid molecule of interest from a subject; and b) detecting the presence of a point mutation in the nucleic acid molecule of interest using the method of claim 3 thereby determining whether the subject is a carrier.

5. A method of prenatal diagnosis which comprises:

a) obtaining a sample containing the nucleic acid molecule of interest from a subject; and b) detecting the presence of a point mutation in the nucleic acid molecule of interest using the method of claim 3 thereby determining whether the subject has the tested for mutation.

6. A method of detecting the presence a mutation or polymorphism in a nucleic acid molecule which comprises:

a) amplifying the sequence of interest present within the nucleic acid molecule in a sample by the method of claim 1 or 2;

b) separating the amplified sequence of interest generated in step (a) from the sample; and c) comparing the sequence obtained in step (b) with a normal sequence thereby detecting the presence of a mutation or polymorphism.

7. A method of sequencing homologous genes in different species which comprises determining the exonic sequence of the gene of interest using a method which comprises:

a) amplifying the exonic sequence;

b) if the sequence generated in step (a) is double-stranded, treating the molecule to generate single-stranded nucleic acid molecules;

c) determining the sequence of the single-stranded nucleic acid molecules of either step (a) or (b) thereby determining the nucleotide sequence of the exonic sequence, wherein the gene of interest is identified by binding a primer corresponding to a nucleic acid sequence determined in a different species.

8. A method of a sequencing a region of a nucleic acid molecule which is adjacent to a known region of a known sequence which comprises:

a) annealing an oligonucleotide containing a promoter to the known region of the nucleic acid molecule;

b) extending the oligonucleotide to the region to be sequenced so that the extension product for primer is complementary to the unknown region of the nucleic acid;

c) isolating the portion of the oligonucleotide extension product which is complementary to the region to be sequenced;

d) treating the oligonucleotide extension product which is complementary to the region to be sequenced so as to add a promoter;

e) transcribing the sequence of the oligonucleotide extension product;

f) treating the transcript so produced as to prepare a cDNA which is complementary to the transcript; and g) sequencing the cDNA using a method which comprises:

i) amplifying the cDNA;

ii) if the sequence generated in step (i) is double-stranded, treating the molecule to generate single-stranded nucleic acid molecules;

iii) determining the sequence of the single-stranded nucleic acid molecules of either step (i) or (ii) thereby determining the nucleotide sequence of the cDNA.

9. A method of detecting and determining mutations and polymorphisms in the sequence of a nucleic acid which comprises:

a) determining the sequence of the nucleic acid by a method which comprises:

i) amplifying the amount of the nucleic acid;

ii) if the sequence generated in step (i) is double-stranded, treating the molecule to generate single-stranded nucleic acid molecules;

iii) determining the sequence of the single-stranded nucleic acid molecules of either step (i) or (ii) thereby determining the nucleotide sequence of the nucleic acid;

b) comparing the sequence obtained with that of the normal sequence, known mutations, and polymorphisms.

10. A method of claim 9, wherein the mutation is detected in an oncogene.

11. A method of monitoring the progression of a cancer which comprises detecting and determining mutation and polymorphism in an oncogene using the method of claim 1, and comparing the types of mutation and polymorphism determined with the type of mutation and polymorphism determined at earlier points of time, a change in the types of mutation and polymorphism indicating the progression of the disease.

12. A method of monitoring the efficiency of treatment of a cancer which comprises detecting and determining mutation and polymorphism in an oncogene using the method of claim 10, and comparing the type of mutation and polymorphism with the type of mutation and polymorphism determined at earlier points in time, a change in the types of mutation and polymorphism indicating the efficiency of the treatment.

13. A method of diagnosing and subtyping infectious agents which comprises:

a) obtaining a sample containing the agent to be analyzed;

b) treating the sample so as to make the nucleic acid molecule to be tested accessible to analysis;

c) determining the nucleotide sequence of the nucleic acid molecule from the infectious agent by the method of claim 9; and d) comparing the nucleotide sequence obtained with known sequences of nucleotide, thereby diagnosing and subtyping the infectious agents.

14. A method of claim 1 or 2, wherein the nucleic acid molecule containing the sequence of interest comprises double-stranded DNA.

15. A method of claim 14, wherein the double-stranded DNA comprises genomic DNA.

16. A method of claim 1 or 2, wherein the nucleic acid molecule containing the sequence of interest comprises cDNA.

17. A method of claim 1 or 2, wherein the nucleic acid molecule containing the sequence of interest comprises RNA.

18. A method of claim 17, wherein the nucleic acid molecule containing the sequence of interest comprises mRNA.

19. A method of claim 1 or 2, wherein the sample comprises a biological sample.

20. A method of claim 19, wherein the biological sample is a cell sample.

21. A method of claim 19, wherein the biological sample is a tissue sample.

22. A method of claim 21, wherein the tissue sample is blood.

23. A method of claim 1 or 2, wherein the promoter is a phage promoter.

24. A method of claim 23, wherein the phage promoter is a T7 promoter.

25. A method of claim 23, wherein the phage promoter is a T3 promoter.

26. A method of claim 23, wherein the phage promoter is an SP6 promoter.

27. A method of claim 1 or 2, wherein in step (D) the oligonucleotide primer which hybridizes with the single-stranded DNA molecule which contains the sequence complementary to the sequence of interest comprises a T7 promoter and in step (J) the RNA polymerase comprises a T7 RNA polymerase.

28. A method of claim 1 or 2, wherein in step (D) the oligonucleotide primer which hybridizes with the single-stranded DNA molecule which contains the sequence complementary to the sequence of interest comprises a T3 promoter and in step (J) the RNA polymerase comprises a T3 RNA polymerase.

29. A method of claim 1 or 2, wherein in step (D) the oligonucleotide primer which hybridizes with the single-stranded DNA molecule which contains the sequence complementary to the sequence of interest comprises a SP6 promoter and in step (J) the RNA polymerase comprises a SP6 RNA polymerase.

30. A method of determining the nucleotide sequence of a sequence of interest present within a nucleic acid molecule which comprises:

(a) amplifying the sequence of the nucleic acid molecule to be determined using the method of claim 1 or 2;

(b) treating the sample from step (J) of claim 1 or 2, under conditions such that a primer hybridizes to the RNA transcript;

(c) contacting the sample from step (b) with a polymerase under polymerizing conditions such that a single-stranded nucleic acid molecule which is complementary to the RNA transcript is synthesized; and (d) determining the nucleotide sequence of the single-stranded nucleic acid molecule obtained in step (c) thereby determining the nucleotide sequence of a sequence of interest.

31. A method of claim 30, wherein the polymerase is reverse transcriptase.

32. A method of claim 30, wherein in step (d) the determining comprises enzymatic sequencing.

33. A method of claim 32, wherein the enzymatic sequencing comprises Sanger dideoxy sequencing.

34. A method of claim 30, wherein in step (d) the determining comprises chemical sequencing.

35. A method of claim 34, wherein the chemical sequencing comprises Maxam Gilbert sequencing.

36. A method of claim 30, wherein in step (d) the determining comprises both chemical and enzymatic sequencing.

37. A method of claim 36, wherein the sequencing comprises the use of phosphorothioate.

* * * * *